United States Patent
Suraru et al.

(10) Patent No.: US 9,583,719 B2
(45) Date of Patent: Feb. 28, 2017

(54) CARBAZOLOCARBAZOL-BIS(DICARBOXIMIDES) AND THEIR USE AS SEMICONDUCTORS

(75) Inventors: Sabin-Lucian Suraru, Würzburg (DE); Frank Würthner, Höchberg (DE); Thomas Geβner, Heidelberg (DE)

(73) Assignee: BASF SE, Ludwigshafen (DE)

( * ) Notice: Subject to any disclaimer, the term of this patent is extended or adjusted under 35 U.S.C. 154(b) by 560 days.

(21) Appl. No.: 14/238,382

(22) PCT Filed: Aug. 10, 2012

(86) PCT No.: PCT/IB2012/054075
§ 371 (c)(1),
(2), (4) Date: Apr. 18, 2014

(87) PCT Pub. No.: WO2013/024409
PCT Pub. Date: Feb. 21, 2013

(65) Prior Publication Data
US 2014/0231773 A1     Aug. 21, 2014

Related U.S. Application Data

(60) Provisional application No. 61/522,716, filed on Aug. 12, 2011.

(51) Int. Cl.
| | |
|---|---|
| *H01L 51/54* | (2006.01) |
| *C09K 11/06* | (2006.01) |
| *H01L 51/00* | (2006.01) |
| *H05B 33/10* | (2006.01) |
| *C07D 471/22* | (2006.01) |
| *H01L 51/05* | (2006.01) |

(52) U.S. Cl.
CPC ........ *H01L 51/0072* (2013.01); *C07D 471/22* (2013.01); *C09K 11/06* (2013.01); *H01L 51/0053* (2013.01); *H05B 33/10* (2013.01); *C09K 2211/1007* (2013.01); *C09K 2211/1011* (2013.01); *C09K 2211/1029* (2013.01); *H01L 51/0545* (2013.01); *H01L 51/0558* (2013.01); *Y02E 10/549* (2013.01)

(58) Field of Classification Search
CPC ..... H05B 33/10; Y02E 10/549; C07D 471/00; C07D 471/22; C09K 11/06; C09K 2211/1003; C09K 2211/1007; C09K 2211/1011; C09K 2211/1018; C09K 2211/1022; C09K 2211/1029; C09K 2211/1074; H01L 51/0032; H01L 51/0052; H01L 51/0053; H01L 51/0071; H01L 51/0072; H01L 51/05; H01L 51/0545; H01L 51/0558; H01L 51/50; H01L 51/5048; H01L 51/5056; H01L 51/5088
USPC ....... 428/690, 691, 917, 411.4, 336; 427/58, 427/66; 313/500–512; 257/40, 88–104, 257/E51.001–E51.052; 252/301.16–301.35; 546/32
See application file for complete search history.

(56) References Cited

U.S. PATENT DOCUMENTS

| | | | |
|---|---|---|---|
| 8,471,020 B2 | 6/2013 | Reichelt et al. | |
| 8,610,893 B2 | 12/2013 | Sens et al. | |
| 8,691,401 B2 | 4/2014 | Molt et al. | |
| 2008/0021220 A1 | 1/2008 | Marks et al. | |
| 2011/0309343 A1 | 12/2011 | Langer et al. | |
| 2011/0309346 A1 | 12/2011 | Watanabe et al. | |
| 2012/0059168 A1 | 3/2012 | Könemann | |
| 2012/0074393 A1 | 3/2012 | Würthner et al. | |
| 2012/0205645 A1 | 8/2012 | Fuchs et al. | |
| 2012/0253045 A1 | 10/2012 | Gao et al. | |
| 2012/0267579 A1 | 10/2012 | Hwang et al. | |
| 2012/0289703 A1 | 11/2012 | Reichelt et al. | |
| 2012/0319050 A1 | 12/2012 | Metz et al. | |
| 2013/0211088 A1 | 8/2013 | Gessner et al. | |
| 2013/0234427 A1 | 9/2013 | Reichelt et al. | |
| 2013/0289279 A1 | 10/2013 | Gessner et al. | |

FOREIGN PATENT DOCUMENTS

| | | |
|---|---|---|
| CN | 1990488 A | 7/2007 |
| JP | 2009-521421 | 6/2009 |
| WO | WO 2007/074137 A1 | 7/2007 |
| WO | WO 2009/089283 A2 | 7/2009 |
| WO | WO 2011/045253 A1 | 4/2011 |
| WO | WO 2011/045294 A1 | 4/2011 |
| WO | WO 2011/047624 A1 | 4/2011 |
| WO | WO 2011/051404 A1 | 5/2011 |
| WO | WO 2011/157790 A1 | 12/2011 |
| WO | WO 2011/158204 A1 | 12/2011 |
| WO | WO 2012/020327 A1 | 2/2012 |
| WO | WO 2012/041849 A1 | 4/2012 |
| WO | WO 2012/069518 A1 | 5/2012 |
| WO | WO 2012/095790 A1 | 7/2012 |
| WO | WO 2012/117089 A1 | 9/2012 |

(Continued)

OTHER PUBLICATIONS

Yu Tao, et al., "Research Progress of carbazole derivatives as organic electroluminescent materials" New Chemical Materials, vol. 37, No. 5, May 15, 2009, pp. 6-8 (with an English Abstract and English translation).
International Search Report issued Jan. 10, 2013 in PCT/IB2012/054075.
Filippo Doria, et al., "Substituted Heterocyclic Naphthalene Diimides with Unexpected Acidity. Synthesis, Properties, and Reactivity" Journal of Organic Chemistry, vol. 74, No. 22, Oct. 22, 2009, pp. 8616-8625.
Heinz Langhals, et al., "Laterally Extended Naphthalene Tetracarboxylic Bisimides" Journal of Organic Chemistry, vol. 75, No. 22, Oct. 22, 2010, pp. 7781-7784.
Chunjie Zhou, et al., "An Unusual Addiction Reaction for Constructing a Novel pH-Controlled Fluorescence Switch" Organic Letters 2011, vol. 13, No. 2, Dec. 9, 2010, pp. 292-295.

(Continued)

*Primary Examiner* — Andrew K Bohaty
(74) *Attorney, Agent, or Firm* — Oblon, McClelland, Maier & Neustadt, L.L.P.

(57) ABSTRACT

The present invention relates to carbazolocarbazol-bis(dicarboximides), a method for their preparation and their use as semiconductors, in particular as semiconductors in organic electronics and organic photovoltaics.

28 Claims, 3 Drawing Sheets

(56) References Cited

FOREIGN PATENT DOCUMENTS

| WO | WO 2012/152598 A1 | 11/2012 |
|---|---|---|
| WO | WO 2012/172482 A1 | 12/2012 |
| WO | WO 2013/024026 A1 | 2/2013 |

OTHER PUBLICATIONS

Christoph Thalacker, et al., "Synthesis and Optical and Redox Properties of Core-Substituted Naphthalene Diimide Dyes" Journal of Organic Chemistry, vol. 71, No. 21, Sep. 19, 2006, pp. 8098-8105.

Frank Wurthner, et al. "Core-Substituted Naphthalene Bisimides: New Fluorophors with Tunable Emission Wavelength for Fret Studies" Chem. Eur. J. vol. 8, No. 20, 2002, pp. 4742-4750.

Xinyu Lu, et al., "Near-IR Core Substituted Naphthalenediimide Fluorescent Chemosensors for Zinc Ions: Ligand Effects on PET and ICT Channels" Chem. Eur. J., vol. 16, 2010, pp. 8355-8364.

Stephanie Chopin, et al., "Syntheses and Properties of Core-Substituted Naphthalene Bisimides with Aryl Ethynyl or Cyano Groups" Journal of Materials Chemistry, vol. 17, Jul. 23, 2007, pp. 4139-4146.

Yunbin Hu, et al., "Core-Expanded Naphthalene Diimides Fused with Sulfur Heterocycles and End-Capped with Electron-Withdrawing Groups for Air-Stable Solution-Processed n-Channel Organic Thin Film Transistors" Chemistry of Materials, vol. 23, Jan. 20, 2011, pp. 1204-1215.

Xike Gao, et al., "Core-Expanded Naphthalene Diimides Fused with 2-(1,3- Dithiol-2-Ylidene)Malonitrile Groups for High-Performance, Ambient-Stable, Solution-Processed n-Channel Organic Thin Film Transistors" Journal of American Chemical Society, vol. 132, 2010, pp. 3697-3699.

Office Action issued Mar. 7, 2016 in Japanese Patent Application No. 2014-525534 (English translation only).

CARBAZOLOCARBAZOL-BIS(DICARBOXIMIDES) AND THEIR USE AS SEMICONDUCTORS

FIELD OF THE INVENTION

The present invention relates to carbazolocarbazol-bis (dicarboximides), a method for their preparation and their use as semiconductors, in particular as semiconductors in organic electronics and organic photovoltaics.

It is expected that, in the future, not only the classical inorganic semiconductors but increasingly also organic semiconductors based on low molecular weight or polymeric materials will be used in many sectors of the electronics industry. In many cases, these organic semiconductors have advantages over the classical inorganic semiconductors, for example better substrate compatibility and better processibility of the semiconductor components based on them. They allow processing on flexible substrates and enable their interface orbital energies to be adjusted precisely to the particular application range by the methods of molecular modeling. The significantly reduced costs of such components have brought a renaissance to the field of research of organic electronics.

Organic electronics is concerned principally with the development of new materials and manufacturing processes for the production of electronic components based on organic semiconductor layers. These include in particular organic field-effect transistors (OFETs) and organic electroluminescent devices (hereinafter abbreviated as "EL" devices). Great potential for development is ascribed to organic field-effect transistors, for example in storage elements and integrated optoelectronic devices. An organic electroluminescent device is a self-emission device utilizing the principle that a fluorescent material emits light by the recombination energy of holes injected from an anode and electrons injected from a cathode when an electric field is applied. EL devices in form of organic light-emitting diodes (OLEDs) are especially of interest as an alternative to cathode ray tubes and liquid-crystal displays for producing flat visual display units. Owing to the very compact design and the intrinsically low power consumption, devices which comprise OLEDs are suitable especially for mobile applications, for example for applications in cell phones, laptops, etc.

Organic photovoltaics is concerned principally with the development of new materials for organic solar cells. A great potential for development is ascribed to materials which have maximum transport widths and high mobilities for light-induced excited states (high exciton diffusion lengths) and are thus advantageously suitable for use as an active material in so-called excitonic solar cells. It is generally possible with solar cells based on such materials to achieve very good quantum yields. There is therefore a great need for organic compounds which are suitable as charge transport materials or exciton transport materials.

WO 2007/074137 describes naphthalenetetracarboxylic acid derivates of the formula (I)

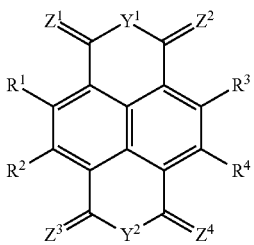

where at least one of the $R^1$, $R^2$, $R^3$ and $R^4$ radicals is a substituent which is selected from Br, F and CN,
$Y^1$ is O or $NR^a$, where $R^a$ is hydrogen or an organyl radical,
$Y^2$ is O or $NR^b$, where $R^b$ is hydrogen or an organyl radical,
$Z^1$ and $Z^2$ are each independently O or $NR^c$, where $R^c$ is an organyl radical,
$Z^3$ and $Z^4$ are each independently O or $NR^d$, where $R^d$ is an organyl radical,
a process for preparing them their use as n-type semiconductors.

WO 2009/089283 describes hybrid semiconducting-dielectric materials, for example tetracarboxylic diimide compounds having a condensed aromatic moiety with 2 to 6 fused aromatic rings or heterocyclic variants thereof. Carbazolocarbazol-bis(dicarboximides) are not disclosed.

CN 1990488 A describes an n type organic semi-conductor material that is a cyclic imide derivative of a linear fused aromatic rings.

X. Gao et al. describe in J. Am. Chem. Soc. 2010, 132, 3697-3699 core-expanded naphthalene diimides fused with 2-(1,3-dithiol-2-ylidene)malonitril groups and their use for n-channel organic thin film transistors. A corresponding disclosure can be found in WO 2011/047624.

Y. Hu et al. describe in Chem. Mater. 2011, 23, 1204-1215 core-expanded naphthalene diimides fused with sulphur heterocycles and end-capped with electron withdrawing groups for n-channel organic thin film transistors.

It has now been found that, surprisingly, carbazolocarbazol-bis(dicarboximides) are particularly advantageous as semiconductor materials in organic electronics and organic photovoltaics.

SUMMARY OF THE INVENTION

According to a first aspect of the present invention there is provided a compound of the general formula I

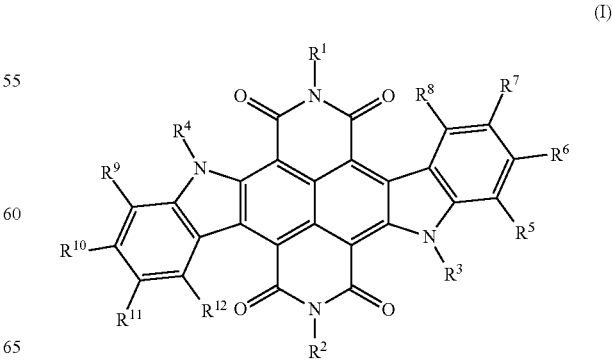

wherein

R$^1$ and R$^2$ are each independently selected from hydrogen and in each case unsubstituted or substituted alkyl, cycloalkyl, heterocycloalkyl, aryl and hetaryl, R$^3$ and R$^4$ are each independently selected from hydrogen and in each case unsubstituted or substituted alkyl, cycloalkyl, heterocycloalkyl, aryl and hetaryl, R$^5$, R$^6$, R$^7$, R$^8$, R$^9$, R$^{10}$, R$^{11}$ and R$^{12}$ are independently selected from hydrogen, in each case unsubstituted or substituted alkyl, alkoxy, alkylthio, (monoalkyl)amino, (dialkyl)amino, cycloalkyl, cycloalkoxy, cycloalkylthio, (monocycloalkyl)amino, (dicycloalkyl)amino, heterocycloalkyl, heterocycloalkoxy, heterocycloalkylthio, (monoheterocycloalkyl)amino, (diheterocycloalkyl)amino, aryl, aryloxy, arylthio, (monoaryl)amino, (diaryl)amino, hetaryl, hetaryloxy, hetarylthio, (monohetaryl)amino, (dihetaryl)amino, halogen, hydroxy, mercapto, cyano, nitro, cyanato, thiocyanato, formyl, acyl, carboxy, carboxylate, alkylcarbonyloxy, carbamoyl, alkylaminocarbonyl, dialkylaminocarbonyl, sulfo, sulfonate, sulfoamino, sulfamoyl, alkylsulfonyl, arylsulfonyl, amidino, NE$^1$E$^2$, where E$^1$ and E$^2$ are each independently hydrogen, alkyl, cycloalkyl, heterocycloalkyl, aryl or hetaryl, where in each case at least two adjacent radicals selected from the R$^5$, R$^6$, R$^7$, R$^8$, R$^9$, R$^{10}$R$^{11}$ and R$^{12}$ radicals, together with the carbon atoms of the benzene ring to which they are bonded, may also be a fused ring system having 1, 2, 3, 4, 5, 6, 7 or 8 further rings.

According to a further aspect of the present invention there is provided a process for the preparation of a compound of the formula I,

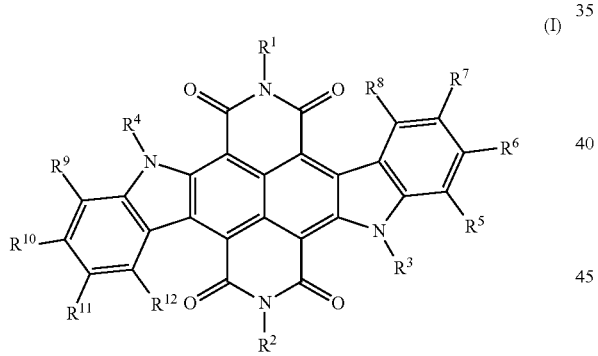
(I)

wherein

R$^1$ and R$^2$ are each independently selected from hydrogen and in each case unsubstituted or substituted alkyl, cycloalkyl, heterocycloalkyl, aryl and hetaryl, R$^3$ and R$^4$ are each independently selected from hydrogen and in each case unsubstituted or substituted alkyl, cycloalkyl, heterocycloalkyl, aryl and hetaryl, R$^5$, R$^6$, R$^7$, R$^8$, R$^9$, R$^{10}$, R$^{11}$ and R$^{12}$ are independently selected from hydrogen, in each case unsubstituted or substituted alkyl, alkoxy, alkylthio, (monoalkyl)amino, (dialkyl)amino, cycloalkyl, cycloalkoxy, cycloalkylthio, (monocycloalkyl)amino, (dicycloalkyl)amino, heterocycloalkyl, heterocycloalkoxy, heterocycloalkylthio, (monoheterocycloalkyl)amino, (diheterocycloalkyl)amino, aryl, aryloxy, arylthio, (monoaryl)amino, (diaryl)amino, hetaryl, hetaryloxy, hetarylthio, (monohetaryl)amino, (dihetaryl)amino, halogen, hydroxy, mercapto, cyano, nitro, cyanato, thiocyanato, formyl, acyl, carboxy, carboxylate, alkylcarbonyloxy, carbamoyl, alkylaminocarbonyl, dialkylaminocarbonyl, sulfo, sulfonate, sulfoamino, sulfamoyl, alkylsulfonyl, arylsulfonyl, amidino, NE$^1$E$^2$ where E$^1$ and E$^2$ are each independently hydrogen, alkyl, cycloalkyl, heterocycloalkyl, aryl or hetaryl, in which a 2,6-dibromonaphthalene-1,4,5,8-tetracarboxylic acid bisimide of the formula (II)

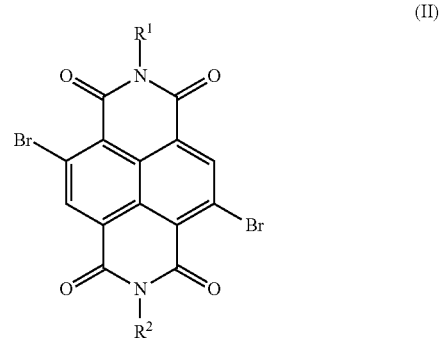
(II)

wherein

R$^1$ and R$^2$ have the afore-mentioned meaning, is subjected to a reaction with a compound of the formula (IIIa) and, optionally, a different compound of the formula (IIIb)

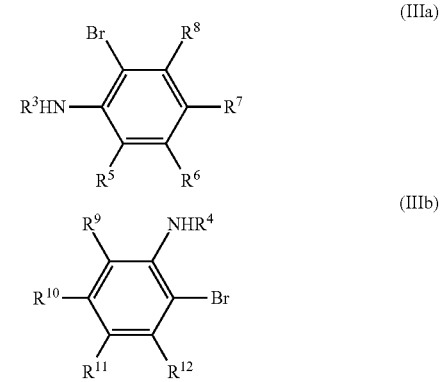

wherein

R$^3$, R$^4$, R$^5$, R$^6$, R$^7$, R$^8$, R$^9$, R$^{10}$, R$^{11}$ and R$^{12}$ have the afore-mentioned meaning.

According to a further aspect of the present invention there is provided an organic field-effect transistor comprising a substrate having at least one gate structure, a source electrode and a drain electrode and at least one compound of the formula I as defined above and in the following as a semiconductor material.

The compounds of the formula (I) can be in principle used as n-semiconductors or as p-semiconductors. If a compound of the formula (I) acts as n-semiconductor or as p-semiconductors depends inter alia on the employed gate dielectric. Gate dielectrics are usually employed in the form of a self-assembled monolayer (SAM) of suitable compounds, e.g. silanes with more or less electronegative substituents, alkyl phosphonic acid, fluoroalkyl phosphonic acid, etc. By choosing a certain SAM gate dielectric or a certain mixture of different SAM gate dielectrics, it is possible to control the properties of the semiconductor material. In electronic devices that employ a combination of two different semiconductors, e.g. organic solar cells, it depends on the corresponding semiconductor material if a compound of the formula (I) acts as n-semiconductor or as p-semiconductor.

According to a further aspect of the present invention there is provided a substrate comprising a plurality of organic field-effect transistors, at least some of the field-effect transistors comprising at least one compound of the formula I as defined above and in the following.

According to a further aspect of the present invention there is provided a semiconductor unit comprising at least one substrate comprising a plurality of organic field-effect transistors, at least some of the field-effect transistors comprising at least one compound of the formula I as defined above and in the following.

According to a further aspect of the present invention there is provided an electroluminescent arrangement comprising an upper electrode, a lower electrode, wherein at least one of said electrodes is transparent, an electroluminescent layer and optionally an auxiliary layer, wherein the electroluminescent arrangement comprises at least one compound of the formula I as defined above and in the following.

In a preferred embodiment, the electroluminescent arrangement is in form of an organic light-emitting diode (OLED).

According to a further aspect of the present invention there is provided an organic solar cell comprising at least one compound of the formula (I) as defined above and in the following.

According to a further aspect of the present invention there is provided the use of a compound of the general formula I, as defined above and in the following, as a semiconductor material.

In a preferred embodiment, the compound of the general formula I are used as a semiconductor material in organic electronics or in organic photovoltaics.

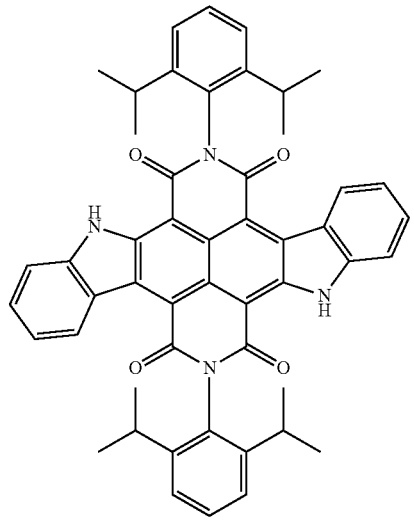

In combination with $C_{14}H_{29}PO(OH)_2$ the compound of formula (I) acts as n-semiconductor.

Figure 2:
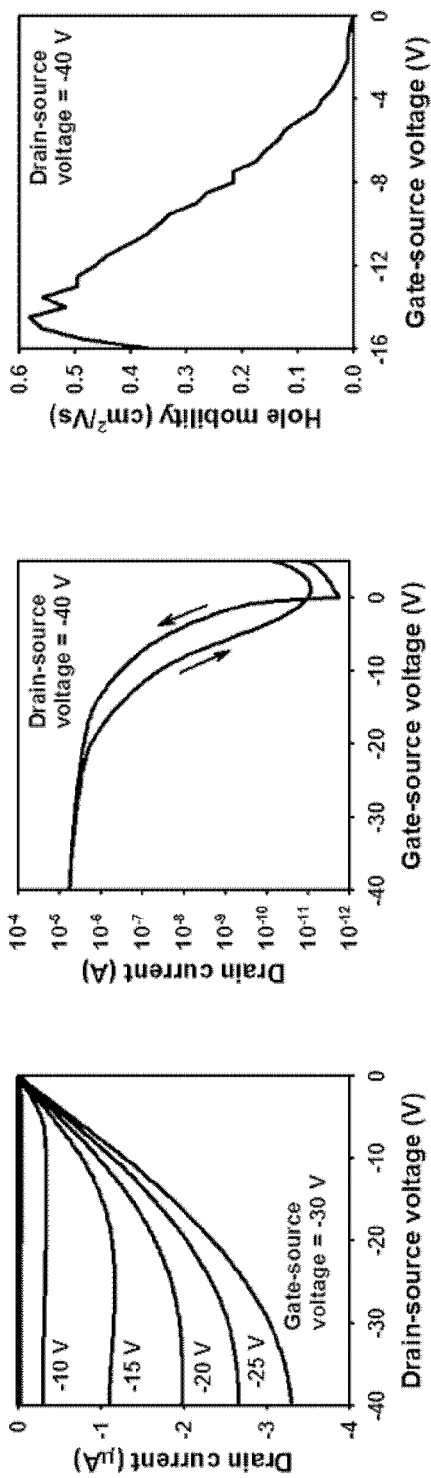

FIG. 2 shows the characteristic data of the TFT of example 2, substrate B with $C_7F_{15}C_{11}H_{22}PO(OH)_2$ as gate dielectric and the same semiconductor material as example 2, substrate A.

In combination with $C_7F_{15}C_{11}H_{22}PO(OH)_2$ the compound of formula (I) acts as p-semiconductor.

Figure 3:
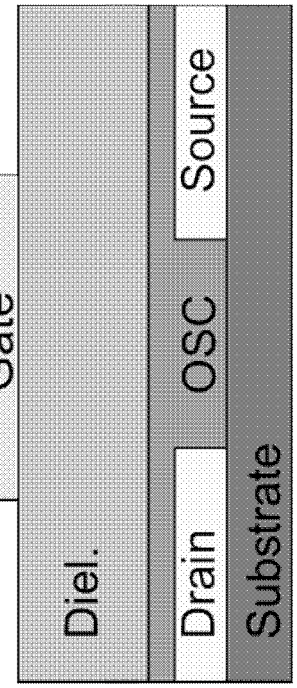

FIG. 3 shows preferred semiconductor architectures, in particular "Bottom Gate Top Contact", "Bottom Gate Bottom Contact", "Top Gate Bottom Contact" and "Top Gate Top Contact".

DETAILED DESCRIPTION OF THE INVENTION

The expression "halogen" denotes in each case fluorine, bromine, chlorine or iodine, particularly chlorine, bromide or iodine.

In the context of the invention, the expression "unsubstituted or substituted alkyl, cycloalkyl, heterocycloalkyl, aryl and hetaryl" represents unsubstituted or substituted alkyl, unsubstituted or substituted cycloalkyl, unsubstituted or substituted heterocycloalkyl, unsubstituted or substituted aryl and unsubstituted or substituted hetaryl.

In the context of the invention, the expression "unsubstituted or substituted alkyl, alkoxy, alkylthio, (monoalkyl) amino, (dialkyl)amino, cycloalkyl, cycloalkoxy, cycloalkylthio, (monocycloalkyl)amino, (dicycloalkyl)amino, heterocycloalkyl, heterocycloalkoxy, heterocycloalkylthio, (monoheterocycloalkyl)amino, (diheterocycloalkyl)amino, aryl, aryloxy, arylthio, (monoaryl)amino, (diaryl)amino, hetaryl, hetaryloxy, hetarylthio, (monohetaryl)amino and (dihetaryl)amino" represents unsubstituted or substituted alkyl, unsubstituted or substituted alkoxy, unsubstituted or substituted alkylthio, unsubstituted or substituted (monoalkyl) amino, unsubstituted or substituted (dialkyl)amino, unsubstituted or substituted cycloalkyl, unsubstituted or substituted cycloalkoxy, unsubstituted or substituted cycloalkylthio, unsubstituted or substituted (monocycloalkyl)amino, unsubstituted or substituted (dicycloalkyl) amino, unsubstituted or substituted heterocycloalkyl, unsubstituted or substituted heterocycloalkoxy, unsubstituted or substituted heterocycloalkylthio, unsubstituted or substituted (monoheterocycloalkyl)amino, unsubstituted or substituted (diheterocycloalkyl)amino, unsubstituted or substituted aryl, unsubstituted or substituted aryloxy, unsubstituted or substituted arylthio, unsubstituted or substituted (monoaryl)amino, unsubstituted or substituted (diaryl)amino, unsubstituted or substituted hetaryl, unsubstituted or substituted hetaryloxy, unsubstituted or substituted hetarylthio, unsubstituted or substituted (monohetaryl) amino and unsubstituted or substituted (dihetaryl)amino.

In the context of the present invention, the expression "alkyl" comprises straight-chain or branched alkyl groups. Alkyl is preferably $C_1$-$C_{30}$-alkyl, more preferably $C_1$-$C_{20}$-alkyl and most preferably $C_1$-$C_{12}$-alkyl. Examples of alkyl groups are especially methyl, ethyl, n-propyl, isopropyl, n-butyl, isobutyl, sec-butyl, tert-butyl, n-pentyl, neo-pentyl, n-hexyl, n-heptyl, n-octyl, n-nonyl, n-decyl, n-undecyl, n-dodecyl, n-tridecyl, n-tetradecyl, n-hexadecyl, n-octadecyl and n-eicosyl.

The expression alkyl also comprises alkyl radicals whose carbon chains may be interrupted by one or more nonadjacent groups which are selected from —O—, —S—, —NR$^b$—, —C(=O)—, —S(=O)— and/or —S(=O)$_2$—. R$^b$ is preferably hydrogen, alkyl, cycloalkyl, heterocycloalkyl, aryl or hetaryl.

Substituted alkyl groups may, depending on the length of the alkyl chain, have one or more (e.g. 1, 2, 3, 4, 5 or more than 5) substituents. These are preferably each independently selected from cycloalkyl, heterocycloalkyl, aryl, hetaryl, fluorine, chlorine, bromine, hydroxyl, mercapto, cyano, nitro, nitroso, formyl, acyl, COOH, carboxylate, alkylcarbonyloxy, carbamoyl, SO$_3$H, sulfonate, sulfamino, sulfamide, amidino, NE$^1$E$^2$ where E$^1$ and E$^2$ are each independently hydrogen, alkyl, cycloalkyl, heterocycloalkyl, aryl or hetaryl. Cycloalkyl, heterocycloalkyl, aryl and hetaryl substituents of the alkyl groups may in turn be unsubstituted or substituted; suitable substituents are the substituents mentioned below for these groups.

Carboxylate and sulfonate respectively represent a derivative of a carboxylic acid function and a sulfonic acid function, especially a metal carboxylate or sulfonate, a carboxylic ester or sulfonic ester function or a carboxamide or sulfonamide function. Such derivatives include, for example, esters with C$_1$-C$_4$-alkanols, such as methanol, ethanol, n-propanol, isopropanol, n-butanol, sec-butanol and tert-butanol.

The above remarks regarding alkyl also apply to the alkyl moiety in alkoxy, alkylthio (=alkylsulfanyl), monoalkylamino and dialkylamino.

Alkylene represents a linear saturated hydrocarbon chain having from 1 to 10 and especially from 1 to 4 carbon atoms, such as ethane-1,2-diyl, propane-1,3-diyl, butane-1,4-diyl, pentane-1,5-diyl or hexane-1,6-diyl.

In the context of the present invention, the term "cycloalkyl" denotes a mono-, bi- or tricyclic hydrocarbon radical having usually from 3 to 20, preferably 3 to 12, more preferably 5 to 12, carbon atoms such as cyclopropyl, cyclobutyl, cyclopentyl, cyclohexyl, cycloheptyl, cyclooctyl, cyclododecyl, cyclopentadecyl, norbornyl, bicyclo[2.2.2]octyl or adamantyl.

Substituted cycloalkyl groups may, depending on the ring size, have one or more (e.g. 1, 2, 3, 4, 5 or more than 5) substituents. These are preferably each independently selected from alkyl, alkoxy, alkylthio, cycloalkyl, heterocycloalkyl, aryl, hetaryl, fluorine, chlorine, bromine, hydroxyl, mercapto, cyano, nitro, nitroso, formyl, acyl, COOH, carboxylate, alkylcarbonyloxy, carbamoyl, SO$_3$H, sulfonate, sulfamino, sulfamide, amidino, NE$^3$E$^4$ where E$^3$ and E$^4$ are each independently hydrogen, alkyl, cycloalkyl, heterocycloalkyl, aryl or hetaryl. In the case of substitution, the cycloalkyl groups preferably bear one or more, for example one, two, three, four or five, C$_1$-C$_6$-alkyl groups. Examples of substituted cycloalkyl groups are especially 2- and 3-methyl-cyclopentyl, 2- and 3-ethylcyclopentyl, 2-, 3- and 4-methylcyclohexyl, 2-, 3- and 4-ethylcyclohexyl, 2-, 3- and 4-propylcyclohexyl, 2-, 3- and 4-isopropylcyclohexyl, 2-, 3- and 4-butylcyclohexyl, 2-, 3- and 4-sec.-butylcyclohexyl, 2-, 3- and 4-tert-butylcyclohexyl, 2-, 3- and 4-methylcycloheptyl, 2-, 3- and 4-ethylcycloheptyl, 2-, 3- and 4-propylcycloheptyl, 2-, 3- and 4-isopropylcycloheptyl, 2-, 3- and 4-butylcycloheptyl, 2-, 3- and 4-sec-butylcycloheptyl, 2-, 3- and 4-tert-butylcycloheptyl, 2-, 3-, 4- and 5-methylcyclooctyl, 2-, 3-, 4- and 5-ethylcyclooctyl, 2-, 3-, 4- and 5-propylcyclooctyl.

The above remarks regarding cycloalkyl also apply to the cycloalkyl moiety in cycloalkoxy, cycloalkylthio (=cycloalkylsulfanyl), monocycloalkylamino and dicycloalkylamino.

In the context of the present invention, the term "aryl" refers to mono- or polycyclic aromatic hydrocarbon radicals. Aryl usually is an aromatic radical having 6 to 24 carbon atoms, preferably 6 to 20 carbon atoms, especially 6 to 14 carbon atoms as ring members. Aryl is preferably phenyl, naphthyl, indenyl, fluorenyl, anthracenyl, phenanthrenyl, naphthacenyl, chrysenyl, pyrenyl, coronenyl, perylenyl, etc., and more preferably phenyl or naphthyl.

Substituted aryls may, depending on the number and size of their ring systems, have one or more (e.g. 1, 2, 3, 4, 5 or more than 5) substituents. These are preferably each independently selected from alkyl, alkoxy, alkylthio, cycloalkyl, heterocycloalkyl, aryl, hetaryl, fluorine, chlorine, bromine, hydroxyl, mercapto, cyano, nitro, nitroso, formyl, acyl, COOH, carboxylate, alkylcarbonyloxy, carbamoyl, SO$_3$H, sulfonate, sulfamino, sulfamide, amidino, NE$^5$E$^6$ where E$^5$ and E$^6$ are each independently hydrogen, alkyl, cycloalkyl, heterocycloalkyl, aryl or hetaryl. The alkyl, alkoxy, alkylamino, alkylthio, cycloalkyl, heterocycloalkyl, aryl and hetaryl substituents on the aryl may in turn be unsubstituted or substituted. Reference is made to the substituents mentioned above for these groups. The substituents on the aryl are preferably selected from alkyl, alkoxy, haloalkyl, haloalkoxy, aryl, fluorine, chlorine, bromine, cyano and nitro. Substituted aryl is more preferably substituted phenyl which generally bears 1, 2, 3, 4 or 5, preferably 1, 2 or 3, substituents.

Substituted aryl is preferably aryl substituted by at least one alkyl group ("alkaryl", also referred to hereinafter as alkylaryl). Alkaryl groups may, depending on the size of the aromatic ring system, have one or more (e.g. 1, 2, 3, 4, 5, 6, 7, 8, 9 or more than 9) alkyl substituents. The alkyl substituents may be unsubstituted or substituted. In this regard, reference is made to the above statements regarding unsubstituted and substituted alkyl. In a preferred embodiment, the alkaryl groups have exclusively unsubstituted alkyl substituents. Alkaryl is preferably phenyl which bears 1, 2, 3, 4 or 5, preferably 1, 2 or 3, more preferably 1 or 2, alkyl substituents.

Aryl which bears one or more radicals is, for example, 2-, 3- and 4-methylphenyl, 2,4-, 2,5-, 3,5- and 2,6-dimethylphenyl, 2,4,6-trimethylphenyl, 2-, 3- and 4-ethylphenyl, 2,4-, 2,5-, 3,5- and 2,6-diethylphenyl, 2,4,6-triethylphenyl, 2-, 3- and 4-propylphenyl, 2,4-, 2,5-, 3,5- and 2,6-dipropylphenyl, 2,4,6-tripropylphenyl, 2-, 3- and 4-isopropylphenyl, 2,4-, 2,5-, 3,5- and 2,6-diisopropylphenyl, 2,4,6-triisopropylphenyl, 2-, 3- and 4-butylphenyl, 2,4-, 2,5-, 3,5- and 2,6-dibutylphenyl, 2,4,6-tributylphenyl, 2-, 3- and 4-isobutylphenyl, 2,4-, 2,5-, 3,5- and 2,6-diisobutylphenyl, 2,4,6-triisobutylphenyl, 2-, 3- and 4-sec-butylphenyl, 2,4-, 2,5-, 3,5- and 2,6-di-sec-butylphenyl, 2,4,6-tri-sec-butylphenyl, 2-, 3- and 4-tert-butylphenyl, 2,4-, 2,5-, 3,5- and 2,6-di-tert-butylphenyl and 2,4,6-tri-tert-butylphenyl; 2-, 3- and 4-methoxyphenyl, 2,4-, 2,5-, 3,5- and 2,6-dimethoxyphenyl, 2,4,6-trimethoxyphenyl, 2-, 3- and 4-ethoxyphenyl, 2,4-, 2,5-, 3,5- and 2,6-diethoxyphenyl, 2,4,6-triethoxyphenyl, 2-, 3- and 4-propoxyphenyl, 2,4-, 2,5-, 3,5- and 2,6-dipropoxyphenyl, 2-, 3- and 4-isopropoxyphenyl, 2,4-, 2,5-, 3,5- and 2,6-diisopropoxyphenyl and 2-, 3- and 4-butoxyphenyl; 2-, 3- and 4-chlorophenyl, (2-chloro-6-methyl)phenyl, (2-chloro-6-ethyl)phenyl, (4-chloro-6-methyl)phenyl, (4-chloro-6-ethyl)phenyl.

The above remarks regarding aryl also apply to the aryl moiety in aryloxy, arylthio (=arylsulfanyl), monoarylamino and diarylamino.

In the context of the present invention, the expression "heterocycloalkyl" comprises nonaromatic, unsaturated or fully saturated, cycloaliphatic groups having generally 5 to 8 ring atoms, preferably 5 or 6 ring atoms. In the heterocycloalkyl groups, compared to the corresponding cycloalkyl groups, 1, 2, 3, 4 or more than 4 of the ring carbon atoms are replaced by heteroatoms or heteroatom-containing groups. The heteroatoms or heteroatom-containing groups are preferably selected from —O—, —S—, —NR$^e$—, —C(=O)—, —S(=O)— and/or —S(=O)$_2$—. R$^e$ is preferably hydrogen, alkyl, cycloalkyl, heterocycloalkyl, aryl or hetaryl. Heterocycloalkyl is unsubstituted or optionally bears one or more, e.g. 1, 2, 3, 4, 5, 6 or 7, identical or different radicals. These are preferably each independently selected from alkyl, alkoxy, alkylamino, alkylthio, cycloalkyl, heterocycloalkyl, aryl, hetaryl, fluorine, chlorine, bromine, hydroxyl, mercapto, cyano, nitro, nitroso, formyl, acyl, COOH, carboxylate, alkylcarbonyloxy, carbamoyl, SO$_3$H, sulfonate, sulfamino, sulfamide, amidino, NE$^5$E$^6$ where E$^5$ and E$^6$ are each independently hydrogen, alkyl, cycloalkyl, heterocycloalkyl, aryl or hetaryl. Examples of heterocycloalkyl groups are especially pyrrolidinyl, piperidinyl, 2,2,6,6-tetramethylpiperidinyl, imidazolidinyl, pyrazolidinyl, oxazolidinyl, morpholinyl, thiazolidinyl, isothiazolidinyl, isoxazolidinyl, piperazinyl, tetrahydrothiophenyl, dihydrothien-2-yl, tetrahydrofuranyl, dihydrofuran-2-yl, tetrahydropyranyl, 2-oxazolinyl, 3-oxazolinyl, 4-oxazolinyl and dioxanyl.

Substituted heterocycloalkyl groups may, depending on the ring size, have one or more (e.g. 1, 2, 3, 4, 5 or more than 5) substituents. These are preferably each independently selected from alkyl, alkoxy, alkylthio, cycloalkyl, heterocycloalkyl, aryl, hetaryl, fluorine, chlorine, bromine, hydroxyl, mercapto, cyano, nitro, nitroso, formyl, acyl, COOH, carboxylate, alkylcarbonyloxy, carbamoyl, SO$_3$H, sulfonate, sulfamino, sulfamide, amidino, NE$^7$E$^8$ where E$^7$ and E$^8$ are each independently hydrogen, alkyl, cycloalkyl, heterocycloalkyl, aryl or hetaryl. In the case of substitution, the heterocycloalkyl groups preferably bear one or more, for example one, two, three, four or five, C$_1$-C$_6$-alkyl groups.

The above remarks regarding heterocycloalkyl also apply to the heterocycloalkyl moiety in heterocycloalkoxy, heterocycloalkylthio (=heterocycloalkylsulfanyl), monoheterocycloalkylamino and diheterocycloalkylamino.

In the context of the present invention, the expression "hetaryl" (heteroaryl) comprises heteroaromatic, mono- or polycyclic groups. In addition to the ring carbon atoms, these have 1, 2, 3, 4 or more than 4 heteroatoms as ring members. The heteroatoms are preferably selected from oxygen, nitrogen, selenium and sulfur. The hetaryl groups have preferably 5 to 18, e.g. 5, 6, 8, 9, 10, 11, 12, 13 or 14, ring atoms.

Monocyclic hetaryl groups are preferably 5- or 6-membered hetaryl groups, such as 2-furyl (furan-2-yl), 3-furyl (furan-3-yl), 2-thienyl (thiophen-2-yl), 3-thienyl (thiophen-3-yl), selenophen-2-yl, selenophen-3-yl, 1H-pyrrol-2-yl, 1H-pyrrol-3-yl, pyrrol-1-yl, imidazol-2-yl, imidazol-1-yl, imidazol-4-yl, pyrazol-1-yl, pyrazol-3-yl, pyrazol-4-yl, pyrazol-5-yl, 3-isoxazolyl, 4-isoxazolyl, 5-isoxazolyl, 3-isothiazolyl, 4-isothiazolyl, 5-isothiazolyl, 2-oxazolyl, 4-oxazolyl, 5-oxazolyl, 2-thiazolyl, 4-thiazolyl, 5-thiazolyl, 1,2,4-oxadiazol-3-yl, 1,2,4-oxadiazol-5-yl, 1,3,4-oxadiazol-2-yl, 1,2,4-thiadiazol-3-yl, 1,2,4-thiadiazol-5-yl, 1,3,4-thiadiazol-2-yl, 4H-[1,2,4]-triazol-3-yl, 1,3,4-triazol-2-yl, 1,2,3-triazol-1-yl, 1,2,4-triazol-1-yl, pyridin-2-yl, pyridin-3-yl, pyridin-4-yl, 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl.

Polycyclic hetaryl groups have 2, 3, 4 or more than 4 fused rings. The fused-on rings may be aromatic, saturated or partly unsaturated. Examples of polycyclic hetaryl groups are quinolinyl, isoquinolinyl, indolyl, isoindolyl, indolizinyl, benzofuranyl, isobenzofuranyl, benzothiophenyl, benzoxazolyl, benzisoxazolyl, benzthiazolyl, benzoxadiazolyl, benzothiadiazolyl, benzoxazinyl, benzopyrazolyl, benzimidazolyl, benzotriazolyl, benzotriazinyl, benzoselenophenyl, thienothiophenyl, thienopyrimidyl, thiazolothiazolyl, dibenzopyrrolyl (carbazolyl), dibenzofuranyl, dibenzothiophenyl, naphtho[2,3-b]thiophenyl, naphtha[2,3-b]furyl, dihydroindolyl, dihydroindolizinyl, dihydroisoindolyl, dihydroquinolinyl and dihydroisoquinolinyl.

Substituted hetaryl groups may, depending on the number and size of their ring systems, have one or more (e.g. 1, 2, 3, 4, 5 or more than 5) substituents. These are preferably each independently selected from alkyl, alkoxy, alkylthio, cycloalkyl, heterocycloalkyl, aryl, hetaryl, fluorine, chlorine, bromine, hydroxyl, mercapto, cyano, nitro, nitroso, formyl, acyl, COOH, carboxylate, alkylcarbonyloxy, carbamoyl, SO$_3$H, sulfonate, sulfamino, sulfamide, amidino, NE$^9$E$^{10}$ where E$^9$ and E$^{10}$ are each independently hydrogen, alkyl, cycloalkyl, heterocycloalkyl, aryl or hetaryl. Halogen substituents are preferably fluorine, chlorine or bromine. The substituents are preferably selected from C$_1$-C$_6$-alkyl, C$_1$-C$_6$-alkoxy, hydroxyl, carboxyl, halogen and cyano.

The above remarks regarding hetaryl also apply to the hetaryl moiety in hetaryloxy, hetarylthio, monohetarylamino and dihetarylamino.

For the purposes of the present invention, the expression "acyl" refers to alkanoyl or aroyl groups which generally have from 2 to 11, preferably from 2 to 8, carbon atoms, for example the acetyl, propanoyl, butanoyl, pentanoyl, hexanoyl, heptanoyl-, 2-ethyl-hexanoyl, 2-propylheptanoyl, pivaloyl, benzoyl or naphthoyl group.

The groups NE$^1$E$^2$ are preferably N,N-dimethylamino, N,N-diethylamino, N,N-dipropylamino, N,N-diisopropylamino, N,N-di-n-butylamino, N,N-di-t-butylamino, N,N-dicyclohexylamino or N,N-diphenylamino.

Fused ring systems can comprise alicyclic, aliphatic heterocyclic, aromatic and heteroaromatic rings and combinations thereof, hydroaromatic joined by fusion. Fused ring systems comprise two, three or more (e.g. 4, 5, 6, 7 or 8) rings. Depending on the way in which the rings in fused ring systems are joined, a distinction is made between ortho-fusion, i.e. each ring shares at least one edge or two atoms with each adjacent ring, and peri-fusion in which a carbon atom belongs to more than two rings. Preferred fused ring systems are ortho-fused ring systems.

Specific examples of the radicals mentioned in the following formulae and their substituents are:

methyl, ethyl, propyl, isopropyl, butyl, isobutyl, tert-butyl, pentyl, isopentyl, neopentyl, tert-pentyl, hexyl, 2-methylpentyl, heptyl, 1-ethylpentyl, octyl, 2-ethylhexyl, isooctyl, nonyl, isononyl, decyl, isodecyl, undecyl, dodecyl, tridecyl, isotridecyl, tetradecyl, pentadecyl, hexadecyl, heptadecyl, octadecyl, nonadecyl and eicosyl (the above terms isooctyl, isononyl, isodecyl and isotridecyl are trivial terms and stem from the alcohols obtained by the oxo process);

2-methoxyethyl, 2-ethoxyethyl, 2-propoxyethyl, 2-isopropoxyethyl, 2-butoxyethyl, 1- and 3-methoxypropyl, 2- and 3-ethoxypropyl, 2- and 3-propoxypropyl, 2- and 3-butoxypropyl, 2- and 4-methoxybutyl, 2- and 4-ethoxybutyl, 2- and 4-propoxybutyl, 3,6-dioxaheptyl, 3,6-dioxaoctyl, 4,8-dioxanonyl, 3,7-dioxaoctyl, 3,7-dioxanonyl, 4,7-dioxaoctyl, 4,7-dioxanonyl, 2- and 4-butoxybutyl, 4,8-dioxadecyl, 3,6, 9-trioxadecyl, 3,6,9-trioxaundecyl, 3,6,9-trioxadodecyl, 3,6,9,12-tetraoxamidecyl and 3,6,9,12-tetra-oxatetradecyl;

2-methylthioethyl, 2-ethylthioethyl, 2-propylthioethyl, 2-isopropylthioethyl, 2-butylthioethyl, 2- and 3-methylthiopropyl, 2- and 3-ethylthiopropyl, 2- and 3-propylthiopropyl, 2- and 3-butylthiopropyl, 2- and 4-methylthiobutyl, 2- and 4-ethyl-thiobutyl, 2- and 4-propylthiobutyl, 3,6-dithiaheptyl, 3,6-dithiaoctyl, 4,8-dithianonyl, 3,7-dithiaoctyl, 3,7-dithianonyl, 2- and 4-butylthiobutyl, 4,8-dithiadecyl, 3,6,9-tri-thiadecyl, 3,6,9-trithiaundecyl, 3,6,9-trithiadodecyl, 3,6,9,12-tetrathiamidecyl and 3,6,9,12-tetrathiatetradecyl;

2-monomethyl- and 2-monoethylaminoethyl, 2-dimethylaminoethyl, 2- and 3-dimethyl-aminopropyl, 3-monoisopropylaminopropyl, 2- and 4-monopropylaminobutyl, 2- and 4-dimethylaminobutyl, 6-methyl-3,6-diazaheptyl, 3,6-dimethyl-3,6-diazaheptyl, 3,6-diazaoctyl, 3,6-dimethyl-3,6-diazaoctyl, 9-methyl-3,6,9-triazadecyl, 3,6,9-trimethyl-3,6,9-triazadecyl, 3,6,9-triazaundecyl, 3,6,9-trimethyl-3,6,9-triazaundecyl, 12-methyl-3,6,9,12-tetraazamidecyl and 3,6,9,12-tetramethyl-3,6,9,12-tetraazamidecyl;

(1-ethylethylidene)aminoethylene, (1-ethylethylidene)aminopropylene, (1-ethylethylidene)aminobutylene, (1-ethylethylidene)aminodecylene and (1-ethylethylidene)aminododecylene;

propan-2-on-1-yl, butan-3-on-1-yl, butan-3-on-2-yl and 2-ethylpentan-3-on-1-yl;

2-methylsulfoxidoethyl, 2-ethylsulfoxidoethyl, 2-propylsulfoxidoethyl, 2-isopropylsulf-oxidoethyl, 2-butylsulfoxidoethyl, 2- and 3-methylsulfoxidopropyl, 2- and 3-ethylsulfoxidopropyl, 2- and 3-propylsulfoxidopropyl, 2- and 3-butylsulfoxidopropyl, 2- and 4-methylsulfoxidobutyl, 2- and 4-ethylsulfoxidobutyl, 2- and 4-propylsulfoxidobutyl and 4-butylsulfoxidobutyl;

2-methylsulfonylethyl, 2-ethylsulfonylethyl, 2-propylsulfonylethyl, 2-isopropylsulfonyl-ethyl, 2-butylsulfonylethyl, 2- and 3-methylsulfonylpropyl, 2- and 3-ethylsulfonylpropyl, 2- and 3-propylsulfonylpropyl, 2- and 3-butylsulfonylpropyl, 2- and 4-methylsulfonyl-butyl, 2- and 4-ethylsulfonylbutyl, 2- and 4-propylsulfonylbutyl and 4-butylsulfonylbutyl;

carboxymethyl, 2-carboxyethyl, 3-carboxypropyl, 4-carboxybutyl, 5-carboxypentyl, 6-carboxyhexyl, 8-carboxyoctyl, 10-carboxydecyl, 12-carboxydodecyl and 14-carboxytetradecyl;

sulfomethyl, 2-sulfoethyl, 3-sulfopropyl, 4-sulfobutyl, 5-sulfopentyl, 6-sulfohexyl, 8-sulfooctyl, 10-sulfodecyl, 12-sulfododecyl and 14-sulfotetradecyl;

2-hydroxyethyl, 2- and 3-hydroxypropyl, 1-hydroxyprop-2-yl, 3- and 4-hydroxybutyl, 1-hydroxybut-2-yl and 8-hydroxy-4-oxaoctyl;

2-cyanoethyl, 3-cyanopropyl, 3- and 4-cyanobutyl, 2-methyl-3-ethyl-3-cyanopropyl, 7-cyano-7-ethylheptyl and 4,7-dimethyl-7-cyanoheptyl;

2-chloroethyl, 2- and 3-chloropropyl, 2-, 3- and 4-chlorobutyl, 2-bromoethyl, 2- and 3-bromopropyl and 2-, 3- and 4-bromobutyl;

2-nitroethyl, 2- and 3-nitropropyl and 2-, 3- and 4-nitrobutyl;

methoxy, ethoxy, propoxy, isopropoxy, butoxy, isobutoxy, sec-butoxy, tert-butoxy, pentoxy, isopentoxy, neopentoxy, tert-pentoxy and hexoxy;

methylthio, ethylthio, propylthio, isopropylthio, butylthio, isobutylthio, sec-butylthio, tert-butylthio, pentylthio, isopentylthio, neopentylthio, tert-pentylthio and hexylthio;

ethynyl, 1- and 2-propynyl, 1-, 2- and 3-butynyl, 1-, 2-, 3- and 4-pentynyl, 1-, 2-, 3-, 4- and 5-hexynyl, 1-, 2-, 3-, 4-, 5-, 6-, 7-, 8- and 9-decynyl, 1-, 2-, 3-, 4-, 5-, 6-, 7-, 8-, 9-, 10- and 11-dodecynyl and 1-, 2-, 3-, 4-, 5-, 6-, 7-, 8-, 9-, 10-, 11-, 12-, 13-, 14-, 15-, 16- and 17-octadecynyl;

ethenyl, 1- and 2-propenyl, 1-, 2- and 3-butenyl, 1-, 2-, 3- and 4-pentenyl, 1-, 2-, 3-, 4- and 5-hexenyl, 1-, 2-, 3-, 4-, 5-, 6-, 7-, 8- and 9-decenyl, 1-, 2-, 3-, 4-, 5-, 6-, 7-, 8-, 9-, 10- and 11-dodecenyl and 1-, 2-, 3-, 4-, 5-, 6-, 7-, 8-, 9-, 10-, 11-, 12-, 13-, 14-, 15-, 16- and 17-octadecenyl;

methylamino, ethylamino, propylamino, isopropylamino, butylamino, isobutylamino, pentylamino, hexylamino, dimethylamino, methylethylamino, diethylamino, dipropylamino, diisopropylamino, dibutylamino, diisobutylamino, dipentylamino, dihexylamino, dicyclopentylamino, dicyclohexylamino, dicycloheptylamino, diphenylamino and dibenzylamino;

formylamino, acetylamino, propionylamino and benzoylamino;

carbamoyl, methylaminocarbonyl, ethylaminocarbonyl, propylaminocarbonyl, butylaminocarbonyl, pentylaminocarbonyl, hexylaminocarbonyl, heptylaminocarbonyl, octylaminocarbonyl, nonylaminocarbonyl, decylaminocarbonyl and phenylaminocarbonyl;

aminosulfonyl, N,N-dimethylaminosulfonyl, N,N-diethylaminosulfonyl, N-methyl-N-ethylaminosulfonyl, N-methyl-N-dodecylaminosulfonyl, N-dodecylaminosulfonyl, (N,N-dimethylamino)ethylaminosulfonyl, N,N-(propoxyethyl)dodecylaminosulfonyl, N,N-diphenylaminosulfonyl, N,N-(4-tert-butylphenyl)octadecylaminosulfonyl and N,N-bis(4-chlorophenyl)aminosulfonyl;

methoxycarbonyl, ethoxycarbonyl, propoxycarbonyl, isopropoxycarbonyl, hexoxycarbonyl, dodecyloxycarbonyl, octadecyloxycarbonyl, phenoxycarbonyl, (4-tert-butylphenoxy)carbonyl and (4-chlorophenoxy)carbonyl;

methoxysulfonyl, ethoxysulfonyl, propoxysulfonyl, isopropoxysulfonyl, butoxysulfonyl, isobutoxysulfonyl, tert-butoxysulfonyl, hexoxysulfonyl, dodecyloxysulfonyl, octadecyloxysulfonyl, phenoxysulfonyl, 1- and 2-naphthyloxysulfonyl, (4-tert_butylphenoxy)sulfonyl and (4-chlorophenoxy)sulfonyl;

diphenylphosphino, di(o-tolyl)phosphino and diphenylphosphinoxido;

fluorine, chlorine, bromine and iodine;

phenylazo, 2-naphthylazo, 2-pyridylazo and 2-pyrimidylazo;

cyclopropyl, cyclobutyl, cyclopentyl, 2- and 3-methylcyclopentyl, 2- and 3-ethylcyclopentyl, cyclohexyl, 2-, 3- and 4-methylcyclohexyl, 2-, 3- and 4-ethylcyclohexyl, 3- and 4-propylcyclohexyl, 3- and 4-isopropylcyclohexyl, 3- and 4-butylcyclohexyl, 3- and 4-sec-butylcyclohexyl, 3- and 4-tert-butylcyclohexyl, cycloheptyl, 2-, 3- and 4-methylcycloheptyl, 2-, 3- and 4-ethylcycloheptyl, 3- and 4-propylcycloheptyl, 3- and 4-isopropylcycloheptyl, 3- and 4-butylcycloheptyl, 3- and 4-sec-butylcycloheptyl, 3- and 4-tert-butylcycloheptyl, cyclooctyl, 2-, 3-, 4- and 5-methylcyclooctyl, 2-, 3-, 4- and 5-ethylcyclooctyl and 3-, 4- and 5-propylcyclooctyl; 3- and 4-hydroxycyclohexyl, 3- and 4-nitrocyclohexyl and 3- and 4-chlorocyclohexyl;

1-, 2- and 3-cyclopentenyl, 1-, 2-, 3- and 4-cyclohexenyl, 1-, 2- and 3-cycloheptenyl and 1-, 2-, 3- and 4-cyclooctenyl;

2-dioxanyl, 1-morpholinyl, 1-thiomorpholinyl, 2- and 3-tetrahydrofuryl, 1-, 2- and 3-pyrrolidinyl, 1-piperazyl, 1-diketopiperazyl and 1-, 2-, 3- and 4-piperidyl;

phenyl, 2-naphthyl, 2- and 3-pyrryl, 2-, 3- and 4-pyridyl, 2-, 4- and 5-pyrimidyl, 3-, 4- and 5-pyrazolyl, 2-, 4- and 5-imidazolyl, 2-, 4- and 5-thiazolyl, 3-(1,2,4-triazyl), 2-(1,3,5-triazyl), 6-quinaldyl, 3-, 5-, 6- and 8-quinolinyl, 2-benzoxazolyl, 2-benzothiazolyl, 5-benzothiadiazolyl, 2- and 5-benzimidazolyl and 1- and 5-isoquinolyl;

1-, 2-, 3-, 4-, 5-, 6- and 7-indolyl, 1-, 2-, 3-, 4-, 5-, 6- and 7-isoindolyl, 5-(4-methyliso-indolyl), 5-(4-phenylisoindolyl), 1-, 2-, 4-, 6-, 7- and 8-(1,2,3,4-tetrahydroisoquinolinyl), 3-(5-phenyl)-(1,2,3,4-tetrahydroisoquinolinyl), 5-(3-dodecyl)-(1,2,3,4-tetrahydroisoquinolinyl), 1-, 2-, 3-, 4-, 5-, 6-, 7- and 8-(1,2,3,4-tetrahydroquinolinyl) and 2-, 3-, 4-, 5-, 6-, 7- and 8-chromanyl, 2-, 4- and 7-quinolinyl, 2-(4-phenylquinolinyl) and 2-(5-ethyl-quinolinyl);

2-, 3- and 4-methylphenyl, 2,4-, 3,5- and 2,6-dimethylphenyl, 2,4,6-trimethylphenyl, 2-, 3- and 4-ethylphenyl, 2,4-, 3,5- and 2,6-diethylphenyl, 2,4,6-triethylphenyl, 2-, 3- and 4-propylphenyl, 2,4-, 3,5- and 2,6-dipropylphenyl, 2,4,6-tripropylphenyl, 2-, 3- and 4-isopropylphenyl, 2,4-, 3,5- and 2,6-diisopropylphenyl, 2,4,6-triisopropylphenyl, 2-, 3- and 4-butylphenyl, 2,4-, 3,5- and 2,6-dibutylphenyl, 2,4,6-tributylphenyl, 2-, 3- and 4-isobutylphenyl, 2,4-, 3,5- and 2,6-diisobutylphenyl, 2,4,6-triisobutylphenyl, 2-, 3- and 4-sec-butylphenyl, 2,4-, 3,5- and 2,6-di-sec-butylphenyl and 2,4,6-tri-sec-butylphenyl; 2-, 3- and 4-methoxyphenyl, 2,4-, 3,5- and 2,6-dimethoxyphenyl, 2,4,6-trimethoxyphenyl, 2-, 3- and 4-ethoxyphenyl, 2,4-, 3,5- and 2,6-diethoxyphenyl, 2,4,6-triethoxyphenyl, 2-, 3- and 4-propoxyphenyl, 2,4-, 3,5- and 2,6-dipropoxyphenyl, 2-, 3- and 4-isopropoxyphenyl, 2,4- and 2,6-diisopropoxyphenyl and 2-, 3- and 4-butoxyphenyl; 2-, 3- and 4-chlorophenyl and 2,4-, 3,5- and 2,6-dichlorophenyl; 2-, 3- and 4-hydroxy-phenyl and 2,4-, 3,5- and 2,6-dihydroxyphenyl; 2-, 3- and 4-cyanophenyl; 3- and 4-carboxyphenyl; 3- and 4-carboxamidophenyl, 3- and 4-N-methylcarboxamidophenyl and 3- and 4-N-ethylcarboxamidophenyl; 3- and 4-acetylaminophenyl, 3- and 4-propionylaminophenyl and 3- and 4-butyrylaminophenyl; 3- and 4-N-phenylamino-phenyl, 3- and 4-N-(o-tolyl)aminophenyl, 3- and 4-N-(m-tolyl)aminophenyl and 3- and 4-(p-tolyl)aminophenyl; 3- and 4-(2-pyridyl)aminophenyl, 3- and 4-(3-pyridyl)aminophenyl, 3- and 4-(4-pyridyl)aminophenyl, 3- and 4-(2-pyrimidyl)aminophenyl and 4-(4-pyrimidyl)aminophenyl;

4-phenylazophenyl, 4-(1-naphthylazo)phenyl, 4-(2-naphthylazo)phenyl, 4-(4-naphthyl-azo)phenyl, 4-(2-pyridylazo)phenyl, 4-(3-pyridylazo)phenyl, 4-(4-pyridylazo)phenyl, 4-(2-pyrimidylazo)phenyl, 4-(4-pyrimidylazo)phenyl and 4-(5-pyrimidylazo)phenyl;

phenoxy, phenylthio, 2-naphthoxy, 2-naphthylthio, 2-, 3- and 4-pyridyloxy, 2-, 3- and 4-pyridylthio, 2-, 4- and 5-pyrimidyloxy and 2-, 4- and 5-pyrimidylthio.

Specific examples of radicals containing fluorine are the following:

2,2,2-trifluoroethyl, 2,2,3,3,3-pentafluoropropyl, 2,2-difluoroethyl, 2,2,2-trifluoro-1-phenylethylamin, 1-benzyl-2,2,2-trifluoroethyl, 2-bromo-2,2-difluoroethyl, 2,2,2-trifluoro-1-pyridin-2-ylethyl, 2,2-difluoropropyl, 2,2,2-trifluoro-1-(4-methoxyphenyl)ethylamin, 2,2,2-trifluoro-1-phenylethylamin, 2,2-difluoro-1-phenylethylamin, 1-(4-bromo-phenyl)-2,2,2-trifluoroethyl, 3-bromo-3,3-difluoropropyl, 3,3,3-trifluoropropylamin, 3,3,3-trifluoro-n-propyl, 1H,1H,2H,2H-perfluorodecyl, 3-(perfluorooctyl) propyl, pentafluorophenyl, 2,3,5,6-tetrafluorophenyl, 4-cyano-(2,3,5,6)-tetrafluorophenyl, 4-carboxy-2,3,5,6-tetrafluorophenyl, 2,4-difluorophenyl, 2,4,5-trifluorophenyl, 2,4,6-trifluorophenyl, 2,5-difluorophenyl, 2-fluoro-5-nitrophenyl, 2-fluoro-5-trifluoromethylphenyl, 2-fluoro-5-methylphenyl, 2,6-difluorophenyl, 4-carboxamido-2,3,5,6-tetrafluorophenyl, 2-bromo-4,6-difluorophenyl, 4-bromo-2-fluorophenyl, 2,3-difluorophenyl, 4-chloro-2-fluorophenyl, 2,3,4-trifluorophenyl, 2-fluoro-4-iodphenyl, 4-bromo-2,3,5,6-tetrafluorophenyl, 2,3,6-trifluorophenyl, 2-bromo-3,4,6-trifluorophenyl, 2-bromo-4,5,6-trifluorophenyl, 4-bromo-2,6-difluorophenyl, 2,3,4,5-tetrafluorophenyl, 2,4-difluoro-6-nitrophenyl, 2-fluoro-4-nitrophenyl, 2-chloro-6-fluorophenyl, 2-fluoro-4-methylphenyl, 3-chloro-2,4-difluorophenyl, 2,4-dibromo-6-fluorophenyl, 3,5-dichloro-2,4-difluorophenyl, 4-cyano-1-fluorophenyl, 1-chloro-4-fluorophenyl, 2-fluoro-3-trifluoromethylphenyl, 2-trifluoromethyl-6-fluorophenyl, 2,3,4,6-tetrafluorophenyl, 3-chloro-2-fluorophenyl, 5-chloro-2-fluorophenyl, 2-bromo-4-chloro-6-fluorophenyl, 2,3-dicyano-4,5,6-trifluorophenyl, 2,4,5-trifluoro-3-carboxyphenyl, 2,3,4-trifluoro-6-carboxyphenyl, 2,3,5-trifluorophenyl, 4-trifluoromethyl-1,2,3,5,6-tetrafluorophenyl, 1-fluoro-5-carboxyphenyl, 2-chloro-4,6-difluorophenyl, 6-bromo-3-chloro-2,4-difluorophenyl, 2,3,4-trifluoro-6-nitrophenyl, 2,5-difluoro-4-cyanophenyl, 2,5-difluoro-4-trifluoromethylphenyl, 2,3-difluoro-6-nitrophenyl, 4-trifluoromethyl-2,3-difluorophenyl, 2-bromo-4,6-difluorophenyl, 4-bromo-2-fluorophenyl, 2-nitrotetrafluorophenyl, 2,2',3,3',4',5,5',6,6'-nonabiphenyl, 2-nitro-3,5,6-trifluorophenyl, 2-bromo-6-fluorophenyl, 4-chloro-2-fluoro-6-iodphenyl, 2-fluoro-6-carboxyphenyl, 2,4-difluoro-3-trifluorophenyl, 2-fluoro-4-trifluorophenyl, 2-fluoro-4-carboxyphenyl, 4-bromo-2,5-difluorophenyl, 2,5-dibromo-3,4,6-trifluorophenyl, 2-fluoro-5-methylsulphonylpenyl, 5-bromo-2-fluorophenyl, 2-fluoro-4-hydroxymethylphenyl, 3-fluoro-4-bromomethylphenyl, 2-nitro-4-trifluoromethylphenyl, 4-trifluoromethylphenyl, 2-bromo-4-trifluoromethylphenyl, 2-bromo-6-chloro-4-(trifluoromethyl)phenyl, 2-chloro-4-trifluoromethylphenyl, 3-nitro-4-(trifluoromethyl)phenyl, 2,6-dichloro-4-(trifluoromethyl)phenyl, 4-trifluorophenyl, 2,6-dibromo-4-(trifluoromethyl)phenyl, 4-trifluoromethyl-2,3,5,6-tetrafluorophenyl, 3-fluoro-4-trifluoromethylphenyl, 2,5-difluoro-4-trifluoromethylphenyl, 3,5-difluoro-4-trifluoromethylphenyl, 2,3-difluoro-4-trifluoromethylphenyl, 2,4-bis(trifluoromethyl)phenyl, 3-chloro-4-trifluoromethylphenyl, 2-bromo-4,5-di(trifluoromethyl)phenyl, 5-chloro-2-nitro-4-(trifluoromethyl)phenyl, 2,4,6-tris(trifluoromethyl)phenyl, 3,4-Bis(trifluoromethyl)phenyl, 2-fluoro-3-trifluoromethylphenyl, 2-Iod-4-trifluoromethylphenyl, 2-nitro-4,5-bis(trifluoromethyl) phenyl, 2-methyl-4-(trifluoromethyl)phenyl, 3,5-dichloro-4-(trifluoromethyl)phenyl, 2,3,6-trichloro-4-(trifluoromethyl) phenyl, 4-(trifluoromethyl)benzyl, 2-fluoro-4-(trifluoromethyl)benzyl, 3-fluoro-4-(trifluoromethyl)benzyl, 3-chloro-4-(trifluoromethyl)benzyl, 4-fluorophenethyl, 3-(trifluoromethyl)phenethyl, 2-chloro-6-fluorophenethyl, 2,6-dichlorophenethyl, 3-fluorophenethyl, 2-fluorophenethyl, (2-trifluoromethyl)phenethyl, 4-fluorophenethyl, 3-fluorophenethyl, 4-trifluoromethylphenethyl, 2,3-difluorophenethyl, 3,4-difluorophenethyl, 2,4-difluorophenethyl, 2,5-difluorophenethyl, 3,5-difluorophenethyl, 2,6-difluorophenethyl,4-(4-fluorophenyl)phenethyl, 3,5-di(trifluoromethyl)phenethyl, pentafluorophenethyl, 2,4-di(trifluoromethyl)phenethyl, 2-nitro-4-(trifluoromethyl)phenethyl, (2-fluoro-3-trifluoromethyl)phenethyl, (2-fluoro-5-trifluoromethyl)phenethyl, (3-fluoro-5-trifluoromethyl)phenethyl, (4-fluoro-2-trifluoromethyl)phenethyl, (4-fluoro-3-trifluoromethyl)phenethyl, (2-fluoro-6-trifluoromethyl)phenethyl, (2,3,6-trifluoro)phenethyl, (2,4,5-trifluoro)phenethyl, (2,4,6-trifluoro)phenethyl, (2,3,4-trifluoro)phenethyl, (3,4,5-trifluoro)phenethyl, (2,3,5-trifluoro)phenethyl, (2-chloro-5-fluoro)phenethyl, (3-fluoro-4-trifluoromethyl)phenethyl, (2-chloro-5-trifluoromethyl)phenethyl, (2-fluoro-3-chloro-5-trifluoromethyl)phenethyl, (2-fluoro-3-chloro)phenethyl, (4-fluoro-3-chloro)phenethyl, (2-fluoro-4-chloro)phenethyl, (2,3-difluoro-4-methyl)phenethyl-, 2,6-difluoro-3-chlorophenethyl, (2,6-difluoro-3-methyl)phenethyl, (2-trifluoromethyl-5-chloro)phenethyl, (6-chloro-2-fluoro-5-methyl)phenethyl, (2,4-dichloro-5-fluoro)phenethyl, 5-chloro-2-fluorophenethyl, (2,5-difluoro-6-chloro)phenethyl, (2,3,4,5-tetrafluoro)phenethyl, (2-fluoro-4-trifluoromethyl)phenethyl, 2,3-(difluoro-4-trifluoromethyl)phenethyl, (2,5-di(trifluoromethyl))phenethyl, 2-fluoro-3,5-dibromophenethyl, (3-fluoro-4-nitro)phenethyl, (2-bromo-4-trifluoromethyl)phenethyl, 2-(bromo-5-fluoro)phenethyl, (2,6-difluoro-4-bromo)phenethyl, (2,6-difluoro-4-chloro)phenethyl, (3-chloro-5-fluoro)phenethyl, (2-bromo-5-trifluoromethyl)phenethyl and the like.

In the compounds of the formula (I), the $R^1$ and $R^2$ radicals may have identical or different definitions. In a preferred embodiment, the $R^1$ and $R^2$ radicals have identical definitions.

In the compounds of the formula (I), the $R^3$ and $R^4$ radicals may have identical or different definitions. In a preferred embodiment, the $R^3$ and $R^4$ radicals have identical definitions.

In a preferred embodiment, at least one of the radicals $R^1$, $R^2$, $R^3$ and $R^4$ is selected from

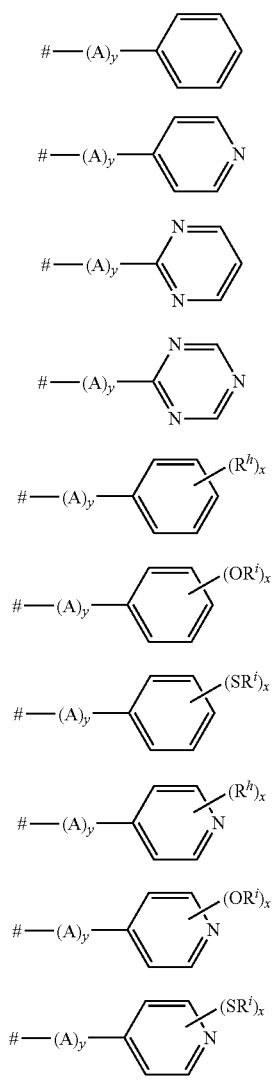

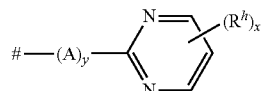

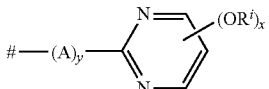

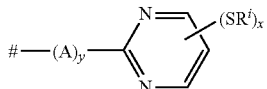

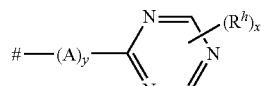

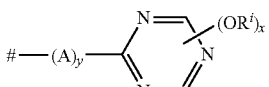

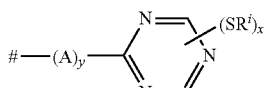

wherein
# represents the bonding side to a nitrogen atom,
A where present, is a $C_1$-$C_{10}$-alkylene group which may be interrupted by one or more nonadjacent groups which are selected from —O— and —S—,
y is 0 or 1,
the residues $R^h$ in formulae A.5, A.8, A.11 and A.14 are selected independently of one another from $C_1$-$C_{30}$-alkyl, $C_1$-$C_{30}$-fluoroalkyl, fluorine, chlorine, bromine, $NE^1E^2$, nitro and cyano, where $E^1$ and $E^2$, independently of one another, are hydrogen, alkyl, cycloalkyl, heterocycloalkyl, aryl or hetaryl,
the residues $R^i$ in formulae A.6, A.7, A.9, A.10, A.12, A.13, A.15 and A.16 are selected independently of one another from $C_1$-$C_{30}$-alkyl,
x in formulae A.5, A.6 and A.7 is 1, 2, 3, 4 or 5,
in formulae A.8, A.9 and A.10 is 1, 2, 3 or 4,
in formulae A.11, A.12 and A.13 is 1, 2 or 3,
in formulae A.14, A.15 and A.16 is 1 or 2.

In a preferred embodiment of the compounds (I), the radicals $R^1$ and $R^2$ are independently selected from radicals of the general formulae (A.1) to (A.16). In particular, $R^1$ and $R^2$ have the same meaning and are selected from radicals of the general formulae (A.1) to (A.16).

In a further preferred embodiment of the compounds (I), the radicals $R^3$ and $R^4$ are independently selected from radicals of the general formulae (A.1) to (A.16). In particular, $R^3$ and $R^4$ have the same meaning and are selected from radicals of the general formulae (A.1) to (A.16).

Preferably, in the formulae A.5, A.8, A.11 and A.14 the $R^h$ radicals are selected from $C_1$-$C_{12}$-alkyl or $C_1$-$C_{12}$-fluoroalkyl. In particular, in the formulae A.5, A.8, A.11 and A.14 the $R^h$ radicals are selected from $C_1$-$C_4$-alkyl or $C_1$-$C_4$-fluoroalkyl.

Preferably, in the formulae in formulae A.6, A.7, A.9, A.10, A.12, A.13, A.15 and A.16 the $R^i$ radicals are selected from $C_1$-$C_{12}$-alkyl.

In a preferred embodiment, in the compounds of the formula (I) $R^1$ and $R^2$ are each independently selected from radicals of the formula A.5. Preferably, $R^1$ and $R^2$ are each independently selected from phenyl-($C_1$-$C_{30}$)-alkyl groups, wherein the benzene ring of the phenylalkyl group bears 1, 2, 3, 4 or 5 substituents, independently selected from F, Cl, Br, CN, $C_1$-$C_{30}$-alkyl and perfluoro-$C_1$-$C_{30}$-alkyl and the phenylalkyl group is attached to the imide nitrogen atom via the alkyl moiety of the phenylalkyl group.

More preferably, $R^1$ and $R^2$ have the same meaning and are selected from phenyl-($C_1$-$C_{30}$)-alkyl groups, wherein the benzene ring of the phenylalkyl group bears 1, 2, 3, 4 or 5 substituents, independently selected from F, Cl, Br, CN, $C_1$-$C_{30}$-alkyl and perfluoro-$C_1$-$C_{30}$-alkyl. In particular, $R^1$ and $R^2$ have the same meaning and are selected from phenyl-($C_1$-$C_4$)-alkyl groups, wherein the benzene ring of the phenylalkyl group bears 1, 2, 3, 4 or 5 substituents, independently selected from F, Cl, Br, CN, $C_1$-$C_{30}$-alkyl and perfluoro-$C_1$-$C_{12}$-alkyl.

Examples of preferred radicals of the formula A.1 are mentioned in the following table 1. In a preferred embodiment, in the compounds of the formula (I) $R^1$ and $R^2$ are each independently selected from radicals of the formula A.1 mentioned in the following table 1. In particular, $R^1$ and $R^2$ have the same meaning and are selected from radicals of the formula A.1 mentioned in the following table 1. In a further preferred embodiment, in the compounds of the formula (I) $R^3$ and $R^4$ are each independently selected from radicals of the formula A.1 mentioned in the following table 1. In particular, $R^3$ and $R^4$ have the same meaning and are selected from radicals of the formula A.1 mentioned in the following table 1.

TABLE 1

(preferred radicals of the formula A.1):

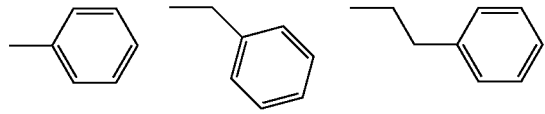

Examples of preferred radicals of the formula A.5 are mentioned in the following table 2. In a preferred embodiment, in the compounds of the formula (I) $R^1$ and $R^2$ are each independently selected from radicals of the formula A.5 mentioned in the following table 2. In particular, $R^1$ and $R^2$ have the same meaning and are selected from radicals of the formula A.5 mentioned in the following table 2. In a further preferred embodiment, in the compounds of the formula (I) $R^3$ and $R^4$ are each independently selected from radicals of the formula A.5 mentioned in the following table 2. In particular, $R^3$ and $R^4$ have the same meaning and are selected from radicals of the formula A.5 mentioned in the following table 2.

TABLE 2

(preferred radicals of the formula A.5):

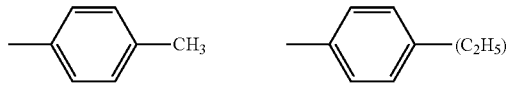

TABLE 2-continued (preferred radicals of the formula A.5):

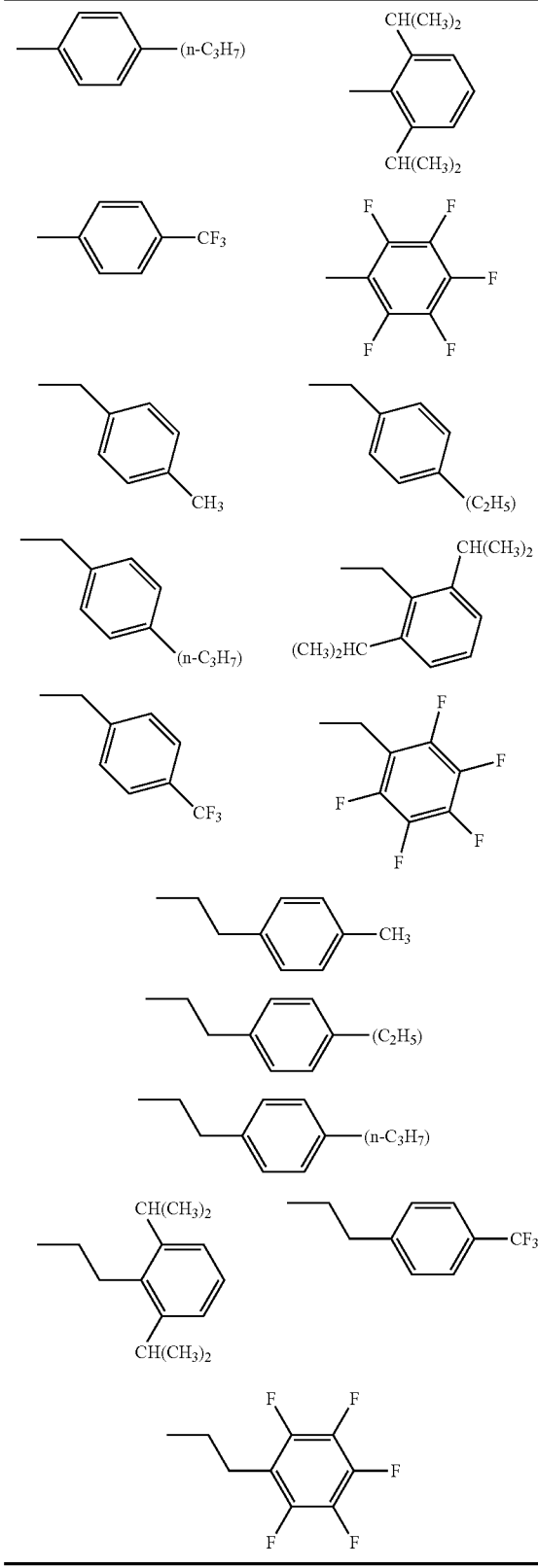

In a preferred embodiment, at least one of the radicals $R^5$, $R^6$, $R^7$, $R^8$, $R^9$, $R^{10}$, $R^{11}$ and $R^{12}$ is selected from

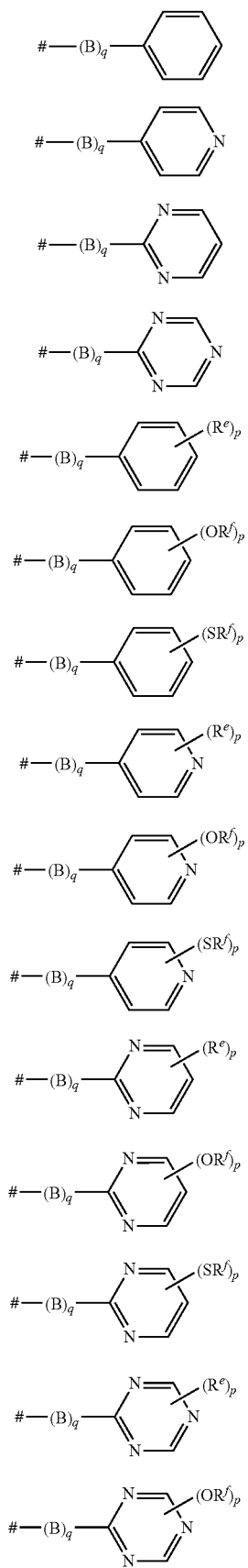

wherein
# represents the bonding side to a nitrogen atom,
B where present, is a divalent bridging group selected from —O—, —S— or $C_1$-$C_{10}$-alkylene which may be interrupted and/or terminated by one or more nonadjacent groups which are selected from —O— and —S—,
q is 0 or 1,
the residues $R^e$ in formulae B.5, B.8, B.11 and B.14 are selected independently of one another from $C_1$-$C_{30}$-alkyl, $C_1$-$C_{30}$-fluoroalkyl, fluorine, chlorine, bromine, $NE^1E^2$, nitro and cyano, where $E^1$ and $E^2$, independently of one another, are hydrogen, alkyl, cycloalkyl, heterocycloalkyl, aryl or hetaryl,
the residues $R^f$ in formulae B.6, B.7, B.9, B.10, B.12, B.13, B.15 and B.16 are selected independently of one another from $C_1$-$C_{30}$-alkyl,
p in formulae B.5, B.6 and B.7 is 1, 2, 3, 4 or 5,
in formulae B.8, B.9 and B.10 is 1, 2, 3 or 4,
in formulae B.11, B.12 and B.13 is 1, 2 or 3,
in formulae B.14, B.15 and B.16 is 1 or 2.

Examples of preferred radicals of the formula B.1 are mentioned in the following table 3. In a preferred embodiment, in the compounds of the formula (I) at least one of the radicals $R^5$, $R^6$, $R^7$, $R^8$, $R^9$, $R^{10}$, $R^{11}$ and $R^{12}$ is selected from radicals of the formula B.1 mentioned in the following table 3.

TABLE 3

(preferred radicals of the formula B.1):

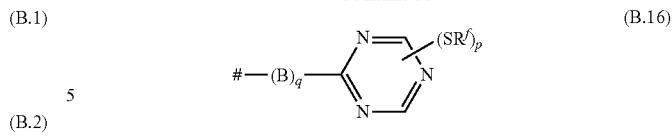

Examples of preferred radicals of the formula B.5 are mentioned in the following table 4. In a preferred embodiment, in the compounds of the formula (I) at least one of the radicals $R^5$, $R^6$, $R^7$, $R^8$, $R^9$, $R^{10}$, $R^{11}$ and $R^{12}$ is selected from radicals of the formula B.5 mentioned in the following table 4.

TABLE 4
(preferred radicals of the formula B.5):
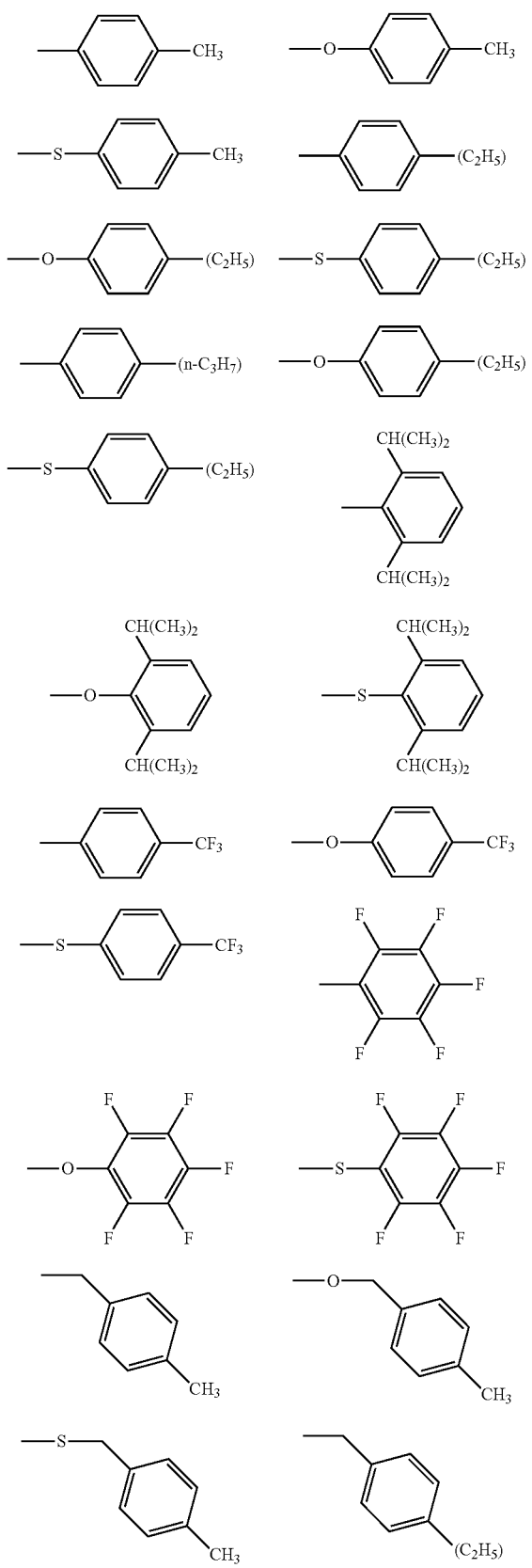
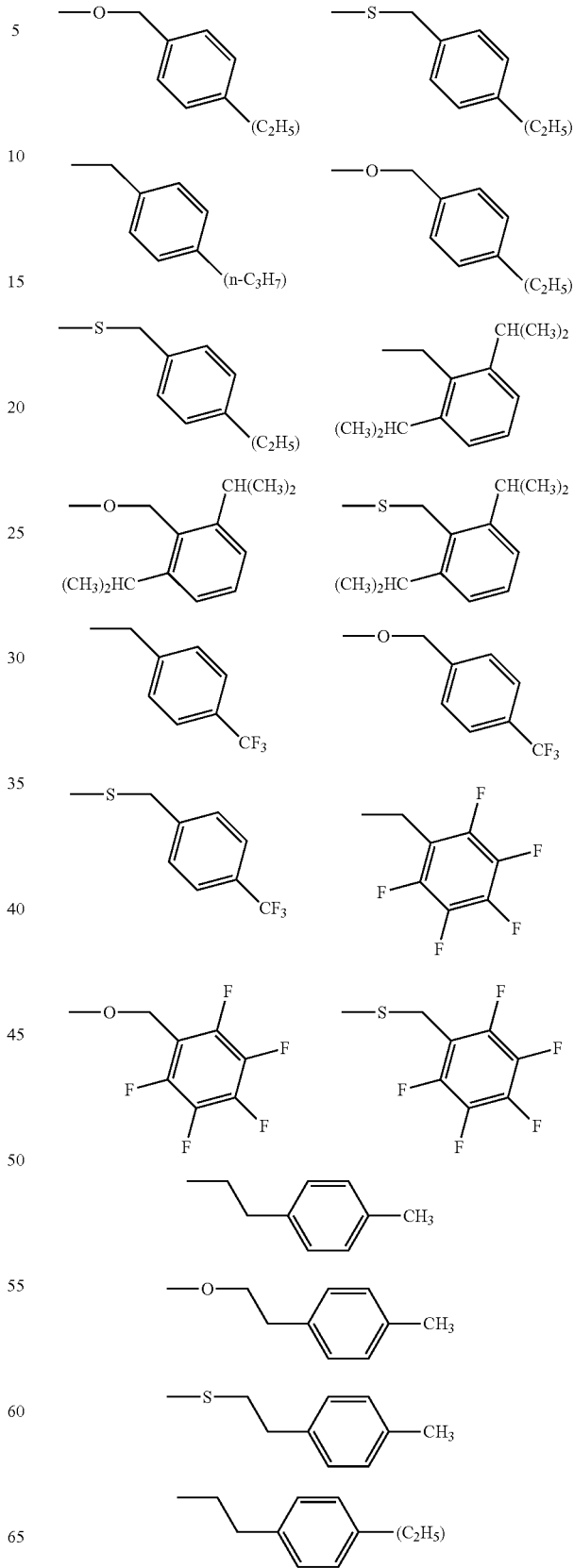
TABLE 4-continued
(preferred radicals of the formula B.5):

TABLE 4-continued (preferred radicals of the formula B.5):

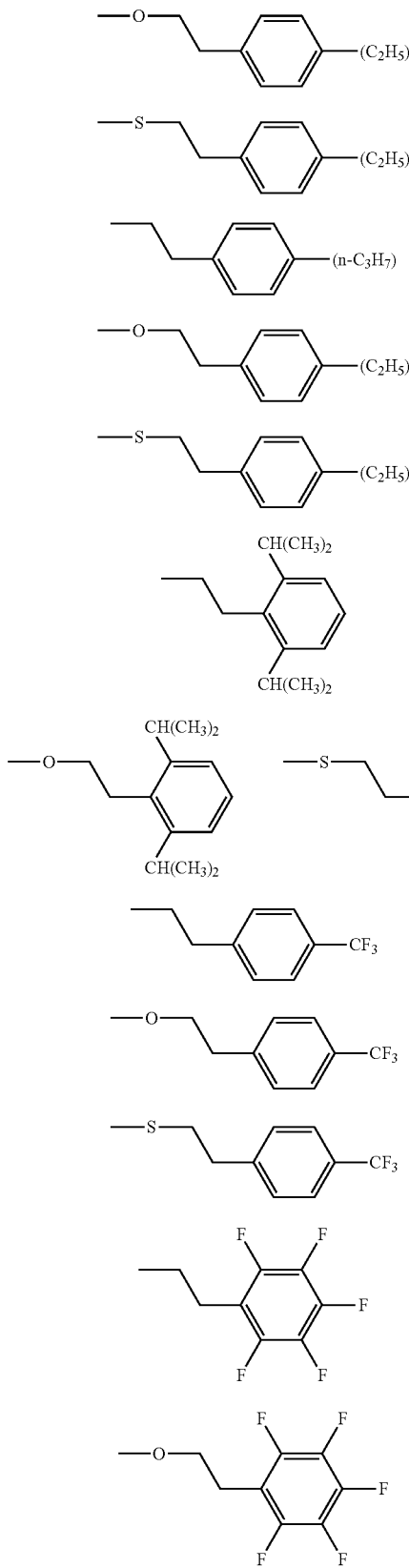

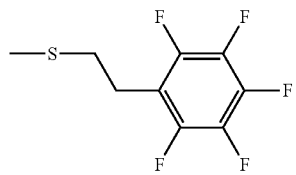

In a preferred embodiment, at least one of the radicals $R^1$, $R^2$, $R^3$, $R^4$, $R^5$, $R^6$, $R^7$, $R^8$, $R^9$, $R^{10}$, $R^{11}$ and $R^{12}$ is a linear $C_1$-$C_{30}$-alkyl radical. Preferred linear alkyl groups are methyl, ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-hexadecyl, n-octadecyl and n-eicosyl.

In a preferred embodiment, at least one of the radicals $R^1$, $R^2$, $R^3$, $R^4$, $R^5$, $R^6$, $R^7$, $R^8$, $R^9$, $R^{10}$, $R^{11}$ and $R^{12}$ is a branched $C_3$-$C_{30}$-alkyl radical.

Preferably at least one of the radicals $R^1$, $R^2$, $R^3$, $R^4$, $R^5$, $R^6$, $R^7$, $R^8$, $R^9$, $R^{10}$, $R^{11}$ and $R^{12}$ is selected from radicals of the general formula (C)

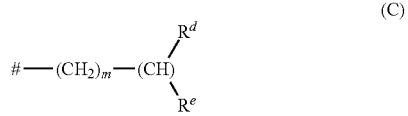

in which
# is a bonding site,
m is 0 or 1, and
$R^d$ and $R^e$ are independently selected from $C_1$- to $C_{30}$-alkyl.

Preferably, in the formula (C), $R^d$ and $R^e$ are independently selected from $C_1$- to $C_{20}$-alkyl, especially $C_1$- to $C_{12}$-alkyl.

Preferably, in the formula (C), the sum of the carbon atoms of the radicals (C) is an integer from 3 to 55, more preferably from 4 to 40, in particular from 5 to 30.

In a first embodiment, in the formula (C) m is 0. Preferably at least one of the radicals $R^1$, $R^2$, $R^3$, $R^4$, $R^5$, $R^6$, $R^7$, $R^8$, $R^9$, $R^{10}$, $R^{11}$ and $R^{12}$ is selected from radicals of the general formula (C1)

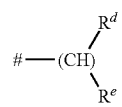

in which
# is a bonding site, and
$R^d$ and $R^e$ are independently selected from $C_1$- to $C_{28}$-alkyl, where the sum of the carbon atoms of the $R^d$ and $R^e$ radicals is an integer from 2 to 29.

In a preferred embodiment of the compounds (I), the radicals $R^1$ and $R^2$ are independently selected from radicals of the general formula (C). In particular, $R^1$ and $R^2$ have the same meaning and are selected from radicals of the general formula (C).

In a further preferred embodiment of the compounds (I), the radicals $R^1$ and $R^2$ are independently selected from radicals of the general formula (C1). In particular, $R^1$ and $R^2$ have the same meaning and are selected from radicals of the general formula (C1).

In a further preferred embodiment of the compounds (I), the radicals $R^3$ and $R^4$ are independently selected from radicals of the general formula (C). In particular, $R^3$ and $R^4$ have the same meaning and are selected from radicals of the general formula (C).

In a further preferred embodiment of the compounds (I), the radicals $R^3$ and $R^4$ are independently selected from radicals of the general formula (C1). In particular, $R^3$ and $R^4$ have the same meaning and are selected from radicals of the general formula (C1).

Preferably, in the formula (C1), the $R^d$ and $R^e$ radicals are selected from $C_1$- to $C_{12}$-alkyl, especially $C_1$- to $C_8$-alkyl.

Preferred radicals of the formula (C1) are:

1-ethyl propyl, 1-methyl propyl, 1-propyl butyl, 1-ethyl butyl, 1-methyl butyl, 1-butylpentyl, 1-propylpentyl, 1-ethylpentyl, 1-methyl pentyl, 1-pentylhexyl, 1-butyl hexyl, 1-propylhexyl, 1-ethyl hexyl, 1-methyl hexyl, 1-hexyl heptyl, 1-pentylheptyl, 1-butyl heptyl, 1-propylheptyl, 1-ethylheptyl, 1-methyl heptyl, 1-heptyloctyl, 1-hexyloctyl, 1-pentyloctyl, 1-butyloctyl, 1-propyloctyl, 1-ethyloctyl, 1-methyloctyl, 1-octylnonyl, 1-heptylnonyl, 1-hexylnonyl, 1-pentylnonyl, 1-butylnonyl, 1-propylnonyl, 1-ethylnonyl, 1-methylnonyl, 1-nonyldecyl, 1-octyldecyl, 1-heptyldecyl, 1-hexyldecyl, 1-pentyldecyl, 1-butyldecyl, 1-propyldecyl, 1-ethyldecyl, 1-methyldecyl, 1-decylundecyl, 1-nonylundecyl, 1-octylundecyl, 1-heptylundecyl, 1-hexylundecyl, 1-pentylundecyl, 1-butylundecyl, 1-propylundecyl, 1-ethylundecyl, 1-methylundecyl, 1-undecyldodecyl, 1-decyldodecyl, 1-nonyldodecyl, 1-octyldodecyl, 1-heptyldodecyl, 1-hexyldodecyl, 1-pentyldodecyl, 1-butyldodecyl, 1-propyldodecyl, 1-ethyldodecyl, 1-methyldodecyl, 1-dodecyltridecyl, 1-undecyltridecyl, 1-decyltridecyl, 1-nonyltridecyl, 1-octyltridecyl, 1-heptyltridecyl, 1-hexyltridecyl, 1-pentyltridecyl, 1-butyltridecyl, 1-propyltridecyl, 1-ethyltridecyl, 1-methyltridecyl, 1-tridecyltetradecyl, 1-undecyltetradecyl, 1-decyltetradecyl, 1-nonyltetradecyl, 1-octyltetradecyl, 1-heptyltetradecyl, 1-hexyltetradecyl, 1-pentyltetradecyl, 1-butyltetradecyl, 1-propyltetradecyl, 1-ethyltetradecyl, 1-methyltetradecyl, 1-pentadecylhexadecyl, 1-tetradecylhexadecyl, 1-tridecylhexadecyl, 1-dodecylhexadecyl, 1-undecylhexadecyl, 1-decylhexadecyl, 1-nonylhexadecyl, 1-octylhexadecyl, 1-heptylhexadecyl, 1-hexylhexadecyl, 1-pentylhexadecyl, 1-butylhexadecyl, 1-propylhexadecyl, 1-ethylhexadecyl, 1-methylhexadecyl, 1-hexadecyloctadecyl, 1-pentadecyloctadecyl, 1-tetradecyloctadecyl, 1-tridecyloctadecyl, 1-dodecyloctadecyl, 1-undecyloctadecyl, 1-decyloctadecyl, 1-nonyloctadecyl, 1-octyloctadecyl, 1-heptyloctadecyl, 1-hexyloctadecyl, 1-pentyloctadecyl, 1-butyloctadecyl, 1-propyloctadecyl, 1-ethyloctadecyl, 1-methyloctadecyl, 1-nonadecyleicosanyl, 1-octadecyleicosanyl, 1-heptadecyleicosanyl, 1-hexadecyleicosanyl, 1-pentadecyleicosanyl, 1-tetradecyleicosanyl, 1-tridecyleicosanyl, 1-dodecyleicosanyl, 1-undecyleicosanyl, 1-decyleicosanyl, 1-nonyleicosanyl, 1-octyleicosanyl, 1-heptyleicosanyl, 1-hexyleicosanyl, 1-pentyleicosanyl, 1-butyleicosanyl, 1-propyleicosanyl, 1-ethyleicosanyl, 1-methyleicosanyl, 1-eicosanyldocosanyl, 1-nonadecyldocosanyl, 1-octadecyldocosanyl, 1-heptadecyldocosanyl, 1-hexadecyldocosanyl, 1-pentadecyldocosanyl, 1-tetradecyldocosanyl, 1-tridecyldocosanyl, 1-undecyldocosanyl, 1-decyldocosanyl, 1-nonyldocosanyl, 1-octyldocosanyl, 1-heptyldocosanyl, 1-hexyldocosanyl, 1-pentyldocosanyl, 1-butyldocosanyl, 1-propyldocosanyl, 1-ethyldocosanyl, 1-methyldocosanyl, 1-tricosanyltetracosanyl, 1-docosanyltetracosanyl, 1-nonadecyltetracosanyl, 1-octadecyltetracosanyl, 1-heptadecyltetracosanyl, 1-hexadecyltetracosanyl, 1-pentadecyltetracosanyl, 1-pentadecyltetracosanyl, 1-tetradecyltetracosanyl, 1-tridecyltetracosanyl, 1-dodecyltetracosanyl, 1-undecyltetracosanyl, 1-decyltetracosanyl, 1-nonyltetracosanyl, 1-octyltetracosanyl, 1-heptyltetracosanyl, 1-hexyltetracosanyl, 1-pentyltetracosanyl, 1-butyltetracosanyl, 1-propyltetracosanyl, 1-ethyltetracosanyl, 1-methyltetracosanyl, 1-heptacosanyloctacosanyl, 1-hexacosanyloctacosanyl, 1-pentacosanyloctacosanyl, 1-tetracosanyloctacosanyl, 1-tricosanyloctacosanyl, 1-docosanyloctacosanyl, 1-nonadecyloctacosanyl, 1-octadecyloctacosanyl, 1-heptadecyloctacosanyl, 1-hexadecyloctacosanyl, 1-hexadecyloctacosanyl, 1-pentadecyloctacosanyl, 1-tetradecyloctacosanyl, 1-tridecyloctacosanyl, 1-dodecyloctacosanyl, 1-undecyloctacosanyl, 1-decyloctacosanyl, 1-nonyloctacosanyl, 1-octyloctacosanyl, 1-heptyloctacosanyl, 1-hexyloctacosanyl, 1-pentyloctacosanyl, 1-butyloctacosanyl, 1-propyloctacosanyl, 1-ethyloctacosanyl, 1-methyloctacosanyl.

Particularly preferred radicals of the formula (C1) are:

1-methylethyl, 1-methylpropyl, 1-methylbutyl, 1-methylpentyl, 1-methylhexyl, 1-methylheptyl, 1-methyloctyl, 1-ethylpropyl, 1-ethylbutyl, 1-ethylpentyl, 1-ethylhexyl, 1-ethylheptyl, 1-ethyloctyl, 1-propylbutyl, 1-propylpentyl, 1-propylhexyl, 1-propylheptyl, 1-propyloctyl, 1-butylpentyl, 1-butylhexyl, 1-butylheptyl, 1-butyloctyl, 1-pentylhexyl, 1-pentylheptyl, 1-pentyloctyl, 1-hexylheptyl, 1-hexyloctyl, 1-heptyloctyl.

In a second embodiment, in the formula (C) m is 1. Preferred radicals of the formula (C) wherein m is 1 are:

2-methylpropyl, 2-ethylbutyl, 2-methylbutyl, 2-propylpentyl, 2-ethylpentyl, 2-methylpentyl, 2-butylhexyl, 2-propylhexyl, 2-ethylhexyl, 2-methylhexyl, 2-pentylheptyl, 2-butylheptyl, 2-propylheptyl, 2-ethylheptyl, 2-methylheptyl, 2-hexyloctyl, 2-pentyloctyl, 2-butyloctyl, 2-propyloctyl, 2-ethyloctyl, 2-methyloctyl, 2-heptylnonyl, 2-hexylnonyl, 2-pentylnonyl, 2-butylnonyl, 2-propylnonyl, 2-ethylnonyl, 2-methylnonyl, 2-octyldecyl, 2-heptyldecyl, 2-hexyldecyl, 2-pentyldecyl, 2-butyldecyl, 2-propyldecyl, 2-ethyldecyl, 2-methyldecyl, 2-nonylundecyl, 2-octylundecyl, 2-heptylundecyl, 2-hexylundecyl, 2-pentylundecyl, 2-butylundecyl, 2-propylundecyl, 2-ethylundecyl, 2-methylundecyl, 2-decyldodecyl, 2-nonyldodecyl, 2-octyldodecyl, 2-heptyldodecyl, 2-hexyldodecyl, 2-pentyldodecyl, 2-butyldodecyl, 2-propyldodecyl, 2-ethyldodecyl, 2-methyldodecyl, 2-undecyltridecyl, 2-decyltridecyl, 2-nonyltridecyl, 2-octyltridecyl, 2-heptyltridecyl, 2-hexyltridecyl, 2-pentyltridecyl, 2-butyltridecyl, 2-propyltridecyl, 2-ethyltridecyl, 2-methyltridecyl, 2-undecyltetradecyl, 2-decyltetradecyl, 2-nonyltetradecyl, 2-octyltetradecyl, 2-hetyltetradecyl, 2-hexyltetradecyl, 2-pentyltetradecyl, 2-butyltetradecyl, 2-propyltetradecyl, 2-ethyltetradecyl, 2-methyltetradecyl, 2-tetradecylhexadecyl, 2-tridecylhexadecyl, 2-dodecylhexadecyl, 2-undecylhexadecyl, 2-decylhexadecyl, 2-nonylhexadecyl, 2-octylhexadecyl, 2-heptylhexadecyl, 2-hexylhexadecyl, 2-pentylhexadecyl, 2-butylhexadecyl, 2-propylhexadecyl, 2-ethylhexadecyl, 2-methylhexadecyl, 2-hexadecyloctadecyl, 2-pentadecyloctadecyl, 2-tetradecyloctadecyl, 2-tridecyloctadecyl, 2-dodecyloctadecyl, 2-undecyloctadecyl, 2-decyloctadecyl, 2-nonyloctadecyl, 2-octyloctadecyl, 2-heptyloctadecyl, 2-hexyloctadecyl, 2-pentyloctadecyl, 2-butyloctadecyl, 2-propyloctadecyl, 2-ethyloctadecyl, 2-methyloctadecyl, 2-octadecyleicosanyl, 2-heptadecyleicosanyl, 2-hexadecyleicosanyl, 2-pentadecyleicosanyl, 2-tetradecyleicosanyl, 2-tridecyleicosanyl, 2-dodecyleicosanyl, 2-undecyleicosanyl, 2-decyleicosanyl, 2-nonyleicosanyl, 2-octyleicosanyl, 2-heptyleicosanyl, 2-hexyleicosanyl, 2-pentyleicosanyl, 2-butyleicosanyl, 2-propyleicosanyl, 2-ethyleicosanyl, 2-methyleicosanyl, 2-eicosanyldocosanyl, 2-nonadecyldocosanyl, 2-octadecyldocosanyl, 2-heptadecyldocosanyl, 2-hexadecyldocosanyl, 2-pentadecyldocosanyl, 2-tetradecyldocosanyl, 2-tridecyldocosanyl, 2-undecyldocosanyl, 2-decyldocosanyl, 2-nonyldocosanyl, 2-octyldocosanyl, 2-heptyldocosanyl, 2-hexyldocosanyl, 2-pentyldocosanyl, 2-butyldocosanyl, 2-propyldocosanyl, 2-ethyldocosanyl, 2-methyldocosanyl, 2-docosanyltetracosanyl, 2-nonadecyltetracosanyl, 2-octadecyltetracosanyl, 2-heptadecyltetracosanyl, 2-hexadecyltetracosanyl, 2-pentadecyltetracosanyl, 2-pentadecyltetracosanyl, 2-tetradecyltetracosanyl, 2-tridecyltetracosanyl, 2-dodecyltetracosanyl, 2-undecyltetracosanyl, 2-decyltetracosanyl, 2-nonyltetracosanyl, 2-octyltetracosanyl, 2-heptyltetracosanyl, 2-hexyltetracosanyl, 2-pentyltetracosanyl, 2-butyltetracosanyl, 2-propyltetracosanyl, 2-ethyltetracosanyl, 2-methyltetracosanyl, 2-hexacosanyloctacosanyl, 2-pentacosanyloctacosanyl, 2-tetracosanyloctacosanyl, 2-tricosanyloctacosanyl, 2-docosanyloctacosanyl, 2-nonadecyloctacosanyl, 2-octadecyloctacosanyl, 2-heptadecyloctacosanyl, 2-hexadecyloctacosanyl, 2-hexadecyloctacosanyl, 2-pentadecyloctacosanyl, 2-tetradecyloctacosanyl, 2-tridecyloctacosanyl, 2-dodecyloctacosanyl, 2-undecyloctacosanyl, 2-decyloctacosanyl, 2-nonyloctacosanyl, 2-octyloctacosanyl, 2-heptyloctacosanyl, 2-hexyloctacosanyl, 2-pentyloctacosanyl, 2-butyloctacosanyl, 2-propyloctacosanyl, 2-ethyloctacosanyl, 2-methyloctacosanyl.

Examples of preferred radicals of the formula (C) wherein m is 1 are 2-ethylhexyl, 2-ethylheptyl, 2-ethyloctyl, 2-ethylnonyl and 2-ethyldecyl.

In a preferred embodiment of the compounds (I), the radicals $R^1$ and $R^2$ are independently selected from radicals of the general formula (C), wherein m is 1. In particular, $R^1$ and $R^2$ have the same meaning and are selected from radicals of the general formula (C), wherein m is 1. Especially, $R^1$ and $R^2$ have the same meaning and are both 2-ethylhexyl, 2-ethylheptyl, 2-ethyloctyl, 2-ethylnonyl or 2-ethyldecyl.

In a preferred embodiment of the compounds (I), the radicals $R^3$ and $R^4$ are independently selected from radicals of the general formula (C), wherein m is 1. In particular, $R^3$ and $R^4$ have the same meaning and are selected from radicals of the general formula (C), wherein m is 1. Especially, $R^3$ and $R^4$ have the same meaning and are both 2-ethylhexyl, 2-ethylheptyl, 2-ethyloctyl, 2-ethylnonyl or 2-ethyldecyl.

Preferably, at least one of the radicals $R^1$, $R^2$, $R^3$, $R^4$, $R^5$, $R^6$, $R^7$, $R^8$, $R^9$, $R^{10}$, $R^{11}$ and $R^{12}$ is selected from perfluoro-$C_1$-$C_{30}$-alkyl, 1H,1H-perfluoro-$C_2$-$C_{30}$-alkyl or 1H,1H,2H,2H-perfluoro-$C_3$-$C_{30}$-alkyl.

Preferably, in the compounds of the formula (I) $R^1$ and $R^2$ are each independently selected from perfluoro-$C_1$-$C_{30}$-alkyl. More preferably, $R^1$ and $R^2$ have the same meaning and are both perfluoro-$C_1$-$C_{30}$-alkyl.

Additionally preferably, in the compounds of the formula (I) $R^1$ and $R^2$ are each independently selected from 1H,1H-perfluoro-$C_2$-$C_{30}$-alkyl. More preferably, $R^1$ and $R^2$ have the same meaning and are both 1H,1H-perfluoro-$C_2$-$C_{30}$-alkyl.

Additionally preferably, in the compounds of the formula (I) $R^1$ and $R^2$ are each independently selected from 1H,1H,2H,2H-perfluoro-$C_3$-$C_{30}$-alkyl. More preferably, $R^1$ and $R^2$ have the same meaning and are 1H,1H,2H,2H-perfluoro-$C_3$-$C_{30}$-alkyl.

In a preferred embodiment, the $R^1$ and $R^2$ radicals are each independently perfluoro-$C_1$-$C_{20}$-alkyl or 1H,1H-perfluoro-$C_2$-$C_{20}$-alkyl or 1H,1H,2H,2H-perfluoro-$C_3$-$C_{20}$-alkyl.

In particular, the $R^1$ and $R^2$ radicals are each independently perfluoro-$C_1$-$C_{10}$-alkyl or 1H,1H-perfluoro-$C_2$-$C_{10}$-alkyl or 1H,1H,2H,2H-perfluoro-$C_3$-$C_{10}$-alkyl.

In a preferred embodiment, at least one of the radicals $R^1$ and $R^2$ is selected from $CF_3$, $C_2F_5$, n-$C_3F_7$, n-$C_4F_9$, n-$C_5F_{11}$, n-$C_6F_{13}$, $CF(CF_3)_2$, $C(CF_3)_3$, $CF_2CF(CF_3)_2$, $CF(CF_3)(C_2F_5)$, $CH_2$—$CF_3$, $CH_2$—$C_2F_5$, $CH_2$-(n-$C_3F_7$), $CH_2$-(n-$C_4F_9$), $CH_2$-(n-$C_5F_{11}$), $CH_2$-(n-$C_6F_{13}$), $CH_2$—$CF(CF_3)_2$, $CH_2$—$C(CF_3)_3$, $CH_2$—$CF_2CF(CF_3)_2$, $CH_2$—$CF(CF_3)(C_2F_5)$, $CH_2$—$CH_2$—$CF_3$, $CH_2$—$CH_2$—$C_2F_5$, $CH_2$—$CH_2$-(n-$C_3F_7$), $CH_2$—$CH_2$-(n-$C_4F_9$), $CH_2$—$CH_2$-(n-$C_5F_{11}$), $CH_2$—$CH_2$-(n-$C_6F_{13}$), $CH_2$—$CH_2$—$CF(CF_3)_2$, $CH_2$—$CH_2$—$C(CF_3)_3$, $CH_2$—$CH_2$—$CF_2CF(CF_3)_2$ and $CH_2$—$CH_2$—$CF(CF_3)(C_2F_5)$.

In a special embodiment, the afore-mentioned fluorinated radicals $R^1$ and $R^2$ have the same meaning.

$R^1$ and $R^2$ are preferably both $CH_2$—$CF_3$, $CH_2$—$C_2F_5$ or $CH_2$-(n-$C_3F_7$).

Preferably, $R^1$ and $R^2$ have the same meaning and are both 2-ethylhexyl, 2-ethylheptyl, 2-ethyloctyl, 2-ethylnonyl or 2-ethyldecyl.

Preferably, in the compounds of the formula (I) $R^3$ and $R^4$ are each independently selected from perfluoro-$C_1$-$C_{30}$-alkyl. More preferably, $R^3$ and $R^4$ have the same meaning and are both perfluoro-$C_1$-$C_{30}$-alkyl.

Additionally preferably, in the compounds of the formula (I) $R^3$ and $R^4$ are each independently selected from 1H,1H-perfluoro-$C_2$-$C_{30}$-alkyl. More preferably, $R^1$ and $R^2$ have the same meaning and are both 1H,1H-perfluoro-$C_2$-$C_{30}$-alkyl.

Additionally preferably, in the compounds of the formula (I) $R^3$ and $R^4$ are each independently selected from 1H,1H,2H,2H-perfluoro-$C_3$-$C_{30}$-alkyl. More preferably, $R^1$ and $R^2$ have the same meaning and are 1H,1H,2H,2H-perfluoro-$C_3$-$C_{30}$-alkyl.

In a preferred embodiment, the $R^3$ and $R^4$ radicals are each independently perfluoro-$C_1$-$C_{20}$-alkyl or 1H,1H-perfluoro-$C_2$-$C_{20}$-alkyl or 1H,1H,2H,2H-perfluoro-$C_3$-$C_{20}$-alkyl.

In particular, the $R^3$ and $R^4$ radicals are each independently perfluoro-$C_1$-$C_{10}$-alkyl or 1H,1H-perfluoro-$C_2$-$C_{10}$-alkyl or 1H,1H,2H,2H-perfluoro-$C_3$-$C_{10}$-alkyl.

In a preferred embodiment, at least one of the radicals $R^3$ and $R^4$ is selected from $CF_3$, $C_2F_5$, n-$C_3F_7$, n-$C_4F_9$, n-$C_5F_{11}$, n-$C_6F_{13}$, $CF(CF_3)_2$, $C(CF_3)_3$, $CF_2CF(CF_3)_2$, $CF(CF_3)(C_2F_5)$, $CH_2$—$CF_3$, $CH_2$—$C_2F_5$, $CH_2$-(n-$C_3F_7$), $CH_2$-(n-$C_4F_9$), $CH_2$-(n-$C_5F_{11}$), $CH_2$-(n-$C_6F_{13}$), $CH_2$—$CF(CF_3)_2$, $CH_2$—$C(CF_3)_3$, $CH_2$—$CF_2CF(CF_3)_2$, $CH_2$—$CF(CF_3)(C_2F_5)$, $CH_2$—$CH_2$—$CF_3$, $CH_2$—$CH_2$—$C_2F_5$, $CH_2$—$CH_2$-(n-$C_3F_7$), $CH_2$—$CH_2$-(n-$C_4F_9$), $CH_2$—$CH_2$-(n-$C_5F_{11}$), $CH_2$—$CH_2$-(n-$C_6F_{13}$), $CH_2$—$CH_2$—$CF(CF_3)_2$, $CH_2$—$CH_2$—$C(CF_3)_3$, $CH_2$—$CH_2$—$CF_2CF(CF_3)_2$ and $CH_2$—$CH_2$—$CF(CF_3)(C_2F_5)$.

In a special embodiment, the afore-mentioned fluorinated radicals $R^3$ and $R^4$ have the same meaning.

$R^3$ and $R^4$ are preferably both $CH_2$—$CF_3$, $CH_2$—$C_2F_5$ or $CH_2$-(n-$C_3F_7$).

Preferably, $R^3$ and $R^4$ have the same meaning and are both 2-ethylhexyl, 2-ethylheptyl, 2-ethyloctyl, 2-ethylnonyl or 2-ethyldecyl.

In a preferred embodiment $R^5$, $R^6$, $R^7$, $R^8$, $R^9$, $R^{10}$, $R^{11}$ and $R^{12}$ are all hydrogen.

In a further preferred embodiment $R^5$, $R^6$, $R^8$, $R^9$, $R^{10}$ and $R^{12}$ are all hydrogen and $R^7$ and $R^{11}$ are Cl.

In a further preferred embodiment $R^5$, $R^6$, $R^8$, $R^9$, $R^{10}$ and $R^{12}$ are all hydrogen and $R^7$ and $R^{11}$ are F.

In a further preferred embodiment $R^5$, $R^6$, $R^8$, $R^9$, $R^{10}$ and $R^{12}$ are all hydrogen and $R^7$ and $R^{11}$ are Br.

In a further preferred embodiment $R^5$, $R^6$, $R^8$, $R^9$, $R^{10}$ and $R^{12}$ are all hydrogen and $R^7$ and $R^{11}$ are CN.

In a further preferred embodiment $R^5$, $R^7$, $R^9$ and $R^{11}$ are hydrogen and $R^6$, $R^8$, $R^{10}$ and $R^{12}$ are $CF_3$.

Some particularly preferred compounds (I) are specified below:

(1)
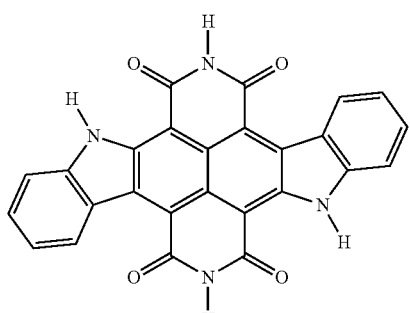

(2)
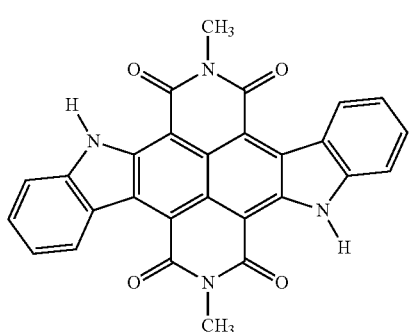

(3)
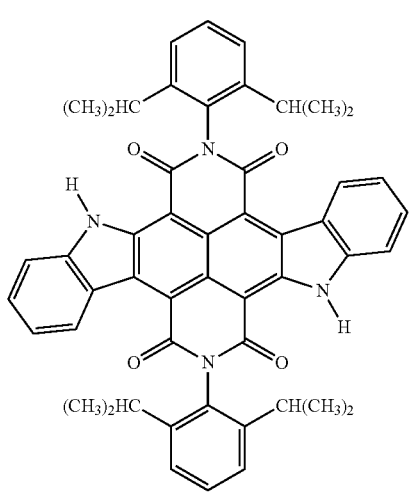

(4)
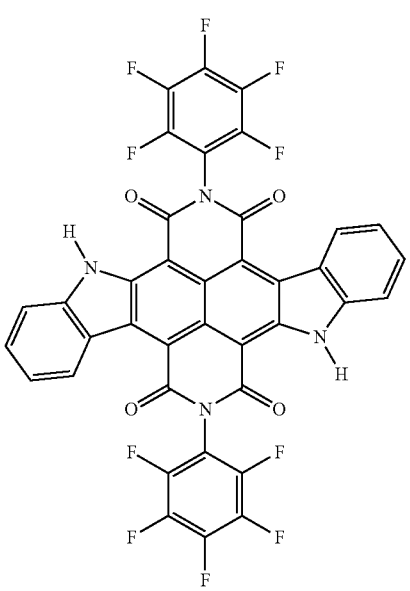

(5)
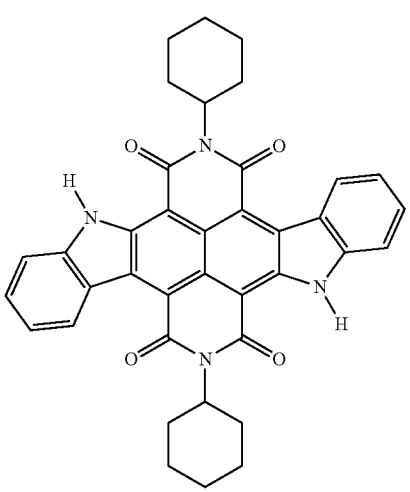

(6)
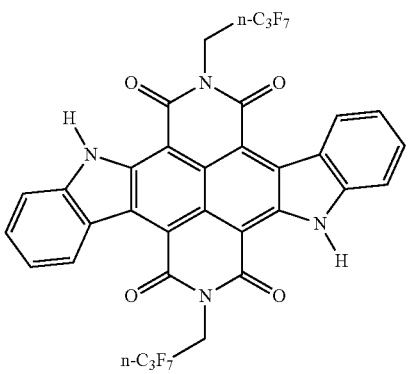

(7)
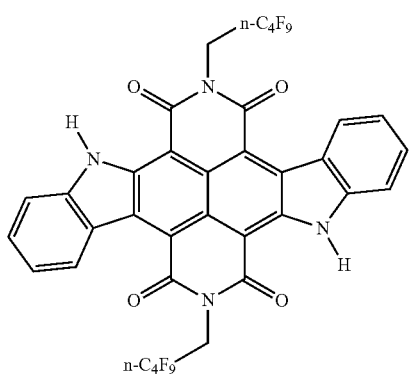
(8)
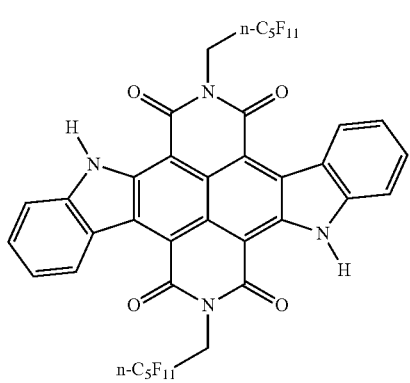
(9)
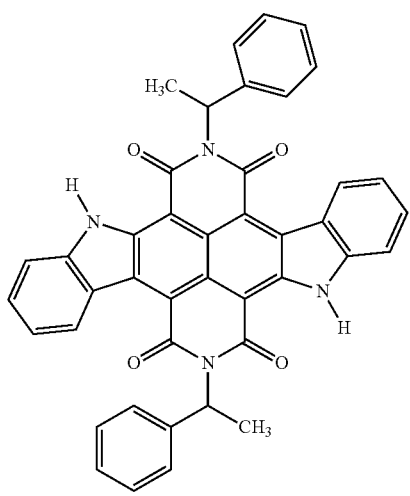
(10)
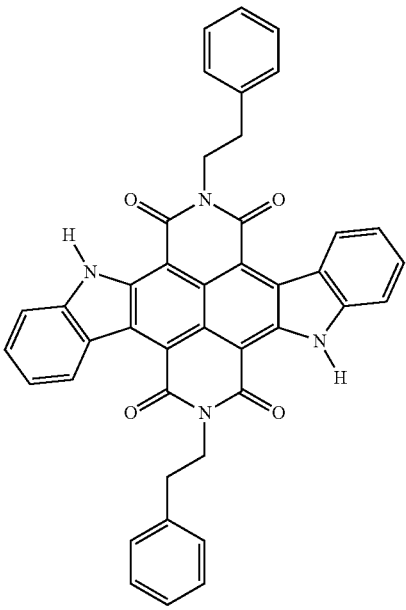
(11)
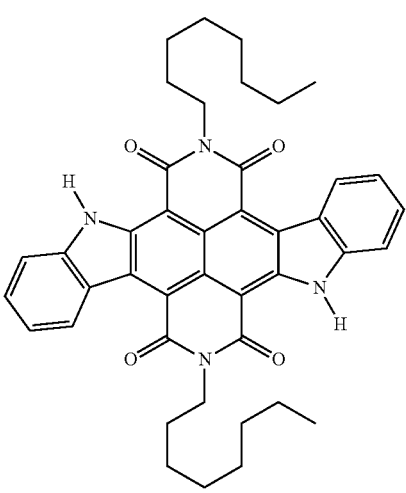

-continued
(12)
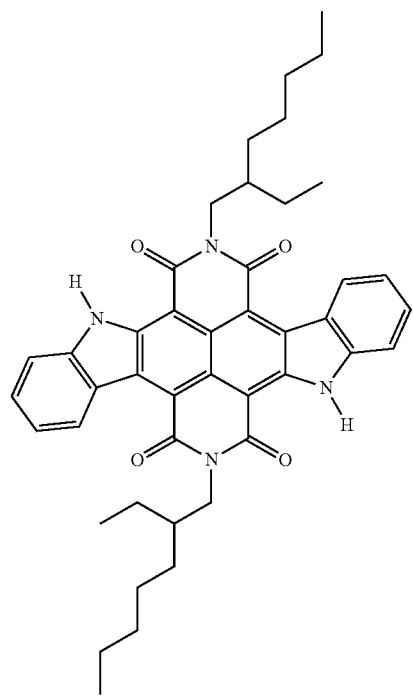
(13)
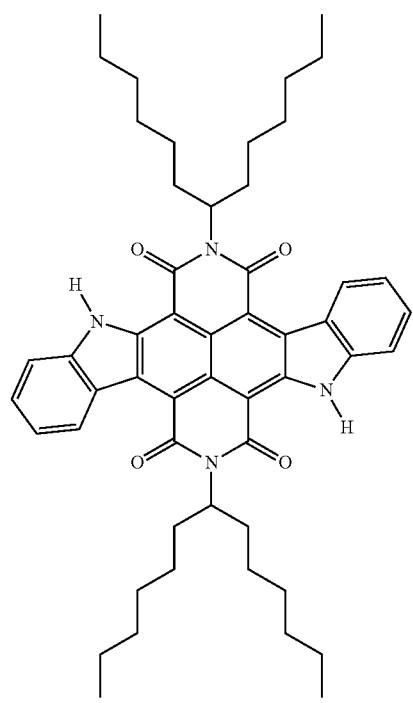
(14)
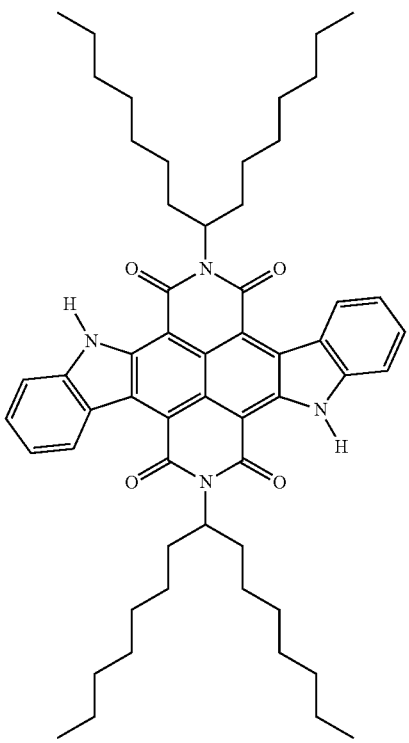
(15)
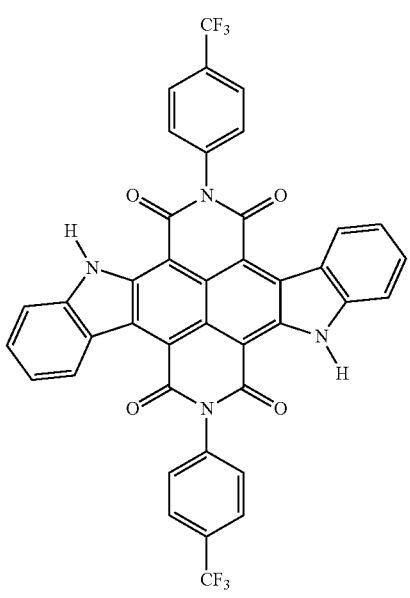

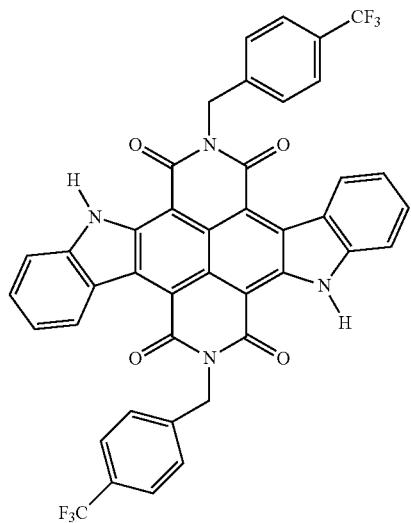
(16)
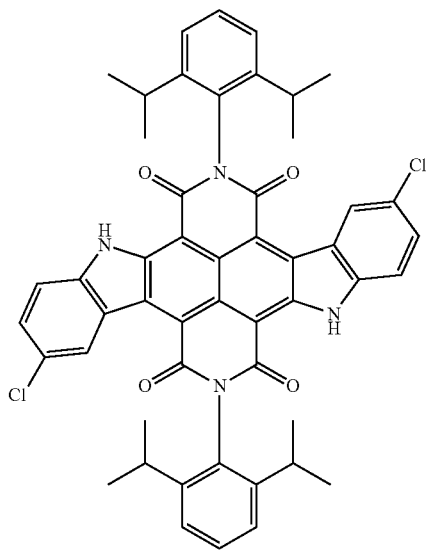
(18)
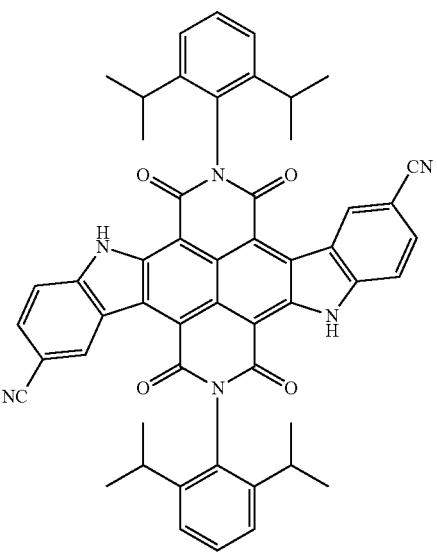
(19)
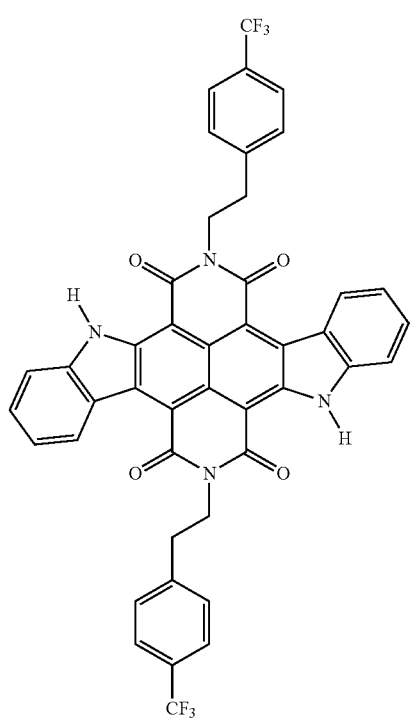
(17)
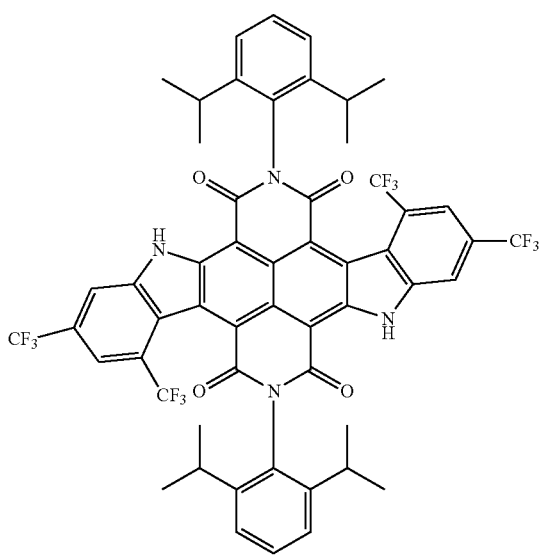
(20)

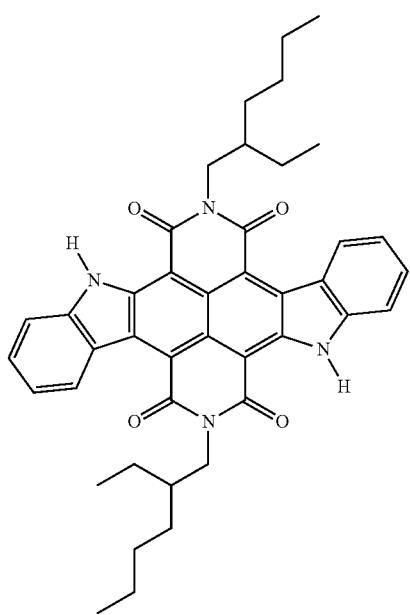

The invention further provides a process for preparing compounds of the formula I. In principle, the compounds of the formula I can be prepared by a transition metal catalyzed coupling reaction that can be formally regarded as a combination of a Buchwald-Hartwig amination and direct arylation:

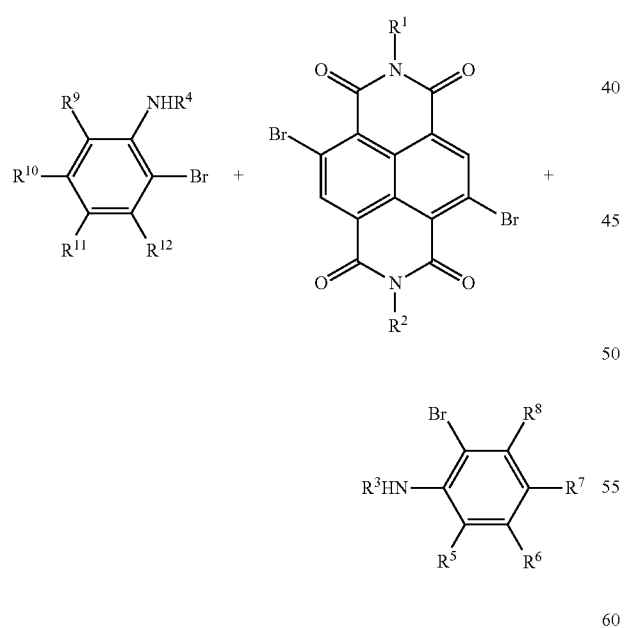

In a special embodiment, the 2,6-dibromonaphthalene-1,4,5,8-tetracarboxylic acid bisimide is reacted with only one type of 2-bromo-aminophenyl compound (i.e. $R^5=R^9$, $R^6=R^{10}$, $R^7=R^{11}$, and $R^9=R^{12}$).

A further object of the invention is a process for the preparation of a compound of the formula I,

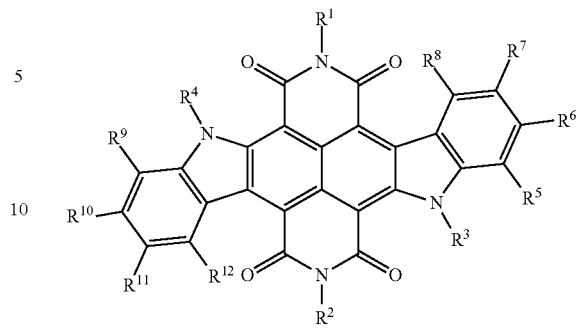

wherein $R^1$ and $R^2$ are each independently selected from hydrogen and in each case unsubstituted or substituted alkyl, cycloalkyl, heterocycloalkyl, aryl and hetaryl, $R^3$ and $R^4$ are each independently selected from hydrogen and in each case unsubstituted or substituted alkyl, cycloalkyl, heterocycloalkyl, aryl and hetaryl, $R^5$, $R^6$, $R^7$, $R^8$, $R^9$, $R^{10}$, $R^{11}$ and $R^{12}$ are independently selected from hydrogen, in each case unsubstituted or substituted alkyl, alkoxy, alkylthio, (monoalkyl)amino, (dialkyl)amino, cycloalkyl, cycloalkoxy, cycloalkylthio, (monocycloalkyl)amino, (dicycloalkyl)amino, heterocycloalkyl, heterocycloalkoxy, heterocycloalkylthio, (monoheterocycloalkyl)amino, (diheterocycloalkyl)amino, aryl, aryloxy, arylthio, (monoaryl)amino, (diaryl)amino, hetaryl, hetaryloxy, hetarylthio, (monohetaryl)amino, (dihetaryl)amino, halogen, hydroxy, mercapto, cyano, nitro, cyanato, thiocyanato, formyl, acyl, carboxy, carboxylate, alkylcarbonyloxy, carbamoyl, alkylaminocarbonyl, dialkylaminocarbonyl, sulfo, sulfonate, sulfoamino, sulfamoyl, alkylsulfonyl, arylsulfonyl, amidino, $NE^1E^2$ where $E^1$ and $E^2$ are each independently hydrogen, alkyl, cycloalkyl, heterocycloalkyl, aryl or hetaryl, in which a 2,6-dibromonaphthalene-1,4,5,8-tetracarboxylic acid bisimide of the formula (II)

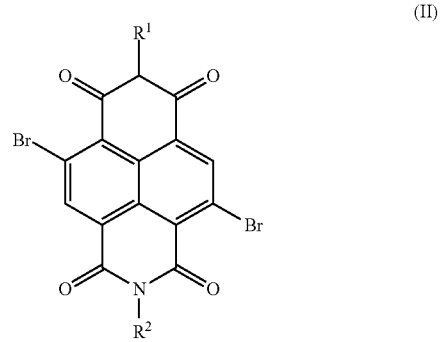

wherein $R^1$ and $R^2$ have the afore-mentioned meaning, is subjected to a reaction with a compound of the formula (IIIa) and, optionally, a different compound of the formula (IIIb)

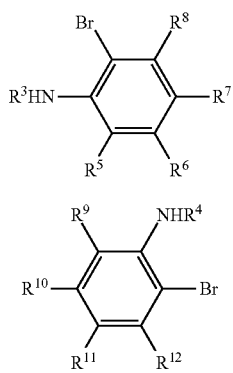

(IIIa)

(IIIb)

wherein
$R^3$, $R^4$, $R^5$, $R^6$, $R^7$, $R^8$, $R^9$, $R^{10}$, $R^{11}$ and $R^{12}$ have the afore-mentioned meaning.

A suitable route for the synthesis of 2,6-dibromonaphthalene-1,4,5,8-tetracarboxylic acid bisimides (II) is described in WO 2007/074137. The synthesis of N,N'-Di-(2',6'-diisopropylphenyl)-2,6-dibromonaphthalene-1,4,5,8-tetracarboxylic acid bisimide is described by S. Chopin et al. in J. Mater. Chem. 2007, 17, 4139-4146. A suitable educt for the synthesis of 2,6-dibromonaphthalene-1,4,5,8-tetracarboxylic acid bisimides (II) is 2,6-dibromonaphthalene-1,4,5,8-tetracarboxylic acid dianhydride. The synthesis of this compound is described in WO 2007/074137 and by C. Thalacker et al. in J. Org. Chem. 2006, 71, 8098-8105. The disclosure of the afore-mentioned documents is incorporated here by reference.

Preferably, the 2,6-dibromonaphthalene-1,4,5,8-tetracarboxylic acid bisimide (II) is reacted with the compound (IIIa) and optionally (IIIb) in the presence of a transition metal catalyst.

Suitable transition metal catalysts are especially palladium compounds and complexes complexes, such as palladium(II)acetate, [1,2-bis(diphenylphosphino)ethane]-palladium(II) chloride, [1,1'-bis(diphenylphosphino)-ferrocene] palladium(II) chloride, bis(triethylphosphine)palladium(II) chloride, bis(tricyclohexylphosphine)palladium(II) acetate, (2,2'-bipyridyl)palladium(II) chloride, bis(triphenylphosphine)palladium(II) chloride, tris(dibenzylideneacetone)dipalladium(0), 1,5-cyclooctadienepalladium(II) chloride, bis(acetonitrile)palladium(II) chloride and bis(benzonitrile)palladium(II) chloride, tetrakis(triphenylphosphine)palladium(0), tetrakis(tris-o-tolylphosphine)-palladium(0).

The reaction is preferably performed in the presence of a base. Preferably the base is selected from an alkali metal hydroxide, earth alkali metal hydroxide, alkali metal carbonate, earth alkali metal carbonate, thallium(I) hydroxide, thallium (I) alkanolate, alkali metal phosphate, alkali metal fluoride, alkali metal bis(trimethylsilyl)amides.

Examples for suitable bases are NaOH, KOH, $Na_2CO_3$, $K_2CO_3$, $Cs_2CO_3$, $Ba(OH)_2$, $K_3PO_4$, TlOH, thallium(I) ethoxide, KF, CsF, $(C_4H_9)_4NF$, sodium ethoxide, potassium ethoxide, potassium tert-butoxide, lithium bis(trimethylsilyl)amide (LiHMDS), sodium bis(trimethylsilyl)amide and potassium bis(trimethylsilyl)amide.

Suitable solvents are nonpolar and polar aprotic solvents, such as hydrocarbons, for example benzene, toluene, xylene, mesitylene, petroleum ether, decalin, etc. nitrogen-containing heterocycles, N,N-disubstituted aliphatic carboxamides (preferably N,N-di($C_1$-$C_4$-alkyl)($C_1$-$C_4$)carboxamides) and N-alkyllactams such as dimethylformamide, diethylformamide, dimethylacetamide, dimethylbutyramide and N-methylpyrrolidone; tetrahydrofuran, 1,4-dioxane.

The reaction temperature is generally from ambient temperature to 300° C., preferably from 60 to 250° C.

In a preferred embodiment, the reaction in reaction is performed under a protective gas atmosphere, for example nitrogen or argon.

The compounds of the formula (I) are in particular suitable as organic semiconductors. They generally can function as n-semiconductors or p-semiconductors. If a compound of the formula (I) acts as n-semiconductor or as p-semiconductors depends inter alia on the employed gate dielectric. If the gate dielectric comprises a self-assembled monolayer (SAM) of a fluorine-free compound, e.g. octadecylphosphonic acid, the compounds of the formula (I) usually act as n-semiconductor. If the gate dielectric comprises a self-assembled monolayer (SAM) of a fluorine-containing compound, e.g. 12,12,13,13,14,14,15,15,16,16,17,17,18,18-pentadecafluorooctadecylphosphonic acid, the compounds of the formula (I) usually act as p-semiconductor.

In electronic devices that employ a combination of two different semiconductors, e.g. organic solar cells, it depends on the position of the energy levels in the corresponding semiconductor material if a compound of the formula (I) acts as n-semiconductor or as p-semiconductor.

The compounds of the formula (I) have at least one of the following advantages over known organic semiconductor materials:
high charge transport mobility,
air stability,
high on/off ratio,
suitability to be employed in a solvent-based process.

The compounds of the formula (I) are advantageously suitable for organic field-effect transistors. They may be used, for example, for the production of integrated circuits (ICs), for which customary n-channel MOSFETs (metal oxide semiconductor field-effect transistors) have been used to date. These are then CMOS-like semiconductor units, for example for microprocessors, microcontrollers, static RAM and other digital logic circuits. For the production of semiconductor materials, the compounds of the formula (I) can be processed further by one of the following processes: printing (offset, flexographic, gravure, screenprinting, inkjet, electrophotography), evaporation, laser transfer, photolithography, drop-casting. They are especially suitable for use in displays (specifically large-surface area and/or flexible displays), RFID tags, smart labels and sensors.

The compounds of the formula (I) are advantageously suitable as electron conductors in organic field-effect transistors, organic solar cells and in organic light-emitting diodes. They are also particularly advantageous as an exciton transport material in excitonic solar cells.

Some of the compounds of the formula (I) are fluorescent and are also particularly advantageously suitable as fluorescent dyes in a display based on fluorescence conversion. Such displays comprise generally a transparent substrate, a fluorescent dye present on the substrate and a radiation source. Typical radiation sources emit blue (color by blue) or UV light (color by UV). The dyes absorb either the blue or the UV light and are used as green emitters. In these displays, for example, the red light is generated by exciting the red emitter by means of a green emitter which absorbs blue or UV light. Suitable color-by-blue displays are described, for example, in WO 98/28946. Suitable color-by-UV displays are described, for example, by W. A. Crossland, I. D. Sprigle and A. B. Davey in Photoluminescent LCDs (PL-LCD) using phosphors, Cambridge University and Screen Technology Ltd., Cambridge, UK. The compounds of the formula (I) are also particularly suitable in displays which, based on an electrophoretic effect, switch colors on and off via charged pigment dyes. Such electrophoretic displays are described, for example, in US 2004/0130776.

The invention further provides organic field-effect transistors comprising a substrate with at least one gate structure, a source electrode and a drain electrode, and at least one compound of the formula (I) as defined above as a semiconductor.

The invention further provides substrates having a plurality of organic field-effect transistors, wherein at least some of the field-effect transistors comprise at least one compound of the formula (I) as defined above.

The invention also provides semiconductor units which comprise at least one such substrate.

A specific embodiment is a substrate with a pattern (topography) of organic field-effect transistors, each transistor comprising
an organic semiconductor disposed on the substrate;
a gate structure for controlling the conductivity of the conductive channel; and
conductive source and drain electrodes at the two ends of the channel,
the organic semiconductor consisting of at least one compound of the formula (I) or comprising a compound of the formula (I). In addition, the organic field-effect transistor generally comprises a dielectric.

A specific embodiment is a substrate with a pattern (topography) of organic field-effect transistors, each transistor comprising
an organic semiconductor disposed on a buffer layer on a substrate;
a gate structure for controlling the conductivity of the conductive channel; and
conductive source and drain electrodes at the two ends of the channel,
the organic semiconductor consisting of at least one compound of the formula (I) or comprising a compound of the formula (I). In addition, the organic field-effect transistor generally comprises a dielectric.

As a buffer layer, any dielectric material is suitable, for example anorganic materials such LIF, $AlO_x$, $SiO_2$ or silicium nitride or organic materials such as polyimides or polyacrylates, e.g. polymethylmethacrylate (PMMA).

A further specific embodiment is a substrate having a pattern of organic field-effect transistors, each transistor forming an integrated circuit or being part of an integrated circuit and at least some of the transistors comprising at least one compound of the formula (I).

Suitable substrates are in principle the materials known for this purpose. Suitable substrates comprise, for example, metals (preferably metals of groups 8, 9, 10 or 11 of the Periodic Table, such as Au, Ag, Cu), oxidic materials (such as glass, ceramics, $SiO_2$, especially quartz), semiconductors (e.g. doped Si, doped Ge), metal alloys (for example based on Au, Ag, Cu, etc.), semiconductor alloys, polymers (e.g. polyvinyl chloride, polyolefins, such as polyethylene and polypropylene, polyesters, fluoropolymers, polyamides, polyimides, polyurethanes, polyethersulfones, polyalkyl (meth)acrylates, polystyrene and mixtures and composites thereof), inorganic solids (e.g. ammonium chloride), paper and combinations thereof. The substrates may be flexible or inflexible, and have a curved or planar geometry, depending on the desired use.

A typical substrate for semiconductor units comprises a matrix (for example a quartz or polymer matrix) and, optionally, a dielectric top layer.

Suitable dielectrics are $SiO_2$, polystyrene, poly-α-methylstyrene, polyolefins (such as polypropylene, polyethylene, polyisobutene), polyvinylcarbazole, fluorinated polymers (e.g. Cytop), cyanopullulans (e.g. CYMM), polyvinylphenol, poly-p-xylene, polyvinyl chloride, or polymers crosslinkable thermally or by atmospheric moisture. Specific dielectrics are "self-assembled nanodielectrics", i.e. polymers which are obtained from monomers comprising SiCl functionalities, for example $Cl_3SiOSiCl_3$, $Cl_3Si$—$(CH_2)_6$—$SiCl_3$, $Cl_3Si$—$(CH_2)_{12}$—$SiCl_3$, and/or which are crosslinked by atmospheric moisture or by addition of water diluted with solvents (see, for example, Facchetti, Adv. Mater. 2005, 17, 1705-1725). Instead of water, it is also possible for hydroxyl-containing polymers such as polyvinylphenol or polyvinyl alcohol or copolymers of vinylphenol and styrene to serve as crosslinking components. It is also possible for at least one further polymer to be present during the crosslinking operation, for example polystyrene, which is then also crosslinked (see Facietti, US patent application 2006/0202195).

The substrate may additionally have electrodes, such as gate, drain and source electrodes of OFETs, which are normally localized on the substrate (for example deposited onto or embedded into a nonconductive layer on the dielectric). The substrate may additionally comprise conductive gate electrodes of the OFETs, which are typically arranged below the dielectric top layer (i.e. the gate dielectric).

In a specific embodiment, an insulator layer (gate insulating layer) is present on at least part of the substrate surface. The insulator layer comprises at least one insulator which is preferably selected from inorganic insulators, such as $SiO_2$, silicon nitride ($Si_3N_4$), etc., ferroelectric insulators, such as $Al_2O_3$, $Ta_2O_5$, $La_2O_5$, $TiO_2$, $Y_2O_3$, etc., organic insulators such as polyimides, benzocyclobutene (BCB), polyvinyl alcohols, polyacrylates, etc., and combinations thereof.

Suitable materials for source and drain electrodes are in principle electrically conductive materials. These include metals, preferably metals of groups 6, 7, 8, 9, 10 or 11 of the Periodic Table, such as Pd, Au, Ag, Cu, Al, Ni, Cr, etc. Also suitable are conductive polymers, such as PEDOT (=poly (3,4-ethylenedioxythiophene)):PSS (=poly(styrenesulfonate)), polyaniline, surface-modified gold, etc. Preferred electrically conductive materials have a specific resistance of less than $10^{-3}$ ohm×meter, preferably less than $10^{-4}$ ohm×meter, especially less than $10^{-6}$ or $10^{-7}$ ohm×meter.

In a specific embodiment, drain and source electrodes are present at least partly on the organic semiconductor material. It will be appreciated that the substrate may comprise further components as used customarily in semiconductor materials or ICs, such as insulators, resistors, capacitors, conductor tracks, etc.

The electrodes may be applied by customary processes, such as evaporation or sputtering, lithographic processes or another structuring process, such as printing techniques.

The semiconductor materials may also be processed with suitable auxiliaries (polymers, surfactants) in disperse phase by printing.

In a first preferred embodiment, the deposition of at least one compound of the general formula (I) (and if appropriate further semiconductor materials) is carried out by a gas phase deposition process (physical vapor deposition, PVD). PVD processes are performed under high-vacuum conditions and comprise the following steps: evaporation, transport, deposition. It has been found that, surprisingly, the compounds of the general formula (I) are suitable particularly advantageously for use in a PVD process, since they essentially do not decompose and/or form undesired by-products. The material deposited is obtained in high purity. In a specific embodiment, the deposited material is obtained in the form of crystals or comprises a high crystalline content. In general, for the PVD, at least one compound of the general formula (I) is heated to a temperature above its evaporation temperature and deposited on a substrate by cooling below the crystallization temperature. The temperature of the substrate in the deposition is preferably within a range from about 20 to 250° C., more preferably from 50 to 200° C. It has been found that, surprisingly, elevated substrate temperatures in the deposition of the compounds of the formula (I) can have advantageous effects on the properties of the semiconductor elements achieved.

The resulting semiconductor layers generally have a thickness which is sufficient for forming a semiconductor channel which is in contact with the source/drain electrodes. The deposition can be effected under an inert atmosphere, for example, under nitrogen, argon or helium.

The deposition is effected typically at ambient pressure or under reduced pressure. A suitable pressure range is from about $10^{-7}$ to 1.5 bar.

The compound of the formula (I) is preferably deposited on the substrate in a thickness of from 10 to 1000 nm, more preferably from 15 to 250 nm. In a specific embodiment, the compound of the formula (I) is deposited at least partly in crystalline form. For this purpose, especially the above-described PVD process is suitable. Moreover, it is possible to use previously prepared organic semiconductor crystals. Suitable processes for obtaining such crystals are described by R. A. Laudise et al. in "Physical Vapor Growth of Organic Semi-Conductors", Journal of Crystal Growth 187 (1998), pages 449-454, and in "Physical Vapor Growth of Centimeter-sized Crystals of α-Hexathiophene", Journal of Crystal Growth 1982 (1997), pages 416-427, which are incorporated here by reference.

In a second preferred embodiment, the deposition of at least one compound of the general formula (I) (and if appropriate further semiconductor materials) is effected by spin-coating. Surprisingly, it is thus also possible to use the compounds of the formula (I) used in accordance with the invention in a wet processing method to produce semiconductor substrates. The compounds of the formula (I) should thus also be suitable for producing semiconductor elements, especially OFETs or based on OFETs, by a printing process. It is possible for this purpose to use customary printing or coating processes (inkjet, flexographic, offset, gravure; intaglio printing, nanoprinting, slot die). Preferred solvents for the use of compounds of the formula (I) in a printing process are aromatic solvents, such as toluene, xylene, etc. It is also possible to add thickening substances, such as polymers, for example polystyrene, etc., to these "semiconductor inks". In this case, the dielectrics used are the aforementioned compounds.

In a preferred embodiment, the inventive field-effect transistor is a thin-film transistor (TFT). In a customary construction, a thin-film transistor has a gate electrode disposed on the substrate or buffer layer (the buffer layer being part of the substrate), a gate insulation layer disposed thereon and on the substrate, a semiconductor layer disposed on the gate insulator layer, an ohmic contact layer on the semiconductor layer, and a source electrode and a drain electrode on the ohmic contact layer.

In a preferred embodiment, the surface of the substrate, before the deposition of at least one compound of the general formula (I) (and if appropriate of at least one further semiconductor material), is subjected to a modification. This modification serves to form regions which bind the semiconductor materials and/or regions on which no semiconductor materials can be deposited. The surface of the substrate is preferably modified with at least one compound (C1) which is suitable for binding to the surface of the substrate and to the compounds of the formula (I). In a suitable embodiment, a portion of the surface or the complete surface of the substrate is coated with at least one compound (C1) in order to enable improved deposition of at least one compound of the general formula (I) (and if appropriate further semiconductive compounds). A further embodiment comprises the deposition of a pattern of compounds of the general formula (C1) on the substrate by a corresponding production process. These include the mask processes known for this purpose and so-called "patterning" processes, as described, for example, in U.S. Ser. No. 11/353,934, which is incorporated here fully by reference.

Suitable compounds of the formula (C1) are capable of a binding interaction both with the substrate and with at least one semiconductor compound of the general formula (I). The term "binding interaction" comprises the formation of a chemical bond (covalent bond), ionic bond, coordinative interaction, van der Waals interactions, e.g. dipole-dipole interactions etc.), and combinations thereof. Suitable compounds of the general formula (C1) are:

silane, phosphonic acids, carboxylic acids, hydroxamic acids, such as alkyltrichlorosilanes, e.g. n-octadecyltrichlorosilane; compounds with trialkoxysilane groups, e.g. alkyltrialkoxysilanes such as n-octadecyl-trimethoxysilane, n-octadecyltriethoxysilane, n-octadecyltri(n-propyl)oxysilane, n-octadecyltri(isopropyl)oxysilane; trialkoxyaminoalkylsilanes, such as triethoxyaminopropylsilane and N[(3-triethoxysilyl)propyl]ethylenediamine; trialkoxyalkyl 3-glycidyl ether silanes, such as triethoxypropyl 3-glycidyl ether silane; trialkoxyallylsilanes, such as allyltrimethoxysilane; trialkoxy(isocyanatoalkyl)silanes; trialkoxysilyl (meth)acryloyloxyalkanes and trialkoxysilyl(meth)acrylamidoalkanes, such as 1-triethoxysilyl-3-acryloyl-oxypropane.

amines, phosphines and sulfur-comprising compounds, especially thiols.

The compound (C1) is preferably selected from alkyltrialkoxysilanes, especially n-octadecyltrimethoxysilane, n-octadecyltriethoxysilane; hexaalkyldisilazanes, and especially hexamethyldisilazane (HMDS); $C_8$-$C_{30}$-alkylthiols, especially hexadecanethiol; mercaptocarboxylic acids and mercaptosulfonic acids, especially mercaptoacetic acid, 3-mercaptopropionic acid, mercaptosuccinic acid, 3-mercapto-1-propanesulfonic acid and the alkali metal and ammonium salts thereof.

Various semiconductor architectures comprising the inventive semiconductors are also conceivable, for example top contact, top gate, bottom contact, bottom gate, or else a vertical construction, for example a VOFET (vertical organic field-effect transistor), as described, for example, in US 2004/0046182.

Preferred semiconductor architectures are the following, depicted in FIG. 3:

1. substrate, dielectric, organic semiconductor, preferably gate, dielectric, organic semiconductor, source and drain, known as "Bottom Gate Top Contact";
2. substrate, dielectric, organic semiconductor, preferably substrate, gate, dielectric, source and drain, organic semiconductor, known as "Bottom Gate Bottom Contact";
3. substrate, organic semiconductor, dielectric, preferably substrate, source and drain, organic semiconductor, dielectric, gate, known as "Top Gate Bottom Contact";
4. substrate, organic semiconductor, dielectric, preferably substrate, organic semiconductor, source and drain, dielectric, gate, known as "Top Gate Top Contact";

The layer thicknesses are, for example, from 10 nm to 5 μm in semiconductors, from 50 nm to 10 μm in the dielectric; the electrodes may, for example, be from 20 nm to 10 μm. The OFETs may also be combined to form other components, such as ring oscillators or inverters.

A further aspect of the invention is the provision of electronic components which comprise a plurality of semiconductor components, which may be n- and/or p-semiconductors. Examples of such components are field-effect transistors (FETs), bipolar junction transistors (BJTs), tunnel diodes, converters, light-emitting components, biological and chemical detectors or sensors, temperature-dependent detectors, photodetectors, such as polarization-sensitive photodetectors, gates, AND, NAND, NOT, OR, TOR and NOR gates, registers, switches, timer units, static or dynamic stores and other dynamic or sequential, logical or other digital components including programmable switches.

A specific semiconductor element is an inverter. In digital logic, the inverter is a gate which inverts an input signal. The inverter is also referred to as a NOT gate. Real inverter switches have an output current which constitutes the opposite of the input current. Typical values are, for example, (0, +5V) for TTL switches. The performance of a digital inverter reproduces the voltage transfer curve (VTC), i.e. the plot of input current against output current. Ideally, it is a staged function and, the closer the real measured curve approximates to such a stage, the better the inverter is. In a specific embodiment of the invention, the compounds of the formula (I) are used as organic semiconductors in an inverter.

The compounds of the formula (I) are also particularly advantageously suitable for use in organic photovoltaics (OPVs). Preference is given to their use in solar cells which are characterized by diffusion of excited states (exciton diffusion). In this case, one or both of the semiconductor materials utilized is notable for a diffusion of excited states (exciton mobility). Also suitable is the combination of at least one semiconductor material which is characterized by diffusion of excited states with polymers which permit conduction of the excited states along the polymer chain. In the context of the invention, such solar cells are referred to as excitonic solar cells. The direct conversion of solar energy to electrical energy in solar cells is based on the internal photo effect of a semiconductor material, i.e. the generation of electron-hole pairs by absorption of photons and the separation of the negative and positive charge carriers at a p-n transition or a Schottky contact. An exciton can form, for example, when a photon penetrates into a semiconductor and excites an electron to transfer from the valence band into the conduction band. In order to generate current, the excited state generated by the absorbed photons must, however, reach a p-n transition in order to generate a hole and an electron which then flow to the anode and cathode. The photovoltage thus generated can bring about a photocurrent in an external circuit, through which the solar cell delivers its power. The semiconductor can absorb only those photons which have an energy which is greater than its band gap. The size of the semiconductor band gap thus determines the proportion of sunlight which can be converted to electrical energy. Solar cells consist normally of two absorbing materials with different band gaps in order to very effectively utilize the solar energy. Most organic semiconductors have exciton diffusion lengths of up to 10 nm. There is still a need here for organic semiconductors through which the excited state can be passed on over very large distances. It has now been found that, surprisingly, the compounds of the general formula (I) described above are particularly advantageously suitable for use in excitonic solar cells.

Organic solar cells generally have a layer structure and generally comprise at least the following layers: anode, photoactive layer and cathode. These layers are generally applied to a substrate suitable for this purpose. The structure of organic solar cells is described, for example, in US 2005/0098726 and US 2005/0224905.

The invention provides an organic solar cell which comprises a substrate with at least one cathode and at least one anode, and at least one compound of the general formula (I) as defined above as a photoactive material. The inventive organic solar cell comprises at least one photoactive region. A photoactive region may comprise two layers, each of which has a homogeneous composition and forms a flat donor-acceptor heterojunction. A photoactive region may also comprise a mixed layer and form a donor-acceptor heterojunction in the form of a donor-acceptor bulk heterojunction. Organic solar cells with photoactive donor-acceptor transitions in the form of a bulk heterojunction are a preferred embodiment of the invention.

Suitable substrates for organic solar cells are, for example, oxidic materials, polymers and combinations thereof. Preferred oxidic materials are selected from glass, ceramic, $SiO_2$, quartz, etc. Preferred polymers are selected from polyethylene terephthalates, polyolefins (such as polyethylene and polypropylene), polyesters, fluoropolymers, polyamides, polyurethanes, polyalkyl (meth)acrylates, polystyrenes, polyvinyl chlorides and mixtures and composites.

Suitable electrodes (cathode, anode) are in principle metals, semiconductors, metal alloys, semiconductor alloys, nanowire thereof and combinations thereof. Preferred metals are those of groups 2, 8, 9, 10, 11 or 13 of the periodic table, e.g. Pt, Au, Ag, Cu, Al, In, Mg or Ca. Preferred semiconductors are, for example, doped Si, doped Ge, indium tin oxide (ITO), fluorinated tin oxide (FTO), gallium indium tin oxide (GITO), zinc indium tin oxide (ZITO), poly(3,4-ethylenedioxythiophene) poly(styrenesulfonate) (PEDOT-PSS), etc. Preferred metal alloys are, for example, alloys based on Pt, Au, Ag, Cu, etc. A specific embodiment is Mg/Ag alloys.

The material used for the electrode facing the light (the anode in a normal structure, the cathode in an inverse structure) is preferably a material at least partly transparent to the incident light. This preferably includes electrodes which have glass and/or a transparent polymer as a carrier material. Transparent polymers suitable as carriers are those mentioned above, such as polyethylene terephthalate. The electrical contact connection is generally effected by means of metal layers and/or transparent conductive oxides (TCOs). These preferably include ITO, doped ITO, FTO (fluorine doped tin oxide), AZO (aluminum doped tin oxide), ZnO, $TiO_2$, Ag, Au, Pt. Particular preference is given to ITO for contact connection. For electrical contact connection, it is also possible to use a conductive polymer, for example a poly-3,4-alkylenedioxy-thiophene, e.g. poly-3,4-ethyleneoxythiophene poly(styrenesulfonate) (PEDOT).

The electrode facing the light is configured such that it is sufficiently thin to bring about only minimal light absorption but thick enough to enable good charge transport of the extracted charge carriers. The thickness of the electrode layer (without carrier material) is preferably within a range from 20 to 200 nm.

In a specific embodiment, the material used for the electrode facing away from the light (the cathode in a normal structure, the anode in an inverse structure) is a material which at least partly reflects the incident light. This includes metal films, preferably of Ag, Au, Al, Ca, Mg, In, and mixtures thereof. Preferred mixtures are Mg/Al. The thickness of the electrode layer is preferably within a range from 20 to 300 nm.

The photoactive region comprises or consists of at least one layer which comprises at least one compound of the general formula (I) as defined above. In addition, the photoactive region may have one or more further layer(s). These are, for example, selected from layers with electron-conducting properties (electron transport layer, ETL), layers which comprise a hole-conducting material (hole transport layer, HTL), which need not absorb any radiation, exciton- and hole-blocking layers (e.g. EBLs), which must not absorb, and multiplication layers.

Suitable materials for these layers are described in detail hereinafter.

Suitable exciton- and hole-blocking layers are described, for example, in U.S. Pat. No. 6,451,415. Suitable materials for exciton-blocking layers are, for example, bathocuproin (BCP), 4,4',4''-tris[3-methylphenyl-N-phenylamino]triphenylamine (m-MTDATA).

The inventive solar cells comprise at least one photoactive donor-acceptor heterojunction. Optical excitation of an organic material generates excitons. In order that a photocurrent occurs, the electron-hole pair has to be separated, typically at a donor-acceptor interface between two unlike contact materials. At such an interface, the donor material forms a heterojunction with an acceptor material. When the charges are not separated, they can recombine in a process also known as "quenching", either radiatively by the emission of light of a lower energy than the incident light or nonradiatively by generation of heat. Both processes are undesired. According to the invention, at least one compound of the general formula (I) can be used as a charge generator (donor) or as electron acceptor material.

If at least one compound of the general formula (I) is used as a charge generator (donor) it can be combined with an appropriate electron acceptor material (ETM, electron transport material). Radiative excitation is followed by a rapid electron transfer to the ETM. Suitable ETMs are, for example, C60 and other fullerenes, perylene-3,4;9,10-bis (dicarboximides) (PTCDIs), or n-doped layers thereof (as described hereinafter). Preferred ETMs are C60 and other fullerenes or n-doped layers thereof.

In a first embodiment, the heterojunction has a flat configuration (see: Two layer organic photovoltaic cell, C. W. Tang, Appl. Phys. Lett., 48 (2), 183-185 (1986) or N. Karl, A. Bauer, J. Holzäpfel, J. Marktanner, M. Möbus, F. Stölzle, Mol. Cryst. Liq. Cryst., 252, 243-258 (1994).).

In a second embodiment, the heterojunction is configured as a bulk (mixed) heterojunction, also referred to as an interpenetrating donor-acceptor network. Organic photovoltaic cells with a bulk heterojunction are described, for example, by C. J. Brabec, N. S. Sariciftci, J. C. Hummelen in Adv. Funct. Mater., 11 (1), 15 (2001) or by J. Xue, B. P. Rand, S. Uchida and S. R. Forrest in J. Appl. Phys. 98, 124903 (2005). Bulk heterojunctions are discussed in detail hereinafter.

The compounds of the formula (I) can be used as a photoactive material in cells with MiM, pin, pn, Mip or Min structure (M=metal, p=p-doped organic or inorganic semiconductor, n=n-doped organic or inorganic semiconductor, i=intrinsically conductive system of organic layers; see, for example, J. Drechsel et al., Org. Electron., 5 (4), 175 (2004) or Maennig et al., Appl. Phys. A 79, 1-14 (2004)).

The compounds of the formula (I) can also be used as a photoactive material in tandem cells. Suitable tandem cells are described, for example, by P. Peumans, A. Yakimov, S. R. Forrest in J. Appl. Phys., 93 (7), 3693-3723 (2003) (see also U.S. Pat. No. 4,461,922, U.S. Pat. No. 6,198,091 and U.S. Pat. No. 6,198,092) and are described in detail hereinafter. The use of compounds of the general formula (I) in tandem cells is a preferred embodiment of the invention.

The compounds of the formula (I) can also be used as a photoactive material in tandem cells which are constructed from two or more than two stacked MiM, pin, Mip or Min structures (see DE 103 13 232.5 and J. Drechsel et al., Thin Solid Films, 451452, 515-517 (2004)).

The layer thickness of the M, n, i and p layers is typically within a range from 10 to 1000 nm, more preferably from 10 to 400 nm. The layers which form the solar cell can be produced by customary processes known to those skilled in the art. These include vapor deposition under reduced pressure or in an inert gas atmosphere, laser ablation or solution or dispersion processing methods such as spincoating, knifecoating, casting methods, spray application, dipcoating or printing (e.g. inkjet, flexographic, offset, gravure; intaglio, nanoimprinting). In a specific embodiment, the entire solar cell is produced by a gas phase deposition process.

In order to improve the efficiency of organic solar cells, it is possible to shorten the mean distance through which the exciton has to diffuse in order to arrive at the next donor-acceptor interface. To this end, it is possible to use mixed layers of donor material and acceptor material which form an interpenetrating network in which internal donor-acceptor heterojunctions are possible. This bulk heterojunction is a specific form of the mixed layer, in which the excitons generated need only travel a very short distance before they arrive at a domain boundary, where they are separated.

In a preferred embodiment, the photoactive donor-acceptor transitions in the form of a bulk heterojunction are produced by a gas phase deposition process (physical vapor deposition, PVD). Suitable processes are described, for example, in US 2005/0227406, to which reference is made here. To this end, a compound of the general formula (I) and a complementary semiconductor material can be subjected to a gas phase deposition in the manner of a cosublimation. PVD processes are performed under high-vacuum conditions and comprise the following steps: evaporation, transport, deposition. The deposition is effected preferably at a pressure within a range from about $10^{-2}$ mbar to $10^{-7}$ mbar, for example from $10^{-5}$ to $10^{-7}$ mbar. The deposition rate is preferably within a range from 0.01 to 100 nm/s. The deposition can be effected in an inert gas atmosphere, for example under nitrogen, helium or argon. The temperature of the substrate during the deposition is preferably within a range from −100 to 300° C., more preferably from −50 to 250° C.

The other layers of the organic solar cell can be produced by known processes. These include vapor deposition under reduced pressure or in an inert gas atmosphere, laser ablation, or solution or dispersion processing methods such as spincoating, knifecoating, casting methods, spray application, dipcoating or printing (e.g. inkjet, flexographic, offset, gravure; intaglio, nanoimprinting). In a specific embodiment, the entire solar cell is produced by a gas phase deposition process.

The photoactive layer (homogeneous layer or mixed layer) can be subjected to a thermal treatment directly after production thereof or after production of further layers which form the solar cell. Such a heat treatment can in many cases further improve the morphology of the photoactive layer. The temperature is preferably within a range from about 60° C. to 300° C. The treatment time is preferably within a range from 1 minute to 3 hours. In addition or alternatively to a thermal treatment, the photoactive layer (mixed layer) can be subjected to a treatment with a solvent-containing gas directly after production thereof or after production of further layers which form the solar cell. In a suitable embodiment, saturated solvent vapors in air are used at ambient temperature. Suitable solvents are toluene, xylene, chloroform, N-methylpyrrolidone, dimethylformamide, ethyl acetate, chlorobenzene, dichloromethane and mixtures thereof. The treatment time is preferably within a range from 1 minute to 3 hours.

In a suitable embodiment, the inventive solar cells are present as an individual cell with flat heterojunction and normal structure. In a specific embodiment, the cell has the following structure:

- an at least partly transparent conductive layer (top electrode, anode) (11)
- a hole-conducting layer (hole transport layer, HTL) (12)
- a layer which comprises a donor material (13)
- a layer which comprises an acceptor material (14)
- an exciton-blocking and/or electron-conducting layer (15)
- a second conductive layer (back electrode, cathode) (16)

The donor material preferably comprises at least one compound of the formula (I) or consists of a compound of the formula (I). The acceptor material preferably comprises at least one fullerene or fullerene derivative, or consists of a fullerene or fullerene derivative. The acceptor material preferably comprises C60 or PCBM ([6,6]-phenyl-C61-butyric acid methyl ester).

The essentially transparent conductive layer (11) (anode) comprises a carrier, such as glass or a polymer (e.g. polyethylene terephthalate) and a conductive material, as described above. Examples include ITO, doped ITO, FTO, ZnO, AZO, etc. The anode material can be subjected to a surface treatment, for example with UV light, ozone, oxygen plasma, $Br_2$, etc. The layer (11) should be sufficiently thin to enable maximum light absorption, but also sufficiently thick to ensure good charge transport. The layer thickness of the transparent conductive layer (11) is preferably within a range from 20 to 200 nm.

Solar cells with normal structure optionally have a hole-conducting layer (HTL). This layer comprises at least one hole-conducting material (hole transport material, HTM).

Layer (12) may be an individual layer of essentially homogeneous composition or may comprise two or more than two sublayers.

Hole-conducting materials (HTM) suitable for forming layers with hole-conducting properties (HTL) preferably comprise at least one material with high ionization energy. The ionization energy is preferably at least 5.0 eV, more preferably at least 5.5 eV. The materials may be organic or inorganic materials. Organic materials suitable for use in a layer with hole-conducting properties are preferably selected from poly(3,4-ethylenedioxythiophene)poly(styrenesulfonate) (PEDOT-PSS), Ir-DPBIC (tris-N,N'-diphenyl-benzimidazol-2-ylideneiridium(III)), N,N'-diphenyl-N,N'-bis(3-methylphenyl)-1,1'-diphenyl-4,4'-diamine (α-NPD), 2,2',7,7'-tetrakis(N,N-di-p-methoxyphenylamine)-9,9'-spirobifluorene (spiro-MeOTAD), etc. and mixtures thereof. The organic materials may, if desired, be doped with a p-dopant which has a LUMO within the same range as or lower than the HOMO of the hole-conducting material. Suitable dopants are, for example, 2,3,5,6-tetrafluoro-7,7,8,8-tetracyanoquinodimethane ($F_4TCNQ$), $WO_3$, $MoO_3$, etc. Inorganic materials suitable for use in a layer with hole-conducting properties are preferably selected from $WO_3$, $MoO_3$, etc.

If present, the thickness of the layers with hole-conducting properties is preferably within a range from 5 to 200 nm, more preferably 10 to 100 nm.

Layer (13) comprises at least one compound of the general formula (I). The thickness of the layer should be sufficient to absorb a maximum amount of light, but thin enough to enable effective dissipation of the charge. The thickness of the layer (13) is preferably within a range from 5 nm to 1 μm, more preferably from 5 to 100 nm.

Layer (14) comprises at least one acceptor material. The acceptor material preferably comprises at least one fullerene or fullerene derivative. Alternatively or additionally suitable acceptor materials are specified hereinafter. The thickness of the layer should be sufficient to absorb a maximum amount of light, but thin enough to enable effective dissipation of the charge. The thickness of the layer (14) is preferably within a range from 5 nm to 1 μm, more preferably from 5 to 80 nm.

Solar cells with normal structure optionally comprise an exciton-blocking and/or electron-conducting layer (15) (EBL/ETL). Suitable materials for exciton-blocking layers generally have a greater band gap than the materials of layer (13) and/or (14). They are firstly capable of reflecting excitons and secondly enable good electron transport through the layer. The materials for the layer (15) may comprise organic or inorganic materials. Suitable organic materials are preferably selected from 2,9-dimethyl-4,7-diphenyl-1,10-phenanthroline (BCP), 4,7-diphenyl-1,10-phenanthroline (Bphen), 1,3-bis[2-(2,2"-bipyridin-6-yl)-1,3,4-oxadiazo-5-yl]benzene (BPY-OXD), etc. The organic materials may, if desired, be doped with an n-dopant which has a HOMO within the same range as or lower than the LUMO of the electron-conducting material. Suitable dopants are, for example, $Cs_2CP_3$, Pyronin B (PyB), Rhodamine B, cobaltocenes, etc. Inorganic materials suitable for use in a layer with electron-conducting properties are preferably selected from ZnO, etc. If present, the thickness of the layer (15) is preferably within a range from 5 to 500 nm, more preferably 10 to 100 nm.

Layer 16 is the cathode and preferably comprises at least one compound with low work function, more preferably a metal such as Ag, Al, Mg, Ca, etc. The thickness of the layer (16) is preferably within a range from about 10 nm to 10 μm, e.g. 10 nm to 60 nm.

In a further suitable embodiment, the inventive solar cells are present as an individual cell with a flat heterojunction and inverse structure.

In a specific embodiment, the cell has the following structure:

- an at least partly transparent conductive layer (cathode) (11)
- an exciton-blocking and/or electron-conducting layer (12)
- a layer which comprises an acceptor material (13)
- a layer which comprises a donor material (14)
- a hole-conducting layer (hole transport layer, HTL) (15)
- a second conductive layer (back electrode, anode) (16)

With regard to suitable and preferred materials for the layers (11) to (16), reference is made to the above remarks regarding the corresponding layers in solar cells with normal structure.

In a further preferred embodiment, the inventive solar cells are present as an individual cell with normal structure and have a bulk heterojunction. In a specific embodiment, the cell has the following structure:

- an at least partly transparent conductive layer (anode) (21)
- a hole-conducting layer (hole transport layer, HTL) (22)
- a mixed layer which comprises a donor material and an acceptor material, which form a donor-acceptor heterojunction in the form of a bulk heterojunction (23)
- an electron-conducting layer (24)
- an exciton-blocking and/or electron-conducting layer (25)
- a second conductive layer (back electrode, cathode) (26)

The layer (23) comprises at least one compound of the general formula (I) as a photoactive material, e.g. as a donor material. The layer (23) additionally comprises a complementary semiconductor material, e.g. at least one fullerene or fullerene derivative as an acceptor material. The layer (23) comprises especially C60 or PCBM ([6,6]-phenyl-C61-butyric acid methyl ester) as an acceptor material.

With regard to layer (21), reference is made completely to the above remarks regarding layer (11).

With regard to layer (22), reference is made completely to the above remarks regarding layer (12).

Layer (23) is a mixed layer which comprises at least one compound of the general formula (I) as a semiconductor material. In addition, layer (23) comprises at least one complementary semiconductor material. As described above, the layer (23) can be produced by coevaporation or by solution processing using customary solvents. The mixed layer comprises preferably 10 to 90% by weight, more preferably 20 to 80% by weight, of at least one compound of the general formula (I), based on the total weight of the mixed layer. The mixed layer comprises preferably 10 to 90% by weight, more preferably 20 to 80% by weight, of at least one acceptor material, based on the total weight of the mixed layer. The thickness of the layer (23) should be sufficient to absorb a maximum amount of light, but thin enough to enable effective dissipation of the charge. The thickness of the layer (23) is preferably within a range from 5 nm to 1 µm, more preferably from 5 to 200 nm, especially 5 to 80 nm.

Solar cells with a bulk heterojunction comprise an electron-conducting layer (24) (ETL). This layer comprises at least one electron transport material (ETM). Layer (24) may be a single layer of essentially homogeneous composition or may comprise two or more than two sublayers. Suitable materials for electron-conducting layers generally have a low work function or ionization energy. The ionization energy is preferably not more than 3.5 eV. Suitable organic materials are preferably selected from the aforementioned fullerenes and fullerene derivatives, 2,9-dimethyl-4,7-diphenyl-1,10-phenanthroline (BCP), 4,7-diphenyl-1,10-phenanthroline (Bphen), 1,3-bis[2-(2,2'-bipyridin-6-yl)-1,3,4-oxadiazo-5-yl]benzene (BPY-OXD), etc. The organic materials used in layer (24) may, if desired, be doped with an n-dopant which has a HOMO within the same range as or lower than the LUMO of the electron-conducting material. Suitable dopants are, for example, $Cs_2CO_3$, Pyronin B (PyB), Rhodamine B, cobaltocenes, etc. The thickness of the layer (23) is, if present, preferably within a range from 1 nm to 1 µm, particularly 5 to 60 nm.

With regard to layer (25), reference is made completely to the above remarks regarding layer (15).

With regard to layer (26), reference is made completely to the above remarks regarding layer (16).

Solar cells with a donor-acceptor heterojunction in the form of a bulk heterojunction can be produced by a gas phase deposition process as described above. With regard to deposition rates, substrate temperature during the deposition and thermal aftertreatment, reference is made to the above remarks.

In a further preferred embodiment, the inventive solar cells are present as an individual cell with inverse structure and have a bulk heterojunction.

In a particularly preferred embodiment, the inventive solar cell is a tandem cell.

A tandem cell consists of two or more than two (e.g. 3, 4, 5, etc.) subcells. A single subcell, some of the subcells or all subcells may have photoactive donor-acceptor heterojunctions. Each donor-acceptor heterojunction may be in the form of a flat heterojunction or in the form of a bulk heterojunction. Preferably, at least one of the donor-acceptor heterojunctions is in the form of a bulk heterojunction. According to the invention, the photoactive layer of at least one subcell comprises a compound of the general formula (I). Preferably, the photoactive layer of at least one subcell comprises a compound of the general formula (I) and at least one fullerene or fullerene derivative. More preferably, the semiconductor mixture used in the photoactive layer of at least one subcell consists of a compound of the general formula (I) and $C_{60}$ or [6,6]-phenyl-C61-butyric acid methyl ester.

The subcells which form the tandem cell may be connected in parallel or in series. The subcells which form the tandem cell are preferably connected in series. There is preferably an additional recombination layer in each case between the individual subcells. The individual subcells have the same polarity, i.e. generally either only cells with normal structure or only cells with inverse structure are combined with one another.

FIG. 2 shows the basic structure of an inventive tandem cell. Layer 31 is a transparent conductive layer. Suitable materials are those specified above for the individual cells.

Layers 32 and 34 constitute subcells. "Subcell" refers here to a cell as defined above without cathode and anode. The subcells may, for example, either all have a compound of the general formula (I) used in accordance with the invention in the photoactive layer (preferably in combination with a fullerene or fullerene derivative, especially C60) or have other combinations of semiconductor materials, for example C60 with zinc phthalocyanine, C60 with oligothiophene (such as DCV5T). In addition, individual subcells may also be configured as dye-sensitized solar cells or polymer cells.

In all cases, preference is given to a combination of materials which exploit different regions of the spectrum of the incident light, for example of natural sunlight. For instance, the combination of a compound of the general formula (I) and fullerene or fullerene derivative used in accordance with the invention absorbs in the long-wave region of sunlight. Cells based on at least one perylene compound as described, for example, in European patent application 10166498.5, absorb primarily in the short-wave range. Thus, a tandem cell composed of a combination of these subcells should absorb radiation in the range from about 400 nm to 900 nm. Suitable combination of subcells should thus allow the spectral range utilized to be extended. For optimal performance properties, optical interference should be considered. For instance, subcells which absorb at relatively short wavelengths should be arranged closer to the metal top contact than subcells with longer-wave absorption.

With regard to layer (31), reference is made completely to the above remarks regarding layers (11) and (21).

With regard to layers (32) and (34), reference is made completely to the above remarks regarding layers (12) to (15) for flat heterojunctions and (22) to (25) for bulk heterojunctions.

Layer 33 is a recombination layer. Recombination layers enable the charge carriers from one subcell to recombine with those of an adjacent subcell. Small metal clusters are suitable, such as Ag, Au or combinations of highly n- and p-doped layers. In the case of metal clusters, the layer thickness is preferably within a range from 0.5 to 5 nm.

In the case of highly n- and p-doped layers, the layer thickness is preferably within a range from 5 to 40 nm. The recombination layer generally connects the electron-conducting layer of a subcell to the hole-conducting layer of an adjacent subcell. In this way, further cells can be combined to form the tandem cell.

Layer 36 is the top electrode. The material depends on the polarity of the subcells. For subcells with normal structure, preference is given to using metals with a low work function, such as Ag, Al, Mg, Ca, etc. For subcells with inverse structure, preference is given to using metals with a high work function, such as Au or Pt, or PEDOT-PSS.

In the case of subcells connected in series, the overall voltage corresponds to the sum of the individual voltages of all subcells. The overall current, in contrast, is limited by the lowest current of one subcell. For this reason, the thickness of each subcell should be optimized such that all subcells have essentially the same current.

Examples of different kinds of donor-acceptor heterojunctions are a donor-acceptor double layer with a flat heterojunction, or the heterojunction is configured as a hybrid planar-mixed heterojunction or gradient bulk heterojunction or annealed bulk heterojunction.

The production of a hybrid planar-mixed heterojunction is described in Adv. Mater. 17, 66-70 (2005). In this structure, mixed heterojunction layers which were formed by simultaneous evaporation of acceptor and donor material are present between homogeneous donor and acceptor material.

In a specific embodiment of the present invention, the donor-acceptor-heterojunction is in the form of a gradient bulk heterojunction. In the mixed layers composed of donor and acceptor materials, the donor-acceptor ratio changes gradually. The form of the gradient may be stepwise or linear. In the case of a stepwise gradient, the layer 01 consists, for example, of 100% donor material, layer 02 has a donor/acceptor ratio>1, layer 03 has a donor/acceptor ratio=1, layer 04 has a donor/acceptor ratio<1, and layer 05 consists of 100% acceptor material. In the case of a linear gradient, layer 01 consists, for example, of 100% donor material, layer 02 has a decreasing ratio of donor/acceptor, i.e. the proportion of donor material decreases in a linear manner in the direction of layer 03, and layer 03 consists of 100% acceptor material. The different donor-acceptor ratios can be controlled by means of the deposition rate of each and every material. Such structures can promote the percolation path for charges.

In a further specific embodiment of the present invention, the donor-acceptor heterojunction is configured as an annealed bulk heterojunction; see, for example, Nature 425, 158-162, 2003. The process for producing such a solar cell comprises an annealing step before or after the metal deposition. As a result of the annealing, donor and acceptor materials can separate, which leads to more extended percolation paths.

In a further specific embodiment of the present invention, the organic solar cells are produced by organic vapor phase deposition, either with a flat or a controlled heterojunction architecture. Solar cells of this type are described in Materials, 4, 2005, 37.

The organic solar cells of the invention preferably comprise at least one photoactive region which comprises at least one compound of the formula (I), which is in contact with at least one complementary semiconductor. In addition to compounds of the formula (I), the semiconductor materials listed hereinafter are suitable in principle for use in solar cells according to the invention.

Preferred further semiconductors are fullerenes and fullerene derivatives, preferably selected from $C_{60}$, $C_{70}$, $C_{84}$, phenyl-$C_{61}$-butyric acid methyl ester ([60]PCBM), phenyl-$C_{71}$-butyric acid methyl ester ([71]PCBM), phenyl-$C_{84}$-butyric acid methyl ester ([84]PCBM), phenyl-C61-butyric acid butyl ester ([60]PCBB), phenyl-$C_{61}$-butyric acid octyl ester ([60]PCBO), thienyl-$C_{61}$-butyric acid methyl ester ([60]ThCBM) and mixtures thereof. Particular preference is given to $C_{60}$, [60]PCBM and mixtures thereof. Preference is given to those fullerenes which are vaporizable, for example C60 or C70. Fullerenes and fullerene derivatives in combination with at least one compound of the formula (I) usually act as acceptors.

Suitable further semiconductors are perylendiimides of the formula

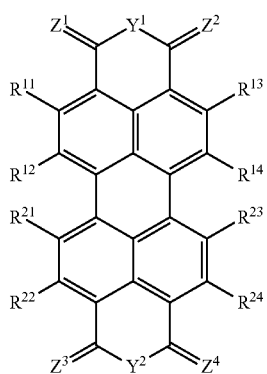

in which the $R^{11}$, $R^{12}$, $R^{13}$, $R^{14}$, $R^{21}R^{22}$, $R^{23}$ and $R^{24}$ radicals are each independently hydrogen, halogen or groups other than halogen, $Y^1$ is O or $NR^a$ where $R^a$ is hydrogen or an organyl radical, $Y^2$ is O or $NR^b$ where $R^b$ is hydrogen or an organyl radical, $Z^1$, $Z^2$, $Z^3$ and $Z^4$ are each O, where, in the case that $Y^1$ is $NR^a$, one of the $Z^1$ and $Z^2$ radicals may also be $NR^c$, where the $R^a$ and $R^c$ radicals together are a bridging group having 2 to 5 atoms between the flanking bonds, and where, in the case that $Y^2$ is $NR^b$, one of the $Z^3$ and $Z^4$ radicals may also be $NR^d$, where the $R^b$ and $R^d$ radicals together are a bridging group having 2 to 5 atoms between the flanking bonds.

Suitable perylendiimides are, for example, described in WO 2007/074137, WO 2007/093643 and WO 2007/116001, to which reference is made here.

Perylendiimides in combination with at least one compound of the formula (I) may act as donors or acceptors, depending inter alia on the substituents of the perylene diimides. Usually, perylendiimides in combination with at least one compound of the formula (I) act as acceptors, whereas perylendiimides with substituents that act as strong donors, e.g. aryloxy or amino groups, may also act as donors.

Further suitable semiconductors are thiophene compounds. These are preferably selected from thiophenes, oligothiophenes and substituted derivatives thereof. Suitable oligothiophenes are quaterthiophenes, quinquethiophenes, sexithiophenes, α,ω-di($C_1$-$C_8$)-alkyloligothiophenes, such as α,ω-dihexylquaterthiophenes, α,ω-dihexylquinquethiophenes and α,ω-dihexylsexithiophenes, poly(alkylthiophenes) such as poly(3-hexylthiophene), bis(dithienothiophenes), anthradithiophenes and dialkylanthradithiophenes such as dihexylanthradithiophene, phenylene-thiophene (P-T) oligomers and derivatives thereof, especially α,ω-alkyl-substituted phenylene-thiophene oligomers.

Further thiophene compounds suitable as semiconductors are preferably selected from compounds like
α,α'-bis(2,2-dicyanovinyl)quinquethiophene (DCV5T), (3-(4-octylphenyl)-2,2'-bithiophene) (PTOPT),
and acceptor-substituted oligothiophenes as described in WO 2006/092124.

Thiophene compounds in combination with at least one compound of the formula (I) usually act as donors.

Further semiconductors suitable as donors are merocyanines as described in WO 2010/049512.

All aforementioned semiconductors may be doped. The conductivity of semiconductors can be increased by chemical doping techniques using dopants. An organic semiconductor material may be doped with an n-dopant which has a HOMO energy level which is close to or higher than the LUMO energy level of the electron-conducting material. An organic semiconductor material may also be doped with a p-dopant which has a LUMO energy level which is close to or higher than the HOMO energy level of the hole-conducting material. In other words, in the case of n-doping an electron is released from the dopant, which acts as the donor, whereas in the case of p-doping the dopant acts as an acceptor which accepts an electron.

Suitable dopants for the compounds (I) according to the invention and for p-semiconductors in general are, for example, selected from $WO_3$, $MoO_3$, 2,3,5,6-tetrafluoro-7,7,8,8-tetracyanoquinodimethane ($F_4$-TCNQ), 3,6-difluoro-2,5,7,7,8,8-hexacyanoquinodimethane, dichlorodicyanoquinone (DDQ) or tetracyanoquinodimethane (TCNQ). A preferred dopant is 3,6-difluoro-2,5,7,7,8,8-hexacyanoquinodimethane.

Further suitable dopants are, for example, selected from $Cs_2CO_3$, LiF, Pyronin B (PyB), rhodamine derivatives, cobaltocenes, etc. Preferred dopants are Pyronin B and rhodamine derivatives, especially rhodamine B.

The dopants are typically used in an amount of up to 10 mol %, preferably up to mol %, based on the amount of the semiconductor to be doped.

The invention further provides an electroluminescent (EL) arrangement comprising an upper electrode, a lower electrode, wherein at least one of said electrodes is transparent, an electroluminescent layer and optionally an auxiliary layer, wherein the electroluminescent arrangement comprises at least one compound of the formula I as defined above. An EL arrangement is characterized by the fact that it emits light when an electrical voltage is applied with flow of current. Such arrangements have been known for a long time in industry and technology as light-emitting diodes (LEDs). Light is emitted on account of the fact that positive charges (holes) and negative charges (electrons) combine with the emission of light. In the sense of this application the terms electroluminescing arrangement and organic light-emitting diode (OLEDs) are used synonymously. As a rule, EL arrangements are constructed from several layers. At least on of those layers contains one or more organic charge transport compounds. The layer structure is in principle as follows:

1. Carrier, substrate
2. Base electrode (anode)
3. Hole-injecting layer
4. Hole-transporting layer
5. Light-emitting layer
6. Electron-transporting layer
7. Electron-injecting layer
8. Top electrode (cathode)
9. Contacts
10. Covering, encapsulation.

This structure represents the most general case and can be simplified by omitting individual layers, so that one layer performs several tasks. In the simplest case an EL arrangement consists of two electrodes between which an organic layer is arranged, which fulfils all functions, including emission of light. The structure of organic light-emitting diodes and processes for their production are known in principle to those skilled in the art, for example from WO 2005/019373. Suitable materials for the individual layers of OLEDs are disclosed, for example, in WO 00/70655. Reference is made here to the disclosure of these documents. In principle OLEDs according to the invention can be produced by methods known to those skilled in the art. In a first embodiment, an OLED is produced by successive vapor deposition of the individual layers onto a suitable substrate. For vapor deposition, it is possible to use customary techniques such as thermal evaporation, chemical vapor deposition and others. In an alternative embodiment, the organic layers may be coated from solutions or dispersions in suitable solvents, for which coating techniques known to those skilled in the art are employed.

Suitable as substrate 1 are transparent carriers, such as glass or plastics films (for example polyesters, such as polyethylene terephthalate or polyethylene naphthalate, polycarbonate, polyacrylate, polysulphone, polyimide foil). Suitable as transparent and conducting materials are a) metal oxide, for example indium-tin oxide (ITO), tin oxide (NESA), etc. and b) semi-transparent metal films, for example Au, Pt, Ag, Cu, etc.

The compounds of the formula (I) preferably serve as a charge transport material (electron conductor). Thus, at least one compound of the formula I as defined above is preferably used in a hole-injecting layer, hole transporting layer or as part of a transparent electrode.

In the EL applications according to the invention low molecular weight or oligomeric as well as polymeric materials may be used as light-emitting layer 5. The substances are characterized by the fact that they are photoluminescing. Accordingly, suitable substances are for example fluorescent dyes and fluorescent products that are forming oligomers or are incorporated into polymers. Examples of such materials are coumarins, perylenes, anthracenes, phenanthrenes, stilbenes, distyryls, methines or metal complexes such as $Alq_3$ (tris(8-hydroxyquinolinato)aluminium), etc. Suitable polymers include optionally substituted phenylenes, phenylene vinylenes or polymers with fluorescing segments in the polymer side chain or in the polymer backbone. A detailed list is given in EP-A-532 798. Preferably, in order to increase the luminance, electron-injecting or hole-injecting layers (3 and/or 7) can be incorporated into the EL arrangements. A large number of organic compounds that transport charges (holes and/or electrons) are described in the literature. Mainly low molecular weight substances are used, which are for example vacuum evaporated in a high vacuum. A comprehensive survey of the classes of substances and their use is given for example in the following publications: EP-A 387 715, U.S. Pat. No. 4,539,507, U.S. Pat. No. 4,720,432 and U.S. Pat. No. 4,769,292. A preferred material is PEDOT (poly-(3,4-ethylenedioxythiophene)) which can also be employed in the transparent electrode of the OLEDs.

As a result of the inventive use of the compounds (I), it is possible to obtain OLEDs with high efficiency. The inventive OLEDs can be used in all devices in which electroluminescence is useful. Suitable devices are preferably selected from stationary and mobile visual display units. Stationary visual display units are, for example, visual display units of computers, televisions, visual display units in printers, kitchen appliances and advertising panels, illuminations and information panels. Mobile visual display units are, for example, visual display units in cell phones, laptops, digital cameras, vehicles and destination displays on buses and trains. Moreover, the compounds (I) may be used in OLEDs with inverse structure. The compounds (I) in these inverse OLEDs are in turn preferably used in the light-emitting layer. The structure of inverse OLEDs and the materials typically used therein are known to those skilled in the art.

Before they are used as charge transport materials or exciton transport materials, it may be advisable to subject the compounds of the formula (I) to a purification process. Suitable purification processes comprise conventional column techniques and conversion of the compounds of the formula (I) to the gas phase. This includes purification by sublimation or PVD (physical vapor deposition).

The invention is illustrated in detail with reference to the following nonrestrictive examples.

EXAMPLES

I. Preparation of Compounds of the General Formula I

Example 1

N,N'-Bis(2,6-diisopropylphenyl)-5H,12H-carbazolo[2,3-b]carbazol[6, 7:13,14]-bis(dicarboximide)

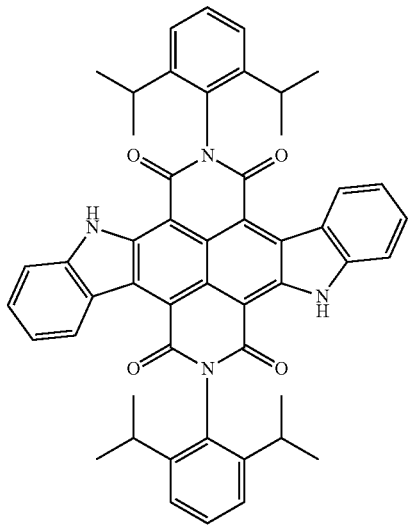 [SMILES: CC(C)c1cccc(C(C)C)c1N1C(=O)c2c3[nH]c4ccccc4c3c3c4c(c5[nH]c6ccccc6c5c(c24)C1=O)C(=O)N(c1c(C(C)C)cccc1C(C)C)C3=O]

N,N'-Di-(2',6'-diisopropylphenyl)-2,6-dibromonaphthalene-1,4,5,8-tetracarboxylic acid bisimide was synthesized as described by S. Chopin et al. in J. Mater. Chem. 2007, 17, 4139-4146. The employed 2,6-Dibromonaphthalenedianhydride was synthesized as described by C. Thalacker et al. in J. Org. Chem. 2006, 71, 8098-8105.

N,N'-Di-(2',6'-diisopropylphenyl)-2,6-dibromonaphthalene-1,4,5,8-tetracarboxylic acid bisimide (60.0 mg, 80.6 µmol), 2-bromoaniline (38.8 mg, 0.226 mmol), Pd(OAc)$_2$ (5.4 mg, 0.024 mmol) and K$_2$CO$_3$ (22.3 mg, 0.161 mmol) were placed under argon and dry dimethylformamide (DMF) (5 mL) was added. The mixture was refluxed in an oil-bath (175° C.) for 2 h. The solvent was removed under reduced pressure and the residue was purified by column chromatography (dichloromethane/pentane 1:1) and recycling-GPC affording a black solid (7.2 mg, 12%).

$^1$H NMR (600 MHz, CD$_2$Cl$_2$): 11.52 (s, 2H), 9.71 (d, $^3$J=7.3 Hz, 2H), 7.74-7.71 (m, 2H), 7.70-7.67 (m, 2H), 7.62 (t, $^3$J=7.9 Hz, 2H), 7.47 (d, $^3$J=7.9 Hz, 4H), 7.40-7.36 (m, 2H), 2.92 (sept, $^3$J=6.9 Hz, 4H), 1.22-1.78 (m, 24H).

$^{13}$C NMR (151 MHz, CD$_2$Cl$_2$): 166.0, 164.9, 146.6, 144.7, 142.8, 131.6, 131.4, 131.0, 130.54, 130.1, 124.7, 122.2, 121.6, 121.1, 120.0, 111.7, 105.1, 29.66, 24.14, 24.11.

HRMS (ESI, acetonitrile/CHCl$_3$ 1:1, pos-mode): calcd for C$_{50}$H$_{45}$N$_4$O$_4$ 765.3435. Found 765.3433.

Example 2

N,N'-Bis(2,6-diisopropylphenyl)-5H,12H-2,9-dichloro-carbazolo[2,3-b]carbazol[6, 7:13,14]bis(dicarboximide)

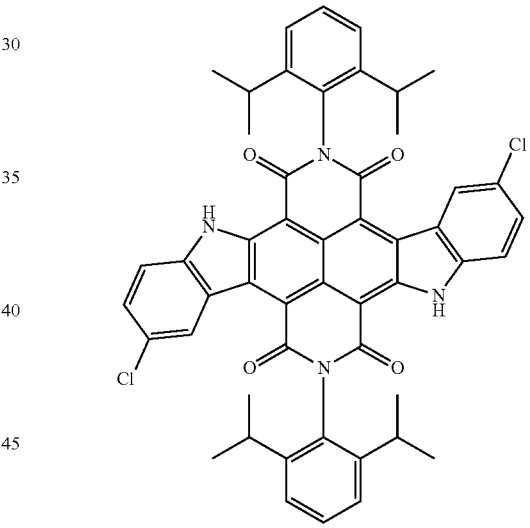

N,N'-Bis(2,6-diisopropylphenyl)-5H,12H-carbazolo[2,3-b]carbazol[6, 7:13,14]-bis(dicarboximide) (28.0 mg, 36.6 µmol) and N-chlorosuccinimide (NCS) (9.8 mg, 73.4 mg) were dissolved in methylenehloride (4 mL), and stirred at room temperature for 2 days. A further portion of NCS (10.0 mg, 74.9 µmol) were added and heated under reflux. The reaction mixture was cooled to room temperature after 15 days. The solvent was removed under reduced pressure. The residue was purified by column chromatography (methylene chloride/pentane 1:1). 10 mg (32% of theory) of a green solid were obtained.

$^1$H NMR (400 MHz, CD$_2$Cl$_2$): 11.55 (s, 2H), 9.78 (d, $^4$J=1.8 Hz, 2H), 7.68 (dd, $^3$J=8.5 Hz, $^4$J=2.0 Hz), 7.64 (t, $^3$J=7.6 Hz, 2H), 7.52 (d, $^3$J=8.4 Hz, 2H), 7.49 (d, $^3$J=7.8 Hz, 4H), 2.87 (sept, $^3$J=6.9 Hz, 4H), 1.26-1.21 (m, 24H).

HRMS (ESI, acetonitrile/CHCl$_3$ 1:1, pos-mode): calcd for C$_{50}$H$_{43}$Cl$_2$N$_4$O$_4$ 833.2656. found 833.2660.

Example 3

N,N'-Bis(2,6-diisopropylphenyl)-5H,12H-2,9-di-cyano-carbazolo[2,3-b]carbazol[6,7:13,14]bis(dicarboximide)

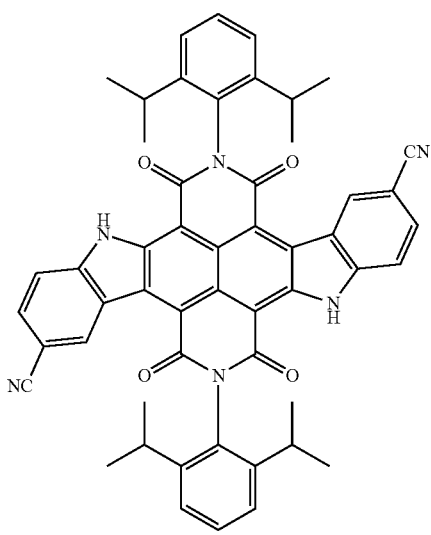 [SMILES: CC(C)c1cccc(C(C)C)c1N1C(=O)c2c3[nH]c4ccc(C#N)cc4c3c3c4c(c5[nH]c6ccc(C#N)cc6c5c(c24)C1=O)C(=O)N(c1c(C(C)C)cccc1C(C)C)C3=O]

N,N'-Di-(2,6-diisopropylphenyl)-2,6-dibromo-naphthalene-1,4:5,8-bis(dicarboximide) (163 mg, 0.219 mmol), 4-amino-3-bromo-benzonitrile (92.3 mg, 0.468 mmol), palladium acetate (8.0 mg, 35.6 μmol), potassium carbonate (61.7 mg, 0.446 mmol), and tetrabutylammonium bromide (142 mg, 0.440 mmol) were added to dry DMF (5 mL) under argon. The reaction mixture was heated under reflux for 50 min. The solvent was removed under reduced pressure after cooling to room temperature. The residue was purified by column chromatography with methylene chloride as the eluent. The fraction containing the product was concentrated to dryness, and then suspended in chloroform (2 mL). The suspension was heated under reflux and filtered after cooling to room temperature. A green residue (29 mg, 16% of theory) was obtained.

$^1$H NMR (400 MHz, CD$_2$Cl$_2$): □□=11.78 (s, 2H), 10.14-10.12 (m, 2H), 7.98 (dd, $^3J$=8.4 Hz, $^4J$=1.6 Hz), 7.78 (dd, $^3J$=8.4 Hz, $^5J$=0.64 Hz), 7.64 (t, $^3J$=7.8 Hz, 2H), 7.49 (d, $^3J$=7.8 Hz, 4H), 2.87 (sept, $^3J$=6.8 Hz, 4H), 1.22, 1.20 (2×d, $^3J$=6.8 Hz, 24H).

HRMS (ESI, acetonitrile/CHCl$_3$ 1:1, pos-mode): calcd for C$_{52}$H$_{43}$N$_6$O$_4$: 815.3340. found: 815.3336.

Example 4

N,N'-Bis(2,6-diisopropylphenyl)-5H,12H-1,3,6,8-tetrakis(trifluormethyl)-carbazolo[2,3-b]carbazol[6,7:13,14]bis(dicarboximide)

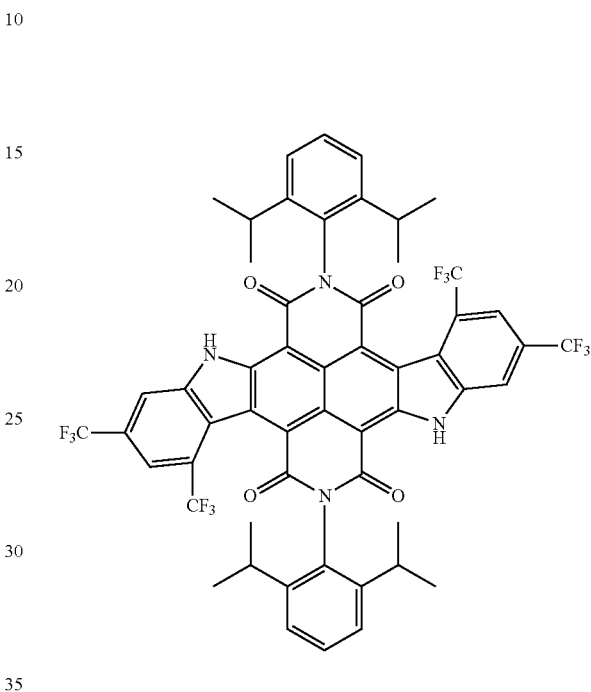

N,N'-Di-(2,6-diisopropylphenyl)-2,6-dibromo-naphthalene-1,4:5,8-bis(dicarboximide) (295 mg, 0.396 mmol), 2-bromo-3,5-bis(trifluoromethyl)-anilin (310 mg, 1.01 mmol), palladium acetate (13.6 mg, 60.6 μmol), potassium carbonate (111 mg, 0.803 mmol), and tetrabutylammonium bromide (261 mg, 0.810 mmol) were added to dry DMF (7 mL) under argon. The reaction mixture was heated to 135° C. for 90 min, and then to 150° C. under reflux for 1 h. The solvent was removed under reduced pressure after cooling to room temperature. The residue was purified by column chromatography with methylene chloride/pentane 3:2 as the eluent. The eluent fraction containing the product was concentrated to dryness (47.6 mg), and then suspended in chloroform (2 mL). The suspension was heated under reflux and filtered after cooling to room temperature. A dark green residue (34.0 mg, 8% of theory) was obtained.

$^1$H NMR (400 MHz, CD$_2$Cl$_2$): □□=11.44 (s, 2H), 7.99 (bs, 2H), 7.85 (bs, 2H), 7.59 (t, $^3J$=7.8 Hz, 2H), 7.42 (d, $^3J$=7.8 Hz, 4H), The alkyl part was not distinctly resolved.

HRMS (ESI, acetonitrile/CHCl$_3$ 1:1, pos-mode): calcd for C$_{54}$H$_{41}$F$_{16}$N$_4$O$_4$: 1037.2931. found: 1037.2926.

Example 5

N,N'-Bis(2-ethylhexyl)-5H,12H-carbazolo[2,3-b]carbazol[6,7:13,14]bis(dicarboximide)

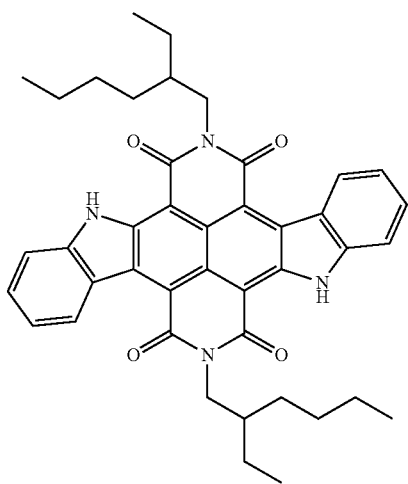 [SMILES: CCCCC(CC)CN1C(=O)c2c3[nH]c4ccccc4c3c3c4c(c5[nH]c6ccccc6c5c(c24)C1=O)C(=O)N(CC(CC)CCCC)C3=O]

N,N"-Di-(2-ethylhexyl)-2,6-dibromo-naphthalene-1,4:5,8-bis(dicarboximide) (156 mg, 0.241 mmol), 2-bromo-anilin (177 mg, 0.68 mmol), palladium acetate (18.2 mg, 0.081 mmol), and potassium carbonate (66.0 mg, 0.478 mmol) were added to dry DMF (10 mL) under argon. The reaction mixture was heated to reflux for 50 min. The solvent was removed under reduced pressure after cooling to room temperature. The residue was purified by column chromatography with methylene chloride/pentane 1:1 as the eluent. A dark residue (16 mg, 10% of theory) was obtained.

$^1$H NMR (400 MHz, CDCl$_3$): 11.52 (s, 2H), 9.76 (d, $^3$J=8.1 Hz, 2H), 7.70-7.68 (m, 2H), 7.56 (d, $^3$J=8.0 Hz, 2H), 7.46-7.41 (m, 2H), 4.42-4.21 (m, 4H), 2.19-2.01 (m, 2H), 1.50-1.27 (m, 16H), 0.99 (t, $^3$J=7.2 Hz, 6H), 0.90 (t, $^3$J=7.4 Hz, 6H).

II. Method for Determining the Transistor Characteristics

Example 6

Highly doped p-type silicon (100) wafers (0.01-0.02 Ω·cm) were used as substrates A. Highly doped p-type silicon (100) wafers (0.005-0.02 Ω·cm) with a 100 nm thick thermally grown SiO$_2$ layer (capacitance 34 nF/cm$^2$) were used as substrates B.

Onto substrates A, a 30 nm thick layer of aluminum is deposited by thermal evaporation in a Leybold UNIVEX 300 vacuum evaporator from a tungsten wire, at a pressure of 2×10$^{-6}$ mbar and with an evaporation rate of 1 nm/s. The surface of the aluminum layer is oxidized by a brief exposure to an oxygen plasma in an Oxford reactive ion etcher (RIE, oxygen flow rate: 30 sccm, pressure: 10 mTorr, plasma power: 200 W, plasma duration 30 sec) and the substrate is then immersed into a 2-propanol solution of a phosphonic acid (1 mMol solution of C$_{14}$H$_{29}$PO(OH)$_2$ [TDPA] and left in the solution for 1 hour, which results in the formation of a self-assembled monolayer (SAM) of phosphonic acid molecules on the aluminum oxide surface. The substrate is taken out of the solution and rinsed with pure 2-propanol, dried in a stream of nitrogen and left for 10 min on a hotplate at a temperature of 100° C. The total capacitance of the AlO$_x$/SAM gate dielectric on substrate A is 810 nF/cm$^2$ in case of C$_{14}$H$_{29}$PO(OH)$_2$.

Figure 1:
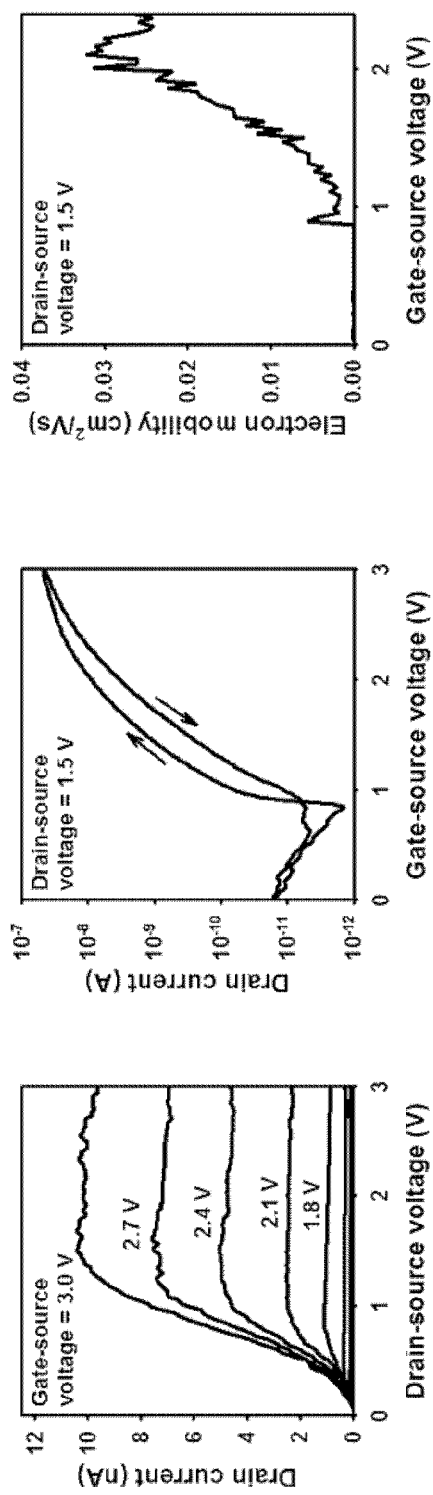
FIG. 1 shows the characteristic data of the TFT of example 2, substrate A with $C_{14}H_{29}PO(OH)_2$ as gate dielectric and the following as semiconductor.

FIG. 1 shows the characteristic data of the TFT of example 6, substrate A.

On substrates B, an about 8 nm thick layer of Al$_2$O$_3$ is deposited by atomic layer deposition in a Cambridge NanoTech Savannah (80 cycles at a substrate temperature of 250° C.). The surface of the aluminum oxide layer is activated by a brief exposure to an oxygen plasma in an Oxford reactive ion etcher (RIE, oxygen flow rate: 30 sccm, pressure: 10 mTorr, plasma power: 200 W, plasma duration 30 sec) and the substrate is then immersed into a 2-propanol solution of a phosphonic acid (1 mMol solution of C$_7$F$_{15}$C$_{11}$H$_{22}$PO(OH)$_2$ [FODPA]) and left in the solution for 1 hour, which results in the formation of a self-assembled monolayer (SAM) of phosphonic acid molecules on the aluminum oxide surface. The substrate is taken out of the solution and rinsed with pure 2-propanol, dried in a stream of nitrogen and left for 10 min on a hotplate at a temperature of 100° C. The total capacitance of the SiO$_2$/AlO$_x$/SAM gate dielectric on substrate B is 32 nF/cm$^2$ (independent on the choice of the phosphonic acid). The contact angle of water on the TDPA-treated substrates is 108°, and on the FODPA-treated substrates 118°.

FIG. 2 shows the characteristic data of the TFT of example 6, substrate B.

A 30 nm thick film of the organic semiconductor is deposited by thermal sublimation in a Leybold UNIVEX 300 vacuum evaporator from a molybdenum boat, at a pressure of 2×10$^{-6}$ mbar and with an evaporation rate of 0.3 nm/s.

For the source and drain contacts 30 nm of gold is evaporated through a shadow mask in a Leybold UNIVEX 300 vacuum evaporator from tungsten boat, at a pressure of 2×10$^{-6}$ mbar and with an evaporation rate of 0.3 nm/s. The transistors have a channel length (L) ranging from 10 to 100 μm and a channel width (W) ranging from 50 to 1000 μm.

To be able to contact the back side of the silicon wafer, the wafer (which also serves as the gate electrode of the transistors) is scratched on the back side and coated with silver ink.

The electrical characteristics of the transistors are measured on a Micromanipulator 6200 probe station using an Agilent 4156C semiconductor parameter analyzer. All measurements are performed in air at room temperature. The probe needles are brought into contact with the source and drain contacts of the transistors by putting them down carefully on top of the gold contacts. The gate electrode is contacted through the metal substrate holder onto which the wafer is placed during the measurements.

To obtain the transfer curve the drain-source voltage (V$_{DS}$) is held to 3 V (in case of substrate A) or 40 V (in case of substrate B). The gate-source voltage V$_{GS}$ is swept at medium speed from 0 to 3 V in steps of 0.03 V (substrate A) or from 0 to 40 V in steps of 0.4 V (substrate B) and back. The charge-carrier mobility is extracted in the saturation regime from the slope of (I$_D$)$^{1/2}$ versus V$_{GS}$.

To obtain the output characteristics the drain-source voltage (V$_{DS}$) is swept at medium speed from 0 to 3 V in steps of 0.03 V (substrate A) and from 0 to 40 V in steps of 0.4 V (substrate B), while the gate-source voltage V$_{GS}$ is held at up to 8 different voltages (e.g. 0, 0.5, 1, 1.5, 2, 2.5, 3 V in case of substrate A or 0, 10, 20, 30, 40 V in case of substrate B).

Table 5 gives the field-effect mobilities (μ) and on/off ratios ($I_{on}/I_{off}$) for compounds of example 1 with a thin (substrate A) and a thick (substrate B) gate dielectric at a certain substrate temperature ($T_{sub}$) measured in ambient air.

TABLE 5

| Compound from Example | Substrate | Substrate Temperature $T_{sub}$ [° C.] | Mobility μ [cm²/Vs] | On/Off Ratio $I_{on}/I_{off}$ |
|---|---|---|---|---|
| 1 | A | 100 | 0.03 | 10⁴ |
| 1 | B | 100 | 0.56 | 10⁶ |

The invention claimed is:

1. A compound of formula I

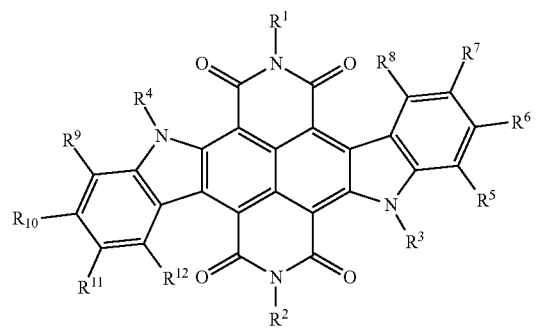

(I)

wherein

R¹, R², R³, and R⁴ are each independently selected from the group consisting of hydrogen and an unsubstituted or a substituted alkyl, cycloalkyl, heterocycloalkyl, aryl and hetaryl group, R⁵, R⁶, R⁷, R⁸, R⁹, R¹⁰, R¹¹ and R¹² are each independently selected from the group consisting of hydrogen, an unsubstituted or a substituted alkyl, alkoxy, alkylthio, (monoalkyl)amino, (dialkyl)amino, cycloalkyl, cycloalkoxy, cycloalkylthio, (monocycloalkyl)amino, (dicycloalkyl)amino, heterocycloalkyl, heterocycloalkoxy, heterocycloalkylthio, (monoheterocycloalkyl)amino, (diheterocycloalkyl)amino, aryl, aryloxy, arylthio, (monoaryl)amino, (diaryl)amino, hetaryl, hetaryloxy, hetarylthio, (monohetaryl)amino, (dihetaryl)amino group, a halogen atom, a hydroxy group, a mercapto group, a cyano group, a nitro group, a cyanato group, a thiocyanato group, a formyl group, an acyl group, a carboxy group, a carboxylate group, an alkylcarbonyloxy group, a carbamoyl group, an alkylaminocarbonyl group, a dialkylaminocarbonyl group, a sulfo group, a sulfonate group, a sulfoamino group, a sulfamoyl group, an alkylsulfonyl group, an arylsulfonyl group, an amidino group, and a NE¹E² group, where E¹ and E² are each independently hydrogen, an alkyl group, a cycloalkyl group, a heterocycloalkyl group, an aryl group or a hetaryl group, and in each case at least two adjacent radicals from R⁵, R⁶, R⁷, R⁸, R⁹, R¹⁰, R¹¹ and R¹², together with the carbon atoms of the benzene ring to which R⁵, R⁶, R⁷, R⁸, R⁹, R¹⁰, R¹¹ and R¹² are bonded, optionally form a fused ring system comprising 1, 2, 3, 4, 5, 6, 7 or 8 further rings.

2. The compound according to claim 1, wherein at least one of R¹, R², R³ and R⁴ is selected from the group consisting of A.1-A.16 shown as follows:

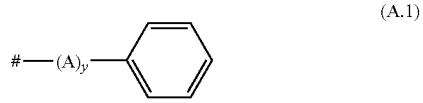
(A.1)

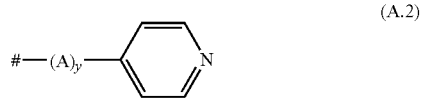
(A.2)

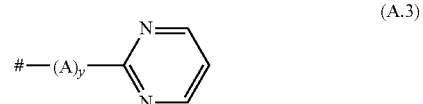
(A.3)

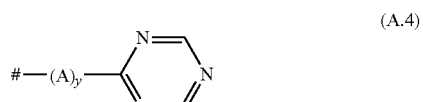
(A.4)

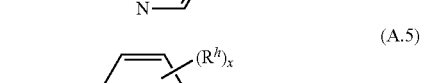
(A.5)

(A.6)

(A.7)

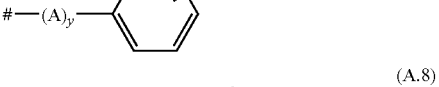
(A.8)

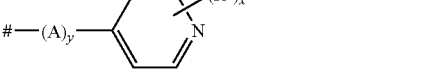
(A.9)

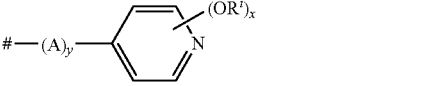
(A.10)

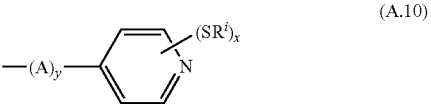
(A.11)

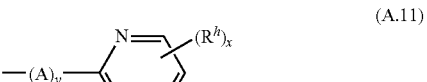
(A.12)

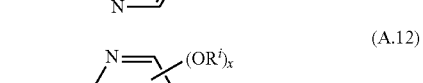
(A.13)

-continued

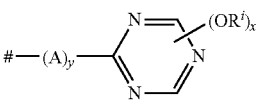 (A.14)

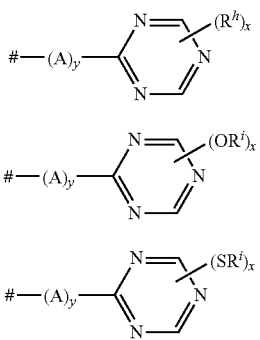 (A.15)

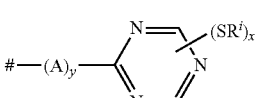 (A.16)

wherein # is a bonding side to a nitrogen atom,

A C$_1$-C$_{10}$-alkylene group which is optionally interrupted by one or more nonadjacent groups selected from the group consisting of —O— and —S—, y is 0 or 1, R$^h$ in A.5, A.8, A.11 and A.14 are each independently a C$_1$-C$_{30}$-alkyl group, a C$_1$-C$_{30}$-fluoroalkyl group, fluorine, chlorine, bromine, a nitro group, a cyano group, or a NE$^1$E$^2$ group, where E$^1$ and E$^2$ are independently hydrogen, an alkyl group, a cycloalkyl group, a heterocycloalkyl group, an aryl group or a hetaryl group, R$^i$ in A.6, A.7, A.9, A.10, A.12, A.13, A.15 and A.16 are each independently a C$_1$-C$_{30}$-alkyl group, x in A.5, A.6 and A.7 is 1, 2, 3, 4 or 5, x in A.8, A.9 and A.10 is 1, 2, 3 or 4, x in A.11, A.12 and A.13 is 1, 2 or 3, and x in A.14, A.15 and A.16 is 1 or 2.

3. The compound according to claim 1, wherein at least one of R$^5$, R$^6$, R$^7$, R$^8$, R$^9$, R$^{10}$, R$^{11}$ and R$^{12}$ is selected from the group consisting of B.1-B.16 shown as follows:

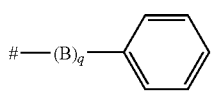 (B.1)

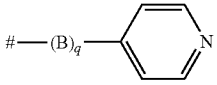 (B.2)

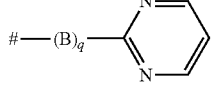 (B.3)

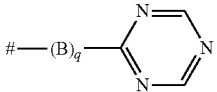 (B.4)

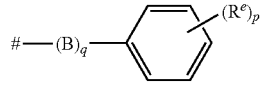 (B.5)

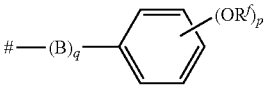 (B.6)

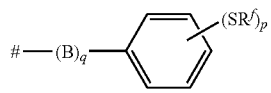 (B.7)

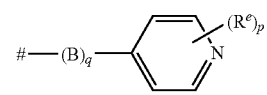 (B.8)

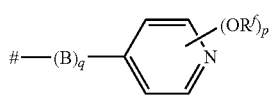 (B.9)

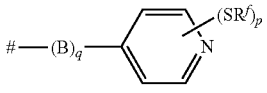 (B.10)

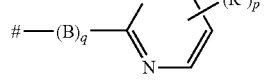 (B.11)

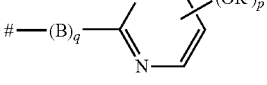 (B.12)

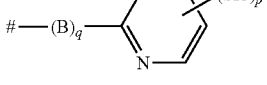 (B.13)

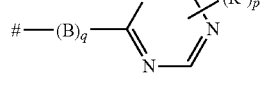 (B.14)

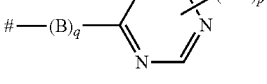 (B.15)

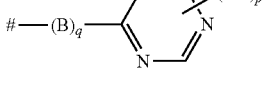 (B.16)

wherein # is a bonding side to a nitrogen atom,

B is a divalent bridging group selected from the group consisting of —O—, —S— or C$_1$-C$_{10}$-alkylene which optionally interrupted or terminated by one or more nonadjacent groups of —O— or —S—, q is 0 or 1, R$^e$ in B.5, B.8, B.11 and B.14 are each independently a C$_1$-C$_{30}$-alkyl group, a C$_1$-C$_{30}$-fluoroalkyl group, fluorine, chlorine, bromine, a nitro group, a cyano group, or a NE$^1$E$^2$ group, where E$^1$ and E$^2$ are each independently hydrogen, an alkyl group, a cycloalkyl group, a heterocycloalkyl group, an aryl group or a hetaryl group, R$^f$ in B.6, B.7, B.9, B.10, B.12, B.13, B.15 and B.16 are each independently a C$_1$-C$_{30}$-alkyl group, p in B.5, B.6 and B.7 is 1, 2, 3, 4 or 5, p in B.8, B.9 and B.10 is 1, 2, 3 or 4, p in B.11, B.12 and B.13 is 1, 2 or 3, and p in B.14, B.15 and B.16 is 1 or 2.

4. A compound according to claim 1, wherein at least one of $R^1$, $R^2$, $R^3$, $R^4$, $R^5$, $R^6$, $R^7$, $R^8$, $R^9$, $R^{10}$, $R^{11}$ and $R^{12}$ is a linear $C_1$-$C_{30}$-alkyl radical or a branched $C_3$-$C_{30}$-alkyl radical.

5. The compound according to claim 1, wherein
at least one of $R^1$, $R^2$, $R^3$, $R^4$, $R^5$, $R^6$, $R^7$, $R^8$, $R^9$, $R^{10}$, $R^{11}$ and $R^{12}$ is a radical of formula (C)

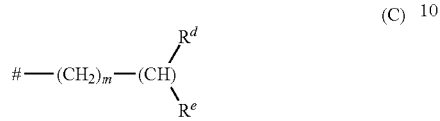
(C)

# is a bonding site,
m is 0 or 1, and
$R^d$ and $R^e$ are each independently a $C_1$- to $C_{30}$-alkyl group.

6. The compound according to claim 1, wherein
at least one of $R^1$, $R^2$, $R^3$, $R^4$, $R^5$, $R^6$, $R^7$, $R^8$, $R^9$, $R^{10}$, $R^{11}$ and $R^{12}$ is a radical of formula (C1)

(C1)

# is a bonding site,
$R^d$ and $R^e$ are each independently a $C_1$- to $C_{28}$-alkyl group, and
a sum of carbon atoms of $R^d$ and $R^e$ is an integer of from 2 to 29.

7. The compound according to claim 1, wherein at least one of $R^1$, $R^2$, $R^3$, $R^4$, $R^5$, $R^6$, $R^7$, $R^8$, $R^9$, $R^{10}$, $R^{11}$ and $R^{12}$ is a perfluoro-$C_1$-$C_{30}$-alkyl group, a 1H,1H-perfluoro-$C_2$-$C_{30}$-alkyl group or a 1H,1H,2H,2H-perfluoro-$C_3$-$C_{30}$-alkyl group.

8. The compound according to claim 1, wherein $R^1$ and $R^2$ are the same.

9. The compound according to claim 1, wherein $R^3$ and $R^4$ are the same.

10. The compound according to claim 1, wherein $R^1$ and $R^2$ are both 2,6-diisopropylphenyl.

11. The compound according to claim 1, wherein $R^3$ and $R^4$ are both hydrogen.

12. The compound according to claim 1, wherein
$R^5$ is the same as $R^9$,
$R^6$ is the same as $R^{10}$,
$R^7$ is the same as $R^{11}$, and
$R^8$ is the same as $R^{12}$.

13. The compound according to claim 1, wherein $R^5$, $R^6$, $R^7$, $R^8$, $R^9$, $R^{10}$, $R^{11}$ and $R^{12}$ are all hydrogen.

14. The compound according to claim 1, wherein $R^5$, $R^6$, $R^8$, $R^9$, $R^{10}$ and $R^{12}$ are all hydrogen, and $R^7$ and $R^{11}$ are Cl.

15. The compound according to claim 1, wherein $R^5$, $R^6$, $R^8$, $R^9$, $R^{10}$ and $R^{12}$ are all hydrogen, and $R^7$ and $R^{11}$ are F.

16. The compound according to claim 1, wherein $R^5$, $R^6$, $R^8$, $R^9$, $R^{10}$ and $R^{12}$ are all hydrogen, and $R^7$ and $R^{11}$ are Br.

17. The compound according to claim 1, wherein $R^5$, $R^6$, $R^8$, $R^9$, $R^{10}$ and $R^{12}$ are all hydrogen, and $R^7$ and $R^{11}$ are CN.

18. The compound according to claim 1, wherein
$R^5$, $R^7$, $R^9$ and $R^{11}$ are hydrogen, and
$R^6$, $R^8$, $R^{10}$ and $R^{12}$ are $CF_3$.

19. A process for preparing the compound according to claim 1, the process comprising:
reacting a 2,6-dibromonaphthalene-1,4,5,8-tetracarboxylic acid bisimide of formula (II)
with a compound of formula (IIIa) and, optionally, a different compound of formula (IIIb):

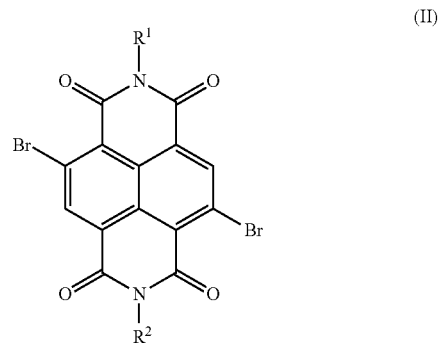
(II)

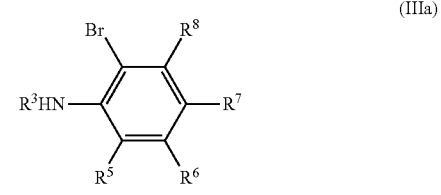
(IIIa)

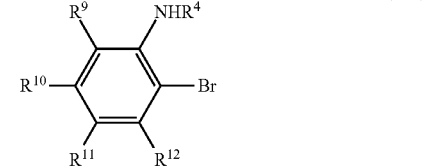
(IIIb)

wherein
$R^1$ and $R^2$ are each independently selected from the group consisting of hydrogen and an unsubstituted or a substituted alkyl, cycloalkyl, heterocycloalkyl, aryl and hetaryl group,
$R^3$ and $R^4$ are each independently selected from the group consisting of hydrogen and an unsubstituted or a substituted alkyl, cycloalkyl, heterocycloalkyl, aryl and hetaryl group,
$R^5$, $R^6$, $R^7$, $R^8$, $R^9$, $R^{10}$, $R^{11}$ and $R^{12}$ are each independently selected from the group consisting of
hydrogen,
an unsubstituted or a substituted alkyl, alkoxy, alkylthio, (monoalkyl)amino, (dialkyl)amino, cycloalkyl, cycloalkoxy, cycloalkylthio, (monocycloalkyl)amino, (dicycloalkyl)amino, heterocycloalkyl, heterocycloalkoxy, heterocycloalkylthio, (monoheterocycloalkyl)amino, (diheterocycloalkyl)amino, aryl, aryloxy, arylthio, (monoaryl)amino, (diaryl)amino, hetaryl, hetaryloxy, hetarylthio, (monohetaryl)amino, and (dihetaryl)amino group,
a halogen atom, a hydroxy group, a mercapto group, a cyano group, a nitro group, a cyanato group, a thiocyanato group, a formyl group, an acyl group, a carboxy group, a carboxylate group, an alkylcarbonyloxy group, a carbamoyl group, an alkylaminocarbonyl group, a dialkylaminocarbonyl group, a sulfo group, a sulfonate group, a sulfoamino group, a sulfamoyl group, an alkylsulfonyl group, an arylsulfonyl group, an amidino group, and a $NE^1E^2$ group, where $E^1$ and $E^2$ are each independently hydrogen, an alkyl group, a cycloalkyl group, a heterocycloalkyl group, an aryl group or a hetaryl group.

20. An organic field-effect transistor, comprising:
a substrate comprising a gate structure,
a source electrode,
a drain electrode, and
a semiconductor material, which comprises the compound according to claim 1.

21. A substrate, comprising a plurality of organic field-effect transistors,
wherein at least some of the field-effect transistors comprise at least one compound according to claim 1.

22. A semiconductor unit, comprising at least one substrate according to claim 21.

23. An electroluminescent arrangement, comprising:
an upper electrode,
a lower electrode,
an electroluminescent layer, and
optionally an auxiliary layer,
wherein at least one of the upper electrode and the lower electrode is transparent, and
the electroluminescent arrangement comprises at least one compound according to claim 1.

24. The electroluminescent arrangement according to claim 23, wherein the at least one compound is present in a hole-injecting layer or as part of a transparent electrode.

25. The electroluminescent arrangement according to claim 23 is an organic light-emitting diode (OLED).

26. An organic solar cell, comprising at least one compound according to claim 1.

27. A semiconductor material, comprising the compound according to claim 1.

28. A semiconductor in an organic field-effect transistor, comprising the semiconductor unit according to claim 22.

* * * * *